US009416348B2

(12) United States Patent
Hui et al.

(10) Patent No.: US 9,416,348 B2
(45) Date of Patent: Aug. 16, 2016

(54) HEPATOCYTE-LIKE CELLS AND USES THEREOF

(75) Inventors: Lijian Hui, Shanghai (CN); Pengyu Huang, Shanghai (CN); Xin Wang, Shanghai (CN)

(73) Assignees: Shanghai Institutes for Biological Sciences, Shanghai (CN); Chinese Academy of Sciences, Shanghai (CN)

( * ) Notice: Subject to any disclaimer, the term of this patent is extended or adjusted under 35 U.S.C. 154(b) by 67 days.

(21) Appl. No.: 13/883,748

(22) PCT Filed: Nov. 4, 2011

(86) PCT No.: PCT/CN2011/001857
§ 371 (c)(1),
(2), (4) Date: Jun. 19, 2013

(87) PCT Pub. No.: WO2012/058868
PCT Pub. Date: May 10, 2012

(65) Prior Publication Data
US 2013/0330304 A1 Dec. 12, 2013

(30) Foreign Application Priority Data
Nov. 4, 2010 (CN) .......................... 2010 1 0531420

(51) Int. Cl.
C12N 5/00 (2006.01)
C12N 5/02 (2006.01)
C12N 5/071 (2010.01)
A61M 37/00 (2006.01)

(52) U.S. Cl.
CPC ............... *C12N 5/067* (2013.01); *A61M 37/00* (2013.01); *C12N 2501/60* (2013.01); *C12N 2506/1307* (2013.01); *C12N 2510/00* (2013.01)

(58) Field of Classification Search
CPC .................... C12N 2506/1307; C12N 5/067
See application file for complete search history.

(56) References Cited

FOREIGN PATENT DOCUMENTS

| WO | WO2007140968 | 12/2007 |
| WO | WO2009013254 | 1/2009 |
| WO | WO2011102532 | 8/2011 |
| WO | WO2011141405 | 11/2011 |

OTHER PUBLICATIONS

NM_008260, published Oct. 17, 2010 http://www.ncbi.nlm.nih.gov/nuccore/118130865?sat=14&satkey=4178466 Accessed on Feb. 6, 2015.*
Genbank NM_008092, published Nov. 1, 2009, http://www.ncbi.nlm.nih.gov/nuccore/110681730?sat=13&satkey=7538466 Accessed on Feb. 6, 2015.*
Genbank NM_010446, published Oct. 18, 2009, http://www.ncbi.nlm.nih.gov/nuccore/153945803?sat=13&satkey=5678070 Accessed Feb. 6, 2015.*
Genbank NM_009327 (published Nov. 1, 2009, http://www.ncbi.nlm.nih.gov/nuccore/166295201?sat=13&satkey=7555724 Accessed Feb. 6, 2015.*
Feng2008, PNAS, 4005:6057-662.*
Sekiya; Nature, Jul. 2011, 475:390-395.*
Takahashi 2007, Cell, 131:861-872.*
Meissner (Nature Biotechnology, 2007, 25:1177-1181).*
Heng et al, 2005a, Cell Tissue Res, 321:147-150.*
Heng, 2005b, Biomedicine and Pharmacotherapy, 59:132-134.*
Kim (2009, Cell Stem Cell, 4:472-476).*
Zhou (Cell Stem Cell, 2009, 4:381-384).*
Warren (2010, Cell Stem Cell, 7:618-630).*
Basma, et al., "Differentiation and Transplantation of Human Embryonic Stem Cell-Derived Hepatocytes", Gastroenterology 2009, vol. 136, No. 3, Mar. 2009, pp. 990-1004.
Cirillo, et al., "Opening of Compacted Chromatin by Early Developmental Transcription Factors HNF3 (FoxA) and GATA-4", Molecular Cell, vol. 9, Feb. 2002, pp. 279-289.
Cristiano, et al., "Molecular Conjugates: A Targeted Gene Delivery Vector for Molecular Medicine", Springer-Verlag, Jul. 1995, pp. 479-486.
Duan, et al., "Differentiation and Enrichment of Hepatocyte-Like Cells from Human Embryonic Stem Cells in Vitro and In Vivo", Stem Cells Dec. 2007, pp. 3058-3069.
Feng, et al., "PU.1 and C/EBPα/β Convert Fibroblasts Into Macrophage-Like Cells", PNAS, Apr. 22, 2008, vol. 105, No. 16, pp. 6057-6062.
Gebhardt, et al. "Biliary Secretion of Sodium Fluorescein in Primary Monolayer Cultures of Adult Rat Hepatocytes and its Stimulation by Nicotinamide", J. Cell Science 56, Aug. 1982, pp. 233-244.
Gouon-Evans, et al., "BMP-4 is Required for Hepatic Specification of Mouse Embryonic Stem Cell-Derived Definitive Endoderm", Nature Biotechnology, vol. 24, No. 11, Nov. 2006, pp. 1402-1411.
Grompe, et al., "Loss of Fumarylacetoacetate Hydrolase is Responsible for the Neonatal Hepatic Dysfunction Phenotype of Lethal Albino Mice", Genese & Development, Dec. 1993, pp. 2297-2307.
Grompe, et al., "Pharmacological Correction of Neonatal Lethal Hepatic Dysfunction in a Murine Model of Hereditary Tyrosinaemia Type 1", Nature Genetics, vol. 10, Aug. 1995, pp. 453-460.
Huang, et al., "Induction of Functional Hepatocyte-Like Cells From Mouse Fibroblasts by Defined Factors", Nature, vol. 475, Jul. 21, 2011, pp. 386-391.
Hui, et al., "p38 Suppresses Normal and Cancer Cell Proliferation by Antagonizing the JNK-c-Jun Pathway", Nature Genetics, vol. 39, No. 6, Mar. 2007, pp. 741-749.
Ieda, et al., "Direct Reprogramming of Fibroblasts into Functional Cardiomyocytes by Defined Factors", Cell 142, Aug. 6, 2010, pp. 375-386.
Kanda, et al., "In Vitro Differentiation of Hepatocyte-Like Cells From Embryonic Stem Cells Promoted by Gene Transfer of Hepatocyte Nuclear Factor 3", Hepatology Research 26, Feb. 2003, pp. 225-231.
Kane, et al., "Purification and Characterization of Human Coagulation Factor V", The Journal of Biological Chemistry, vol. 256, No. 2, Jan. 25, 1981, pp. 1002-1007.

(Continued)

*Primary Examiner* — Valarie Bertoglio
(74) *Attorney, Agent, or Firm* — Lee & Hayes, PLLC

(57) ABSTRACT

The present invention relates to hepatocyte-like cells. Also disclosed are methods of making the cells and using the cells.

11 Claims, 12 Drawing Sheets

(56) References Cited

OTHER PUBLICATIONS

Kyrmizi, et al., "Plasticity and Expanding Complexity of the Hepatic Transcription Factor Network During Liver Development", Genes & Development 20:2293-2305, Jun. 2006, 14 pages.
Li, et al., "Hepatoblast-Like Progenitor Cells Derived From Embryonic Stem Cells Can Repopulate Livers of Mice", Gastroenterology, vol. 139, No. 6, Dec. 2010, pp. 2158-2178.
Li, et al., "The Ink4/Arf Locus is a Barrier for iPS Cell Reprogramming", Nature, Letters, vol. 460, Aug. 27, 2009, pp. 1136-1141.
Liu, "Effects of the Lentivirus Mediated Constitutive Expression of Foxa2 and Hnf4a Upon the Heptic Differentiation of Embryonic Stem Cells", Tao Liu Chinese Doctoral Dissertation, May 2011, 125 pgs.
Mikula, et al., "Immortalized p19ARF Null Hepatocytes Restore Liver Injury and Generate Hepatic Progenitors After Transplantation", Hepatology, vol. 39, No. 3, Mar. 2004, pp. 628-634.
Miyoshi, et al., "Hepatocyte Culture Utilizing Porous Polyvinyl Formal Resin Maintains Long-term Stable Albumin Secretion Activity", Journal Biomaterials Science, Polymer Edition, vol. 9 No. 3, Feb. 1998, pp. 227-237.
Odom, et al., "Control of Pancreas and Liver Gene Expression by HNF Transcription Factors", www.sciencemag.org, Science, vol. 303, Feb. 27, 2004, 5 pages.
Overturf, et al., "Hepatocytes Corrected by Gene Therapy are Selected in Vivo in a Murine Model of Hereditary Tyrosinaemia Type I", 1996 Nature Genetics, vol. 12, Mar. 1996, pp. 266-273.
Passier, et al., "Getting to the Heart of the Matter: Direct Reprogramming to Cardiomyocytes", Cell Stem Cell, Aug. 6, 2010, pp. 139-141.
Passonneau, et al., "A Comparison of Three Methods of Glycogen Measurement in Tissues", Analytical Biochemistry 60, Aug. 1974, pp. 405-412.
Rausa, et al., "Association Between Hepatocyte Nuclear Factor 6 (HNF-6) and FoxA2 DNA Binding Domains Stimulates FoxA2 Transcriptional Activity but Inhibits HNF-6 DNA Binding", Molecular and Cellular Biology, vol. 23, No. 2, Jan. 2003, pp. 436-449.
Schrem, et al., "Liver-Enriched Transcription Factors in Liver Function and Development. Part I: The Hepatocyte Nuclear Factor Network and Liver-Specific Gene Expression", Pharmacological Reviews, vol. 54, No. 1, Mar. 2002, pp. 129-158.
Schrem, et al., "Liver-Enriched Transcription Factors in Liver Function and Development. Part II: The C/EBPs and D Site-Binding Protein in Cell Cycle Control, Carcinogenesis, Circadian Gene Regulation, Liver Regeneration, Apoptosis, and Liver-Specific Gene Regulation", Pharmacological Reviews, vol. 56, No. 2, Jun. 2004, pp. 291-330.
Shen, et al., "Molecular Basis of Transdifferentiation of Pancreas to Liver", Nature Cell Biology, vol. 2, Dec. 2000, pp. 879-889.
Si-Tayeb, et al., "Highly Efficient Generation of Human Hepatocyte-Like Cells from Induced Pluripotent Stem Cells", Hepatology, Jan. 2010, pp. 297-305.
Soto-Gutierrez, "Reversal of Mouse Hepatic Failure Using an Implanted Liver-Assist Device Containing ES Cell-Derived Hepatocytes", Nature Biotechnology, vol. 24, No. 11, Nov. 2006, pp. 1412-1420.
Sullivan, et al., "Generation of Functional Human Hepatic Endoderm from Human Induced Pluripotent Stem Cells", Hepatology, Jan. 2010, pp. 329-335.
Suzuki, et al., "Tbx3 Controls the Fate of Hepatic Progenitor Cells in Liver Development by Suppressing p19ARF Expression", Research Report, Development 135, Feb. 25, 2008, pp. 1589-1595.
Szabo, et al., "Direct Conversion of Human Fibroblasts to Multilineage Blood Progenitors", Nature, vol. 468, Nov. 25, 2010, pp. 521-528.
Tachikawa, et al., "Regulation of the Endogenous VEGF-A Gene by Exogenous Designed Regulatory Proteins", Pharmacology PNAS, vol. 101, No. 42, Oct. 2004, 6 pages.
Vierbuchen, et al., "Direct Conversion of Fibroblasts to Functional Neurons by Defined Factors", Nature, vol. 463, Feb. 25, 2010, pp. 1035-1042.
Wang, et al., "The Origin and Liver Repopulating Capacity of Murine Oval Cells", PNAS, vol. 100, Suppl. 1, Sep. 30, 2003, 8 pages.
Xie, et al., "Stepwise Reprogramming of B Cells into Macrophages", Cell, vol. 117, May 28, 2004, pp. 663-676.
Zaret, Kenneth S., "Genetic Programming of Liver and Pancreas Progenitors: Lessons for Stem-Cell Differentiation", Nature Reviews, Genetics, vol. 9, May 2008, pp. 329-340.
Zaret, et al., "Pioneer Factors, Genetic Competence, and Inductive Signaling: Programming Liver and Pancreas Progenitors from the Endoderm", Cold Spring Harbor Symp Quant Biol, Nov. 21, 2008, 9 pages.
Zern, Mark A., "Cell Transplantation to Replace Whole Liver Transplantation", Gastroenterology 136, Editorials, Mar. 2009, pp. 767-769.
Zhou, et al., "In Vivo Reprogramming of Adult Pancreatic Exocrine Cells to B-Cells", Nature, vol. 455, Oct. 2, 2008, pp. 627-633.
Aasen, et al., "Efficient and Rapid Generation of Induced Pluripotent Stem Cells from Human Keratinocytes", Nat. Biotechnol., 2008, vol. 26 (11), pp. 1276-1284.
Fusaki, et al., "Efficient Induction of Transgene-Free Human Pluripotent Stem Cells Using a Vector Based on Sendai Virus, an RNA Virus That Does Not Integrate Into the Host Genome", Proc. Jpn. Acad., 2009, vol. 85 (8), pp. 348-362.
International Preliminary Report on Patentability dated May 7, 2013 in PCT Application No. PCT/CN2011/001857.
Jia, et al., "A Nonviral Minicircle Vector for Deriving Human iPS Cells", Nature Methods, 2010, vol. 7 (3), pp. 197-199.
Loh, et al., "Reprogramming of T Cells from Human Peripheral Blood", Cell Stem Cell, 2010, vol. 7 (1), pp. 15-19.
Okita, et al., "Generation of Mouse Induced Pluripotent Stem Cells Without Viral Vectors", Science, 2008, vol. 322, pp. 949-953.
Search Report & Written Opinion dated Feb. 9, 2012 in PCT Application No. PCT/CN2011/001857.
Stadtfeld, et al., "Induced Pluripotency: History, Mechanisms, and Applications", Genes Dev., 2010, vol. 24 (20), pp. 2239-2263.
Stadtfeld, et al., "Reprogramming of Pancreatic Beta Cells into Induced Pluripotent Stem Cells", Curr. Biol., 2008, vol. 18 (12), pp. 890-894.
Staerk, et al., "Reprogramming of Peripheral Blood Cells to Induced Pluripotent Stem Cells", Cell Stem Cell, 2010, vol. 7 (1), pp. 20-24.
Varas, et al., "Fibroblast-Derived Induced Pluripotent Stem Cells Show No Common Retroviral Vector Insertions", Stem Cells, 2009, vol. 27, pp. 300-306.
Winkler, et al., "No Evidence for Clonal Selection Due to Lentiviral Integration Sites in Human Induced Pluripotent Stem Cells", Stem Cells, 2010, vol. 28, pp. 687-694.
Yu, et al., "Human Induced Pluripotent Stem Cells Free of Vector and Transgene Sequences", Science, 2009, vol. 324, pp. 797-801.
Zhou, et al., "Adenoviral Gene Delivery Can Reprogram Human Fibroblasts to Induced Pluripotent Stem Cells", Stem Cells, 2009, vol. 27, pp. 2667-2674.

* cited by examiner

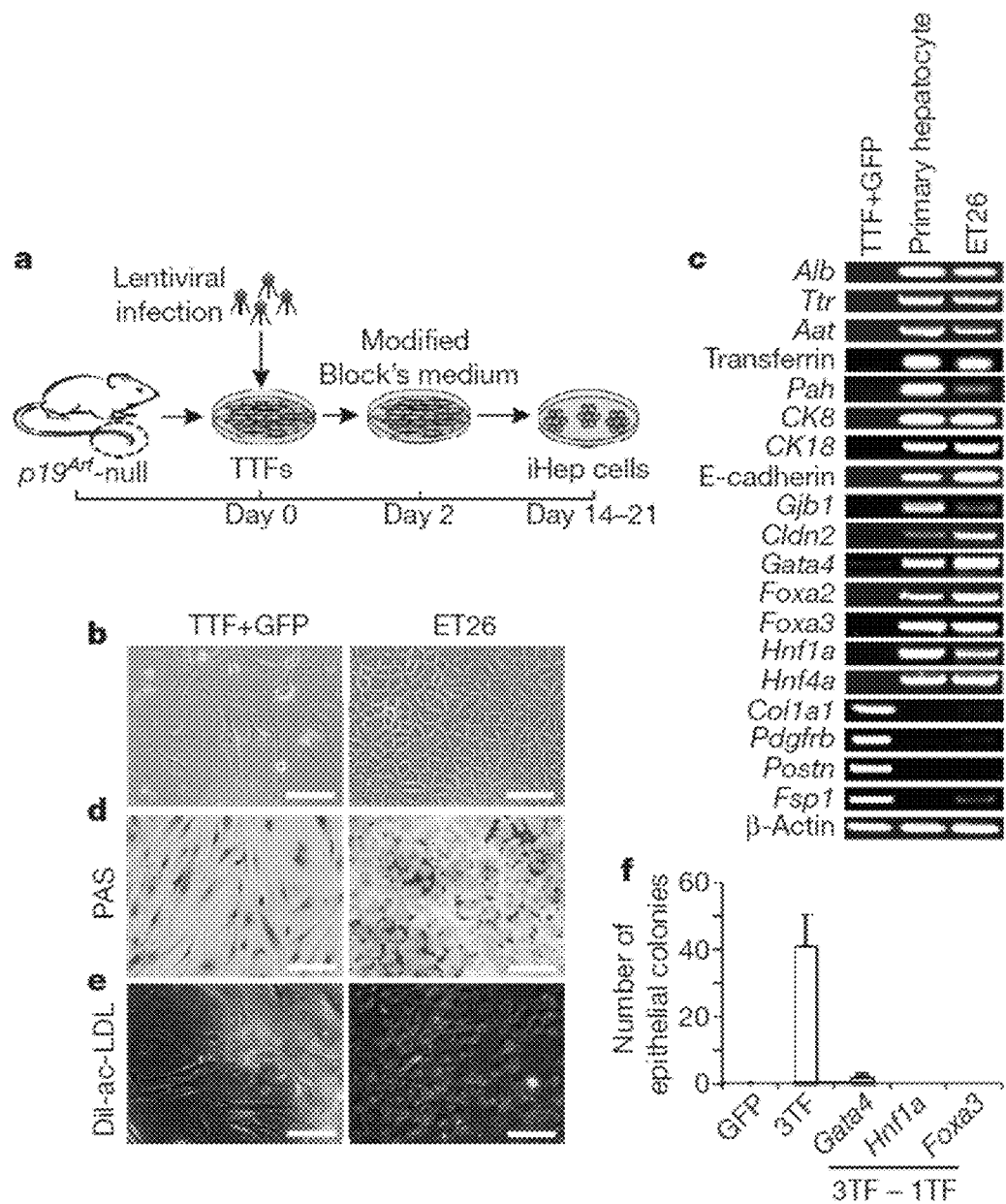
FIGs. 1a-f

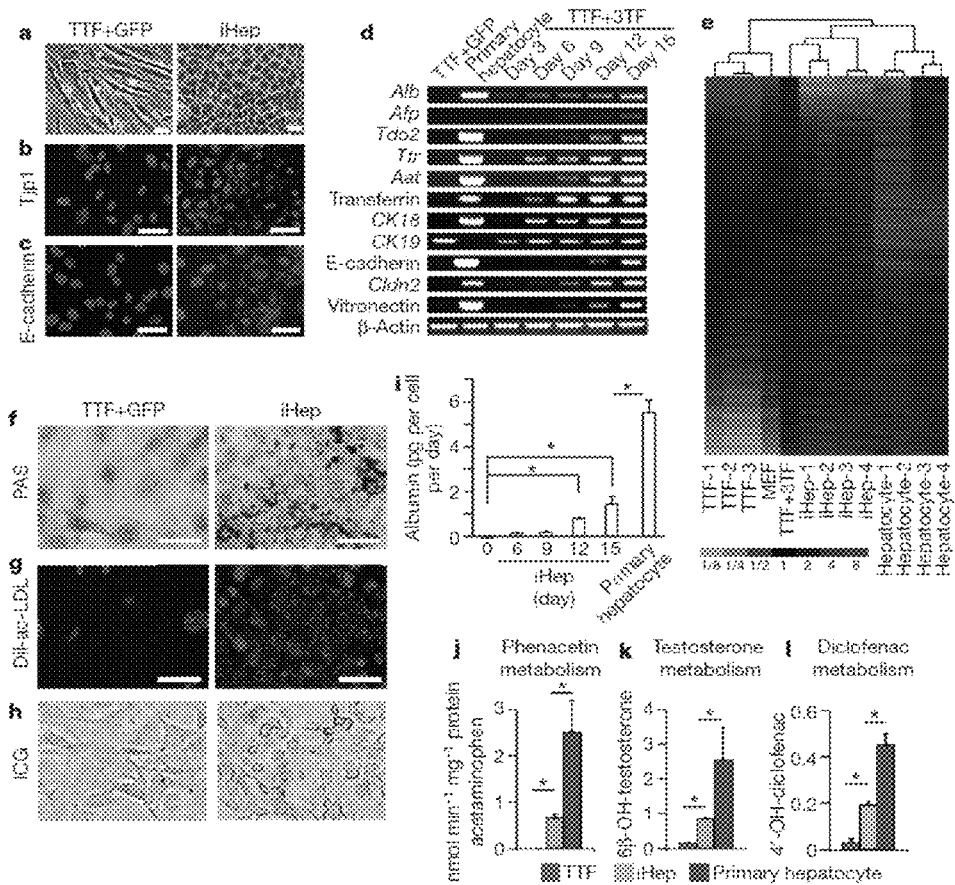
FIGs. 2a-l
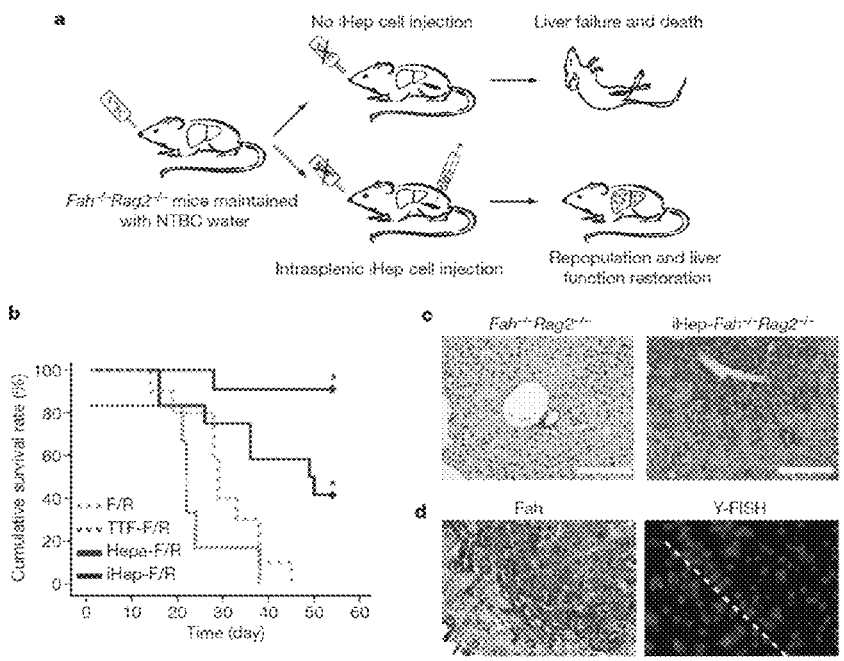
FIGs. 3a-d

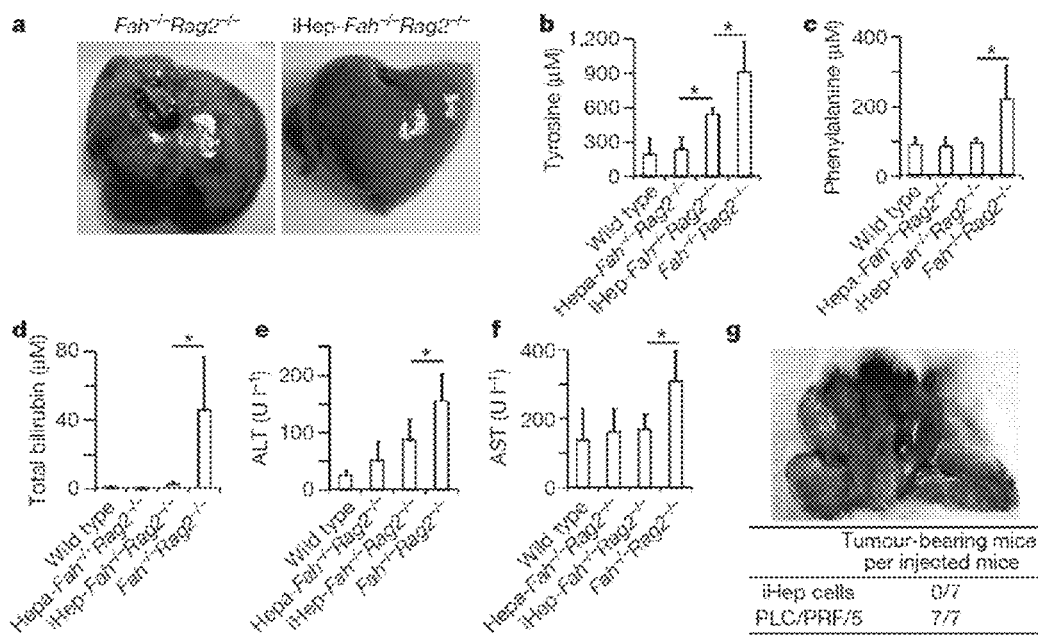
FIGs. 4a-g
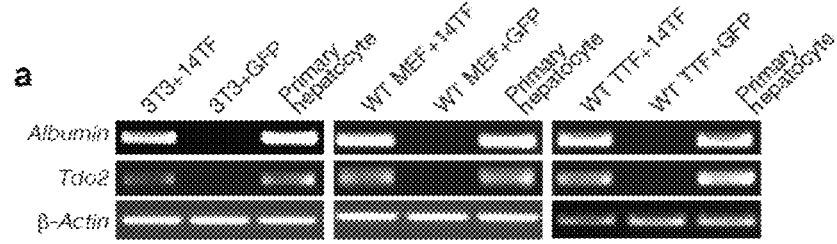
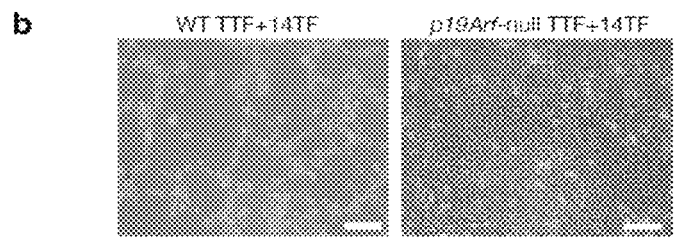
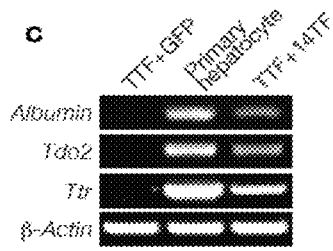
FIGs. 5a-c

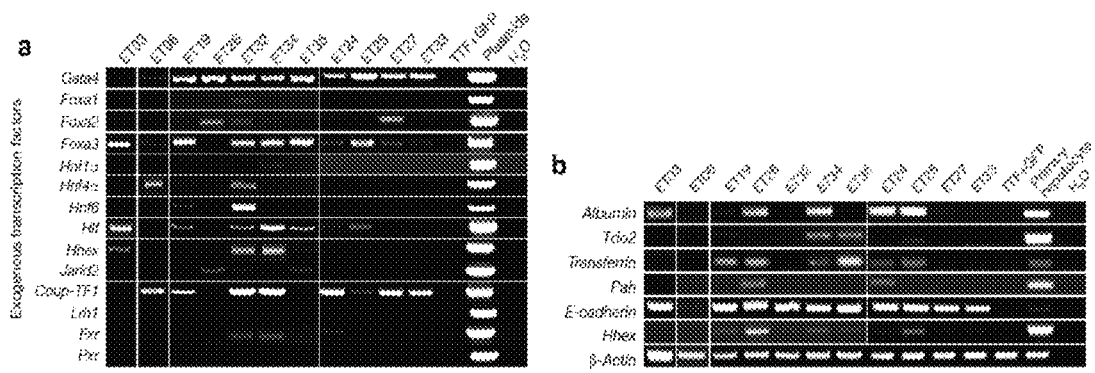
FIGs. 6a and b
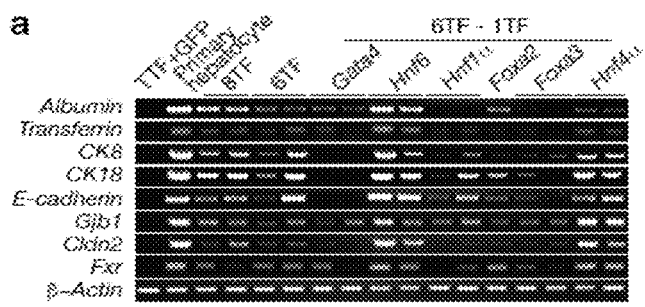
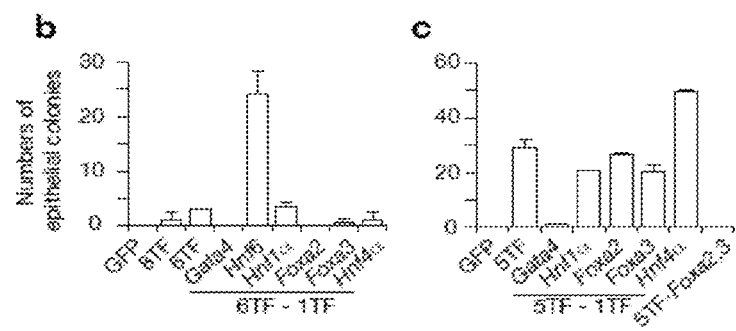
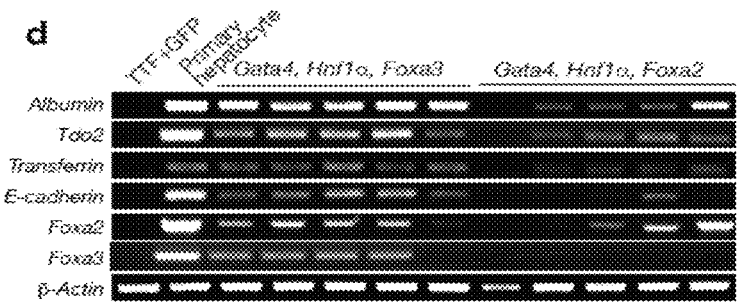
FIGs. 7a-d

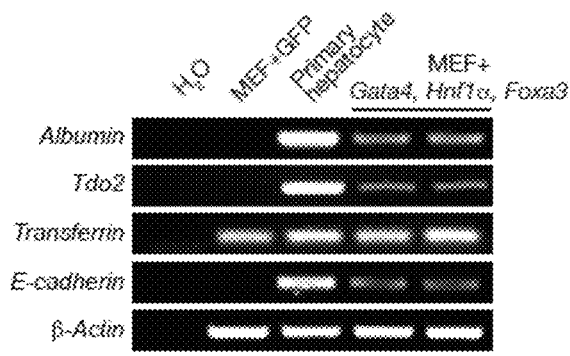
FIG. 8
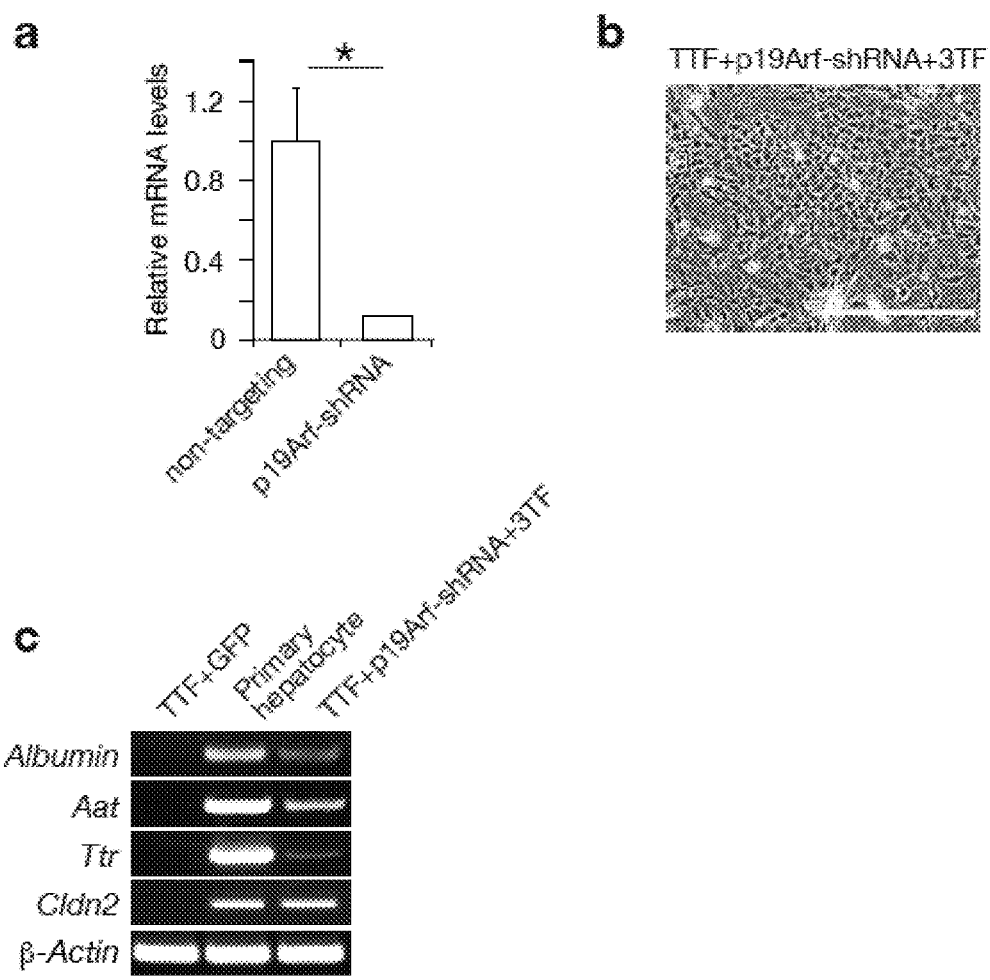
FIGs. 9a-c

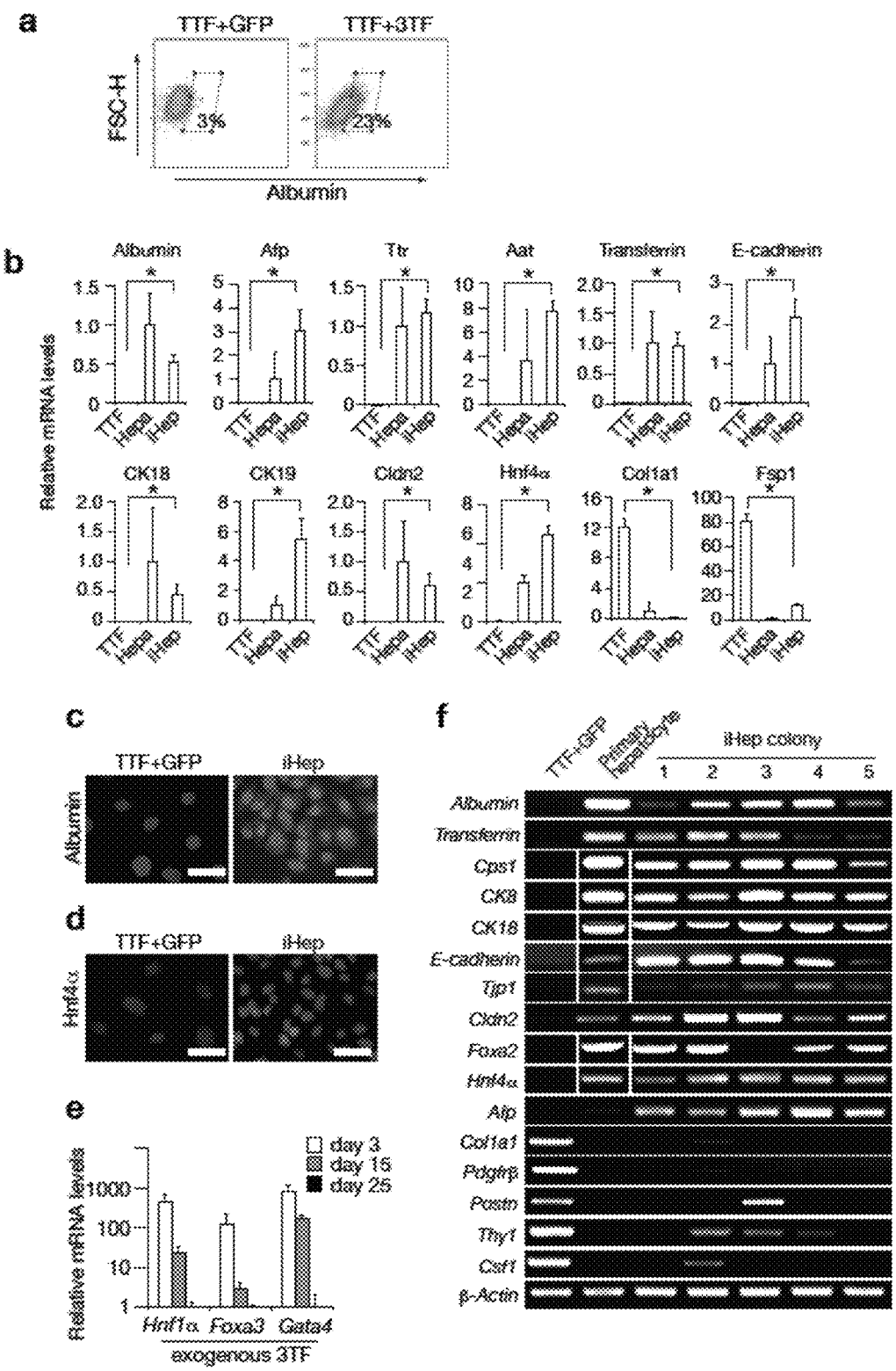
FIGs. 10a-f

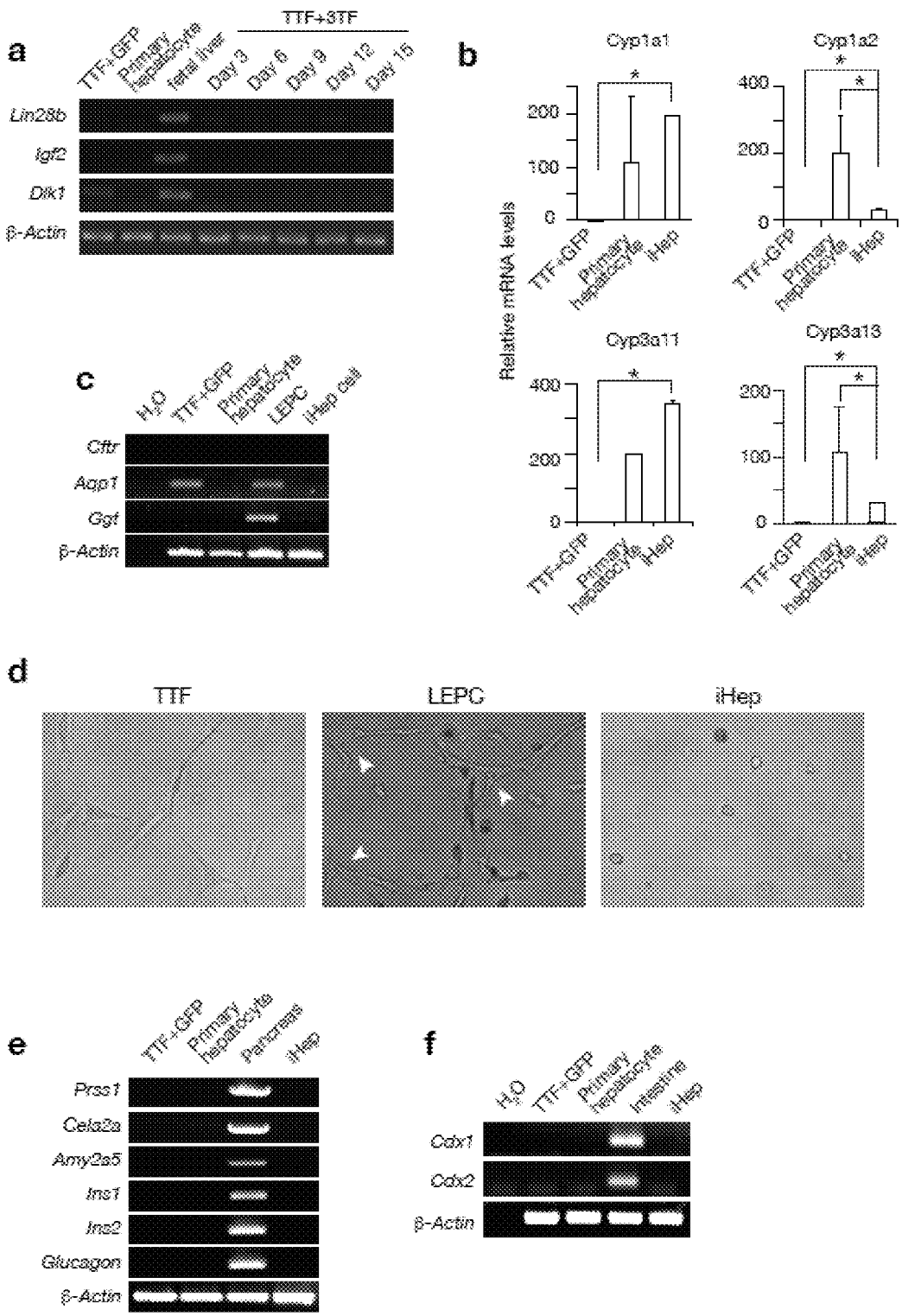
FIGs. 11a-f

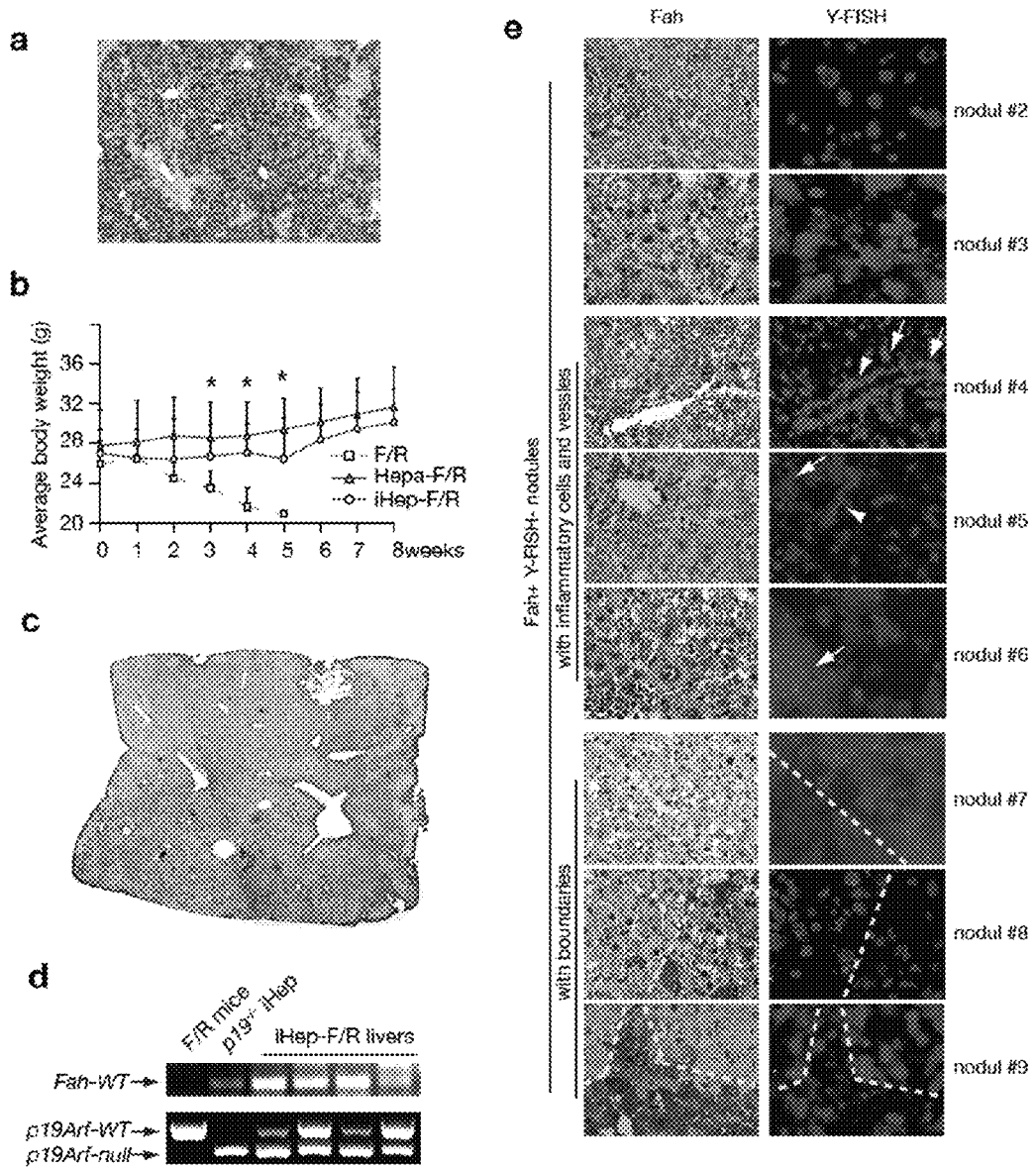
FIGs. 14a-e

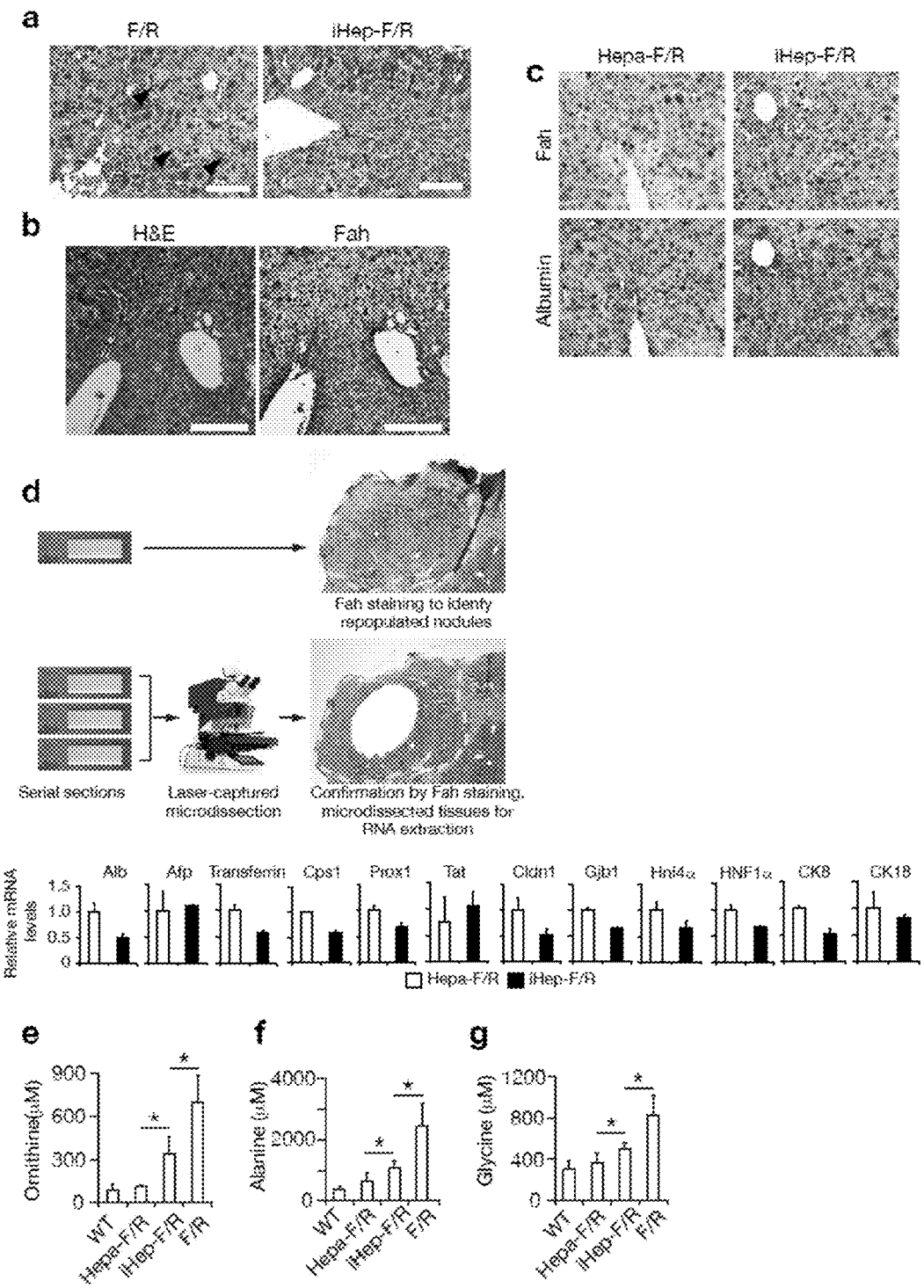
FIGs. 15a-g

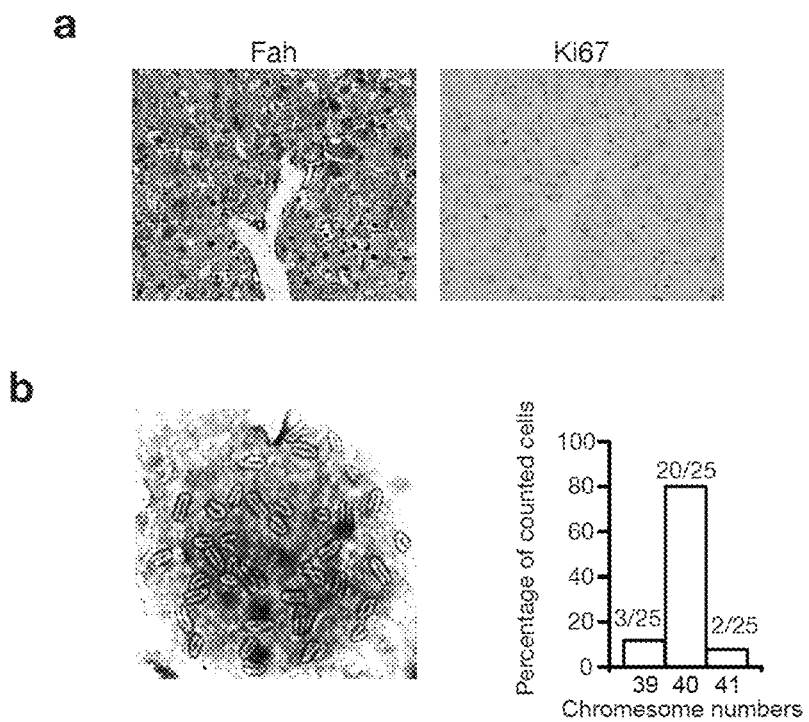
FIGs. 16 a and b
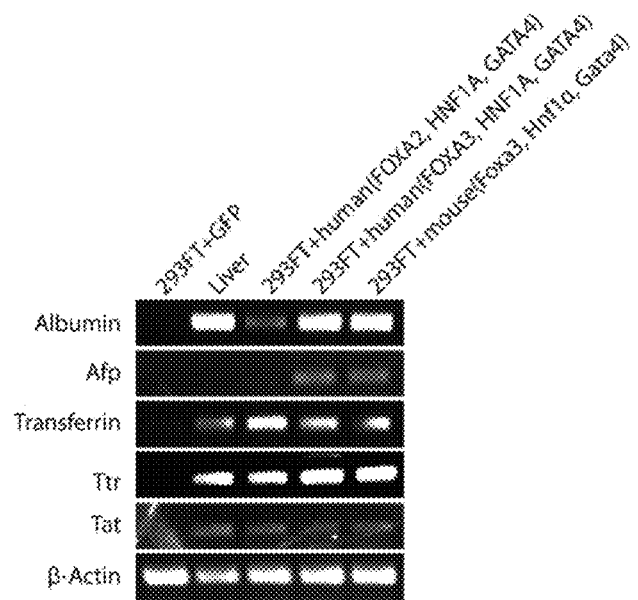
FIG. 17

A. 293FT+GFP
B. 293FT+human(FOXA2, HNF1A, GATA4)
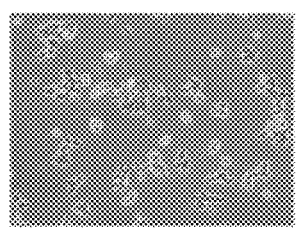
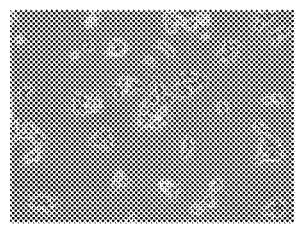
C. 293FT+human(FOXA3, HNF1A, GATA4)
D. 293FT+mouse(Foxa3, Hnf1a, Gata4)
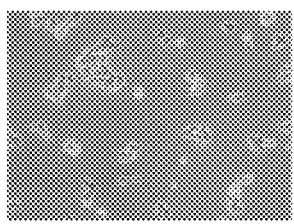
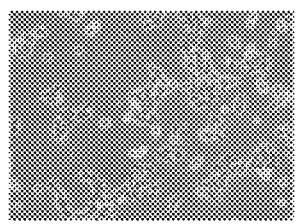
E.
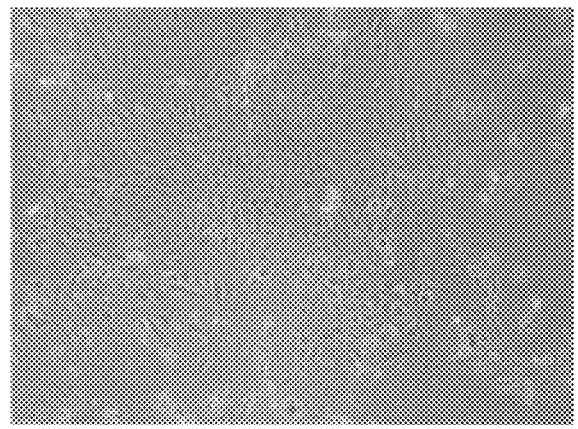
FIGs. 18 A-E
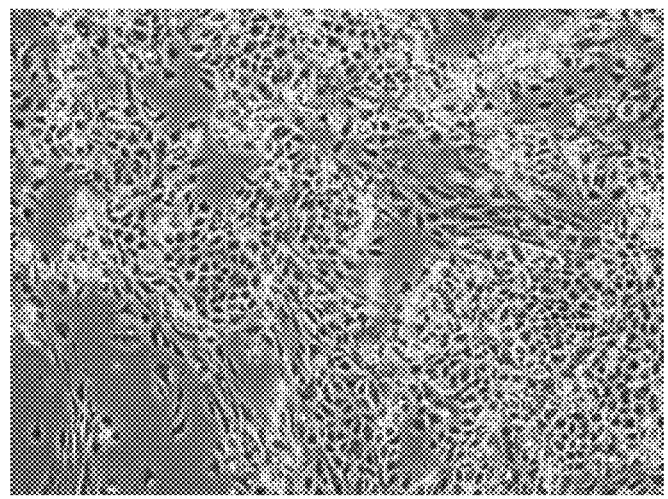
FIG. 19

SEQUENCE LISTING

```
<160> NUMBER OF SEQ ID NOS: 27

<210> SEQ ID NO 1
<211> LENGTH: 628
<212> TYPE: PRT
<213> ORGANISM: Mus musculus

<400> SEQUENCE: 1

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Met Val Gly Glu Gly Pro Leu Asp Lys Gly Glu
        35                  40                  45

Ser Cys Gly Gly Ser Arg Gly Asp Leu Thr Glu Leu Pro Asn Gly Leu
    50                  55                  60

Gly Glu Thr Arg Gly Ser Glu Asp Asp Thr Asp Asp Asp Gly Glu Asp
65                  70                  75                  80

Phe Ala Pro Pro Ile Leu Lys Glu Leu Glu Asn Leu Ser Pro Glu Glu
                85                  90                  95

Ala Ala His Gln Lys Ala Val Val Glu Ser Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255
```

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Asn Gly
        275                 280                 285

Pro Pro Pro Gly Pro Gly Pro Ala Leu Pro Ala His Ser Ser
    290                 295                 300

Pro Gly Leu Pro Thr Thr Leu Ser Pro Ser Lys Val His Gly Val
305                 310                 315                 320

Arg Tyr Gly Gln Ser Ala Thr Ser Glu Ala Ala Glu Val Pro Ser Ser
                325                 330                 335

Ser Gly Gly Pro Leu Val Thr Val Ser Ala Ala Leu His Gln Val Ser
            340                 345                 350

Pro Thr Gly Leu Glu Pro Ser Ser Leu Leu Ser Thr Glu Ala Lys Leu
        355                 360                 365

Val Ser Ala Thr Gly Gly Pro Leu Pro Pro Val Ser Thr Leu Thr Ala
    370                 375                 380

Leu His Ser Leu Glu Gln Thr Ser Pro Gly Leu Asn Gln Gln Pro Gln
385                 390                 395                 400

Asn Leu Ile Met Ala Ser Leu Pro Gly Val Met Thr Ile Gly Pro Gly
                405                 410                 415

Glu Pro Ala Ser Leu Gly Pro Thr Phe Thr Asn Thr Gly Ala Ser Thr
            420                 425                 430

Leu Val Ile Gly Leu Ala Ser Thr Gln Ala Gln Ser Val Pro Val Ile
        435                 440                 445

Asn Ser Met Gly Ser Ser Leu Thr Thr Leu Gln Pro Val Gln Phe Ser
    450                 455                 460

Gln Pro Leu His Pro Ser Tyr Gln Gln Pro Leu Met Pro Pro Val Gln
465                 470                 475                 480

Ser His Val Ala Gln Ser Pro Phe Met Ala Thr Met Ala Gln Leu Gln
                485                 490                 495

Ser Pro His Ala Leu Tyr Ser His Lys Pro Glu Val Ala Gln Tyr Thr
            500                 505                 510

His Thr Ser Leu Leu Pro Gln Thr Met Leu Ile Thr Asp Thr Asn Leu
        515                 520                 525

Ser Thr Leu Ala Ser Leu Thr Pro Thr Lys Gln Val Phe Thr Ser Asp
    530                 535                 540

Thr Glu Ala Ser Ser Glu Pro Gly Leu His Glu Pro Pro Ser Pro Ala
545                 550                 555                 560

Thr Thr Ile His Ile Pro Ser Gln Asp Pro Ser Asn Ile Gln His Leu
                565                 570                 575

Gln Pro Ala His Arg Leu Ser Thr Ser Pro Thr Val Ser Ser Ser Ser
            580                 585                 590

Leu Val Leu Tyr Gln Ser Ser Asp Ser Asn Gly His Ser His Leu Leu
        595                 600                 605

Pro Ser Asn His Ser Val Ile Glu Thr Phe Ile Ser Thr Gln Met Ala
    610                 615                 620

Ser Ser Ser Gln
625

<210> SEQ ID NO 2
<211> LENGTH: 353
<212> TYPE: PRT
<213> ORGANISM: Mus musculus

<400> SEQUENCE: 2

```
Met Leu Gly Ser Val Lys Met Glu Ala His Asp Leu Ala Glu Trp Ser
1               5                   10                  15

Tyr Tyr Pro Glu Ala Gly Glu Val Tyr Ser Pro Val Asn Pro Val Pro
            20                  25                  30

Thr Met Ala Pro Leu Asn Ser Tyr Met Thr Leu Asn Pro Leu Ser Ser
        35                  40                  45

Pro Tyr Pro Pro Gly Gly Leu Gln Ala Ser Pro Leu Pro Thr Gly Pro
    50                  55                  60

Leu Ala Pro Pro Ala Pro Thr Ala Pro Leu Gly Pro Thr Phe Pro Ser
65                  70                  75                  80

Leu Gly Thr Gly Gly Ser Thr Gly Gly Ser Ala Ser Gly Tyr Val Ala
                85                  90                  95

Pro Gly Pro Gly Leu Val His Gly Lys Glu Met Ala Lys Gly Tyr Arg
            100                 105                 110

Arg Pro Leu Ala His Ala Lys Pro Pro Tyr Ser Tyr Ile Ser Leu Ile
        115                 120                 125

Thr Met Ala Ile Gln Gln Ala Pro Gly Lys Met Leu Thr Leu Ser Glu
    130                 135                 140

Ile Tyr Gln Trp Ile Met Asp Leu Phe Pro Tyr Tyr Arg Glu Asn Gln
145                 150                 155                 160

Gln Arg Trp Gln Asn Ser Ile Arg His Ser Leu Ser Phe Asn Asp Cys
                165                 170                 175

Phe Val Lys Val Ala Arg Ser Pro Asp Lys Pro Gly Lys Gly Ser Tyr
            180                 185                 190

Trp Ala Leu His Pro Ser Ser Gly Asn Met Phe Glu Asn Gly Cys Tyr
        195                 200                 205

Leu Arg Arg Gln Lys Arg Phe Lys Leu Glu Glu Lys Ala Lys Lys Gly
    210                 215                 220

Asn Ser Ala Thr Ser Ala Ser Arg Asn Gly Thr Ala Gly Ser Ala Thr
225                 230                 235                 240

Ser Ala Thr Thr Thr Ala Ala Thr Ala Val Thr Ser Pro Ala Gln Pro
                245                 250                 255

Gln Pro Thr Pro Ser Glu Pro Glu Ala Gln Ser Gly Asp Asp Val Gly
            260                 265                 270

Gly Leu Asp Cys Ala Ser Pro Ser Ser Thr Pro Tyr Phe Ser Gly Leu
        275                 280                 285

Leu Glu Leu Pro Gly Glu Leu Lys Leu Asp Ala Pro Tyr Asn Phe Asn
    290                 295                 300

His Pro Phe Ser Ile Asn Asn Leu Met Ser Glu Gln Thr Ser Thr Pro
305                 310                 315                 320

Ser Lys Leu Asp Val Gly Phe Gly Gly Tyr Gly Ala Glu Ser Gly Glu
                325                 330                 335

Pro Gly Val Tyr Tyr Gln Ser Leu Tyr Ser Arg Ser Leu Leu Asn Ala
            340                 345                 350

Ser
```

<210> SEQ ID NO 3
<211> LENGTH: 441
<212> TYPE: PRT
<213> ORGANISM: Mus musculus

```
<400> SEQUENCE: 3

Met Tyr Gln Ser Leu Ala Met Ala Ala Asn His Gly Pro Pro Gly
1               5                   10                  15

Ala Tyr Glu Ala Gly Gly Pro Gly Ala Phe Met His Ser Ala Gly Ala
            20                  25                  30

Ala Ser Ser Pro Val Tyr Val Pro Thr Pro Arg Val Pro Ser Ser Val
                35                  40                  45

Leu Gly Leu Ser Tyr Leu Gln Gly Gly Ser Ala Ala Ala Gly
    50                  55                  60

Thr Thr Ser Gly Gly Ser Ser Gly Ala Gly Pro Ser Gly Ala Gly Pro
65              70                  75                  80

Gly Thr Gln Gln Gly Ser Pro Gly Trp Ser Gln Ala Gly Ala Glu Gly
                85                  90                  95

Ala Ala Tyr Thr Pro Pro Val Ser Pro Arg Phe Ser Phe Pro Gly
            100                 105                 110

Thr Thr Gly Ser Leu Ala Ala Ala Ala Ala Ala Ala Ala Arg Glu
            115                 120                 125

Ala Ala Ala Tyr Gly Ser Gly Gly Ala Ala Gly Ala Gly Leu Ala
    130                 135                 140

Gly Arg Glu Gln Tyr Gly Arg Pro Gly Phe Ala Gly Ser Tyr Ser Ser
145                 150                 155                 160

Pro Tyr Pro Ala Tyr Met Ala Asp Val Gly Ala Ser Trp Ala Ala Ala
                165                 170                 175

Ala Ala Ala Ser Ala Gly Pro Phe Asp Ser Pro Val Leu His Ser Leu
            180                 185                 190

Pro Gly Arg Ala Asn Pro Gly Arg His Pro Asn Leu Asp Met Phe Asp
    195                 200                 205

Asp Phe Ser Glu Gly Arg Glu Cys Val Asn Cys Gly Ala Met Ser Thr
210                 215                 220

Pro Leu Trp Arg Arg Asp Gly Thr Gly His Tyr Leu Cys Asn Ala Cys
225                 230                 235                 240

Gly Leu Tyr His Lys Met Asn Gly Ile Asn Arg Pro Leu Ile Lys Pro
                245                 250                 255

Gln Arg Arg Leu Ser Ala Ser Arg Arg Val Gly Leu Ser Cys Ala Asn
            260                 265                 270

Cys Gln Thr Thr Thr Thr Thr Leu Trp Arg Arg Asn Ala Glu Gly Glu
            275                 280                 285

Pro Val Cys Asn Ala Cys Gly Leu Tyr Met Lys Leu His Gly Val Pro
            290                 295                 300

Arg Pro Leu Ala Met Arg Lys Glu Gly Ile Gln Thr Arg Lys Arg Lys
305                 310                 315                 320

Pro Lys Asn Leu Asn Lys Ser Lys Thr Pro Ala Gly Pro Ala Gly Glu
                325                 330                 335

Thr Leu Pro Pro Ser Ser Gly Ala Ser Ser Gly Asn Ser Ser Asn Ala
            340                 345                 350

Thr Ser Ser Ser Ser Ser Glu Glu Met Arg Pro Ile Lys Thr Glu
            355                 360                 365

Pro Gly Leu Ser Ser His Tyr Gly His Ser Ser Met Ser Gln Thr
    370                 375                 380

Phe Ser Thr Val Ser Gly His Gly Pro Ser Ile His Pro Val Leu Ser
385                 390                 395                 400

Ala Leu Lys Leu Ser Pro Gln Gly Tyr Ala Ser Pro Val Thr Gln Thr
                405                 410                 415
```

```
Ser Gln Ala Ser Ser Lys Gln Asp Ser Trp Asn Ser Leu Val Leu Ala
            420                 425                 430

Asp Ser His Gly Asp Ile Ile Thr Ala
            435                 440

<210> SEQ ID NO 4
<211> LENGTH: 468
<212> TYPE: PRT
<213> ORGANISM: Mus musculus

<400> SEQUENCE: 4

Met Leu Gly Thr Val Lys Met Glu Gly His Glu Ser Asn Asp Trp Asn
1               5                   10                  15

Ser Tyr Tyr Ala Asp Thr Gln Glu Ala Tyr Ser Ser Val Pro Val Ser
                20                  25                  30

Asn Met Asn Ser Gly Leu Gly Ser Met Asn Ser Met Asn Thr Tyr Met
            35                  40                  45

Thr Met Asn Thr Met Thr Thr Ser Gly Asn Met Thr Pro Ala Ser Phe
    50                  55                  60

Asn Met Ser Tyr Ala Asn Thr Gly Leu Gly Ala Gly Leu Ser Pro Gly
65                  70                  75                  80

Ala Val Ala Gly Met Pro Gly Ala Ser Ala Gly Ala Met Asn Ser Met
                85                  90                  95

Thr Ala Ala Gly Val Thr Ala Met Gly Thr Ala Leu Ser Pro Gly Gly
            100                 105                 110

Met Gly Ser Met Gly Ala Gln Pro Ala Thr Ser Met Asn Gly Leu Gly
        115                 120                 125

Pro Tyr Ala Ala Ala Met Asn Pro Cys Met Ser Pro Met Ala Tyr Ala
    130                 135                 140

Pro Ser Asn Leu Gly Arg Ser Arg Ala Gly Gly Gly Asp Ala Lys
145                 150                 155                 160

Thr Phe Lys Arg Ser Tyr Pro His Ala Lys Pro Pro Tyr Ser Tyr Ile
                165                 170                 175

Ser Leu Ile Thr Met Ala Ile Gln Gln Ala Pro Ser Lys Met Leu Thr
            180                 185                 190

Leu Ser Glu Ile Tyr Gln Trp Ile Met Asp Leu Phe Pro Tyr Tyr Arg
        195                 200                 205

Gln Asn Gln Gln Arg Trp Gln Asn Ser Ile Arg His Ser Leu Ser Phe
    210                 215                 220

Asn Asp Cys Phe Val Lys Val Ala Arg Ser Pro Asp Lys Pro Gly Lys
225                 230                 235                 240

Gly Ser Tyr Trp Thr Leu His Pro Asp Ser Gly Asn Met Phe Glu Asn
                245                 250                 255

Gly Cys Tyr Leu Arg Arg Gln Lys Arg Phe Lys Cys Glu Lys Gln Pro
            260                 265                 270

Gly Ala Gly Gly Gly Ser Gly Gly Gly Ser Lys Gly Gly Pro Glu
        275                 280                 285

Ser Arg Lys Asp Pro Ser Gly Pro Gly Asn Pro Ser Ala Glu Ser Pro
    290                 295                 300

Leu His Arg Gly Val His Gly Lys Ala Ser Gln Leu Glu Gly Ala Pro
305                 310                 315                 320

Ala Pro Gly Pro Ala Ala Ser Pro Gln Thr Leu Asp His Ser Gly Ala
                325                 330                 335

Thr Ala Thr Gly Gly Ala Ser Glu Leu Lys Ser Pro Ala Ser Ser Ser
            340                 345                 350
```

-continued

```
Ala Pro Pro Ile Ser Ser Gly Pro Gly Ala Leu Ala Ser Val Pro Pro
            355                 360                 365

Ser His Pro Ala His Gly Leu Ala Pro His Glu Ser Gln Leu His Leu
    370                 375                 380

Lys Gly Asp Pro His Tyr Ser Phe Asn His Pro Phe Ser Ile Asn Asn
385                 390                 395                 400

Leu Met Ser Ser Glu Gln Gln His Lys Leu Asp Phe Lys Ala Tyr
                405                 410                 415

Glu Gln Ala Leu Gln Tyr Ser Pro Tyr Gly Ala Thr Leu Pro Ala Ser
            420                 425                 430

Leu Pro Leu Gly Ser Ala Ser Val Ala Thr Arg Ser Pro Ile Glu Pro
    435                 440                 445

Ser Ala Leu Glu Pro Ala Tyr Tyr Gln Gly Val Tyr Ser Arg Pro Val
    450                 455                 460

Leu Asn Thr Ser
465
```

<210> SEQ ID NO 5
<211> LENGTH: 459
<212> TYPE: PRT
<213> ORGANISM: Mus musculus

<400> SEQUENCE: 5

```
Met Leu Gly Ala Val Lys Met Glu Gly His Glu Pro Ser Asp Trp Ser
1               5                   10                  15

Ser Tyr Tyr Ala Glu Pro Glu Gly Tyr Ser Ser Val Ser Asn Met Asn
            20                  25                  30

Ala Gly Leu Gly Met Asn Gly Met Asn Thr Tyr Met Ser Met Ser Ala
        35                  40                  45

Ala Ala Met Gly Gly Gly Ser Gly Asn Met Ser Ala Gly Ser Met Asn
    50                  55                  60

Met Ser Ser Tyr Val Gly Ala Gly Met Ser Pro Ser Leu Ala Gly Met
65                  70                  75                  80

Ser Pro Gly Ala Gly Ala Met Ala Gly Met Ser Gly Ser Ala Gly Ala
            85                  90                  95

Ala Gly Val Ala Gly Met Gly Pro His Leu Ser Pro Ser Leu Ser Pro
        100                 105                 110

Leu Gly Gly Gln Ala Ala Gly Ala Met Gly Gly Leu Ala Pro Tyr Ala
    115                 120                 125

Asn Met Asn Ser Met Ser Pro Met Tyr Gly Gln Ala Gly Leu Ser Arg
130                 135                 140

Ala Arg Asp Pro Lys Thr Tyr Arg Arg Ser Tyr Thr His Ala Lys Pro
145                 150                 155                 160

Pro Tyr Ser Tyr Ile Ser Leu Ile Thr Met Ala Ile Gln Gln Ser Pro
            165                 170                 175

Asn Lys Met Leu Thr Leu Ser Glu Ile Tyr Gln Trp Ile Met Asp Leu
        180                 185                 190

Phe Pro Phe Tyr Arg Gln Asn Gln Gln Arg Trp Gln Asn Ser Ile Arg
    195                 200                 205

His Ser Leu Ser Phe Asn Asp Cys Phe Leu Lys Val Pro Arg Ser Pro
210                 215                 220

Asp Lys Pro Gly Lys Gly Ser Phe Trp Thr Leu His Pro Asp Ser Gly
225                 230                 235                 240

Asn Met Phe Glu Asn Gly Cys Tyr Leu Arg Arg Gln Lys Arg Phe Lys
            245                 250                 255
```

-continued

```
Cys Glu Lys Gln Leu Ala Leu Lys Glu Ala Ala Gly Ala Ala Ser Ser
            260                 265                 270

Gly Gly Lys Lys Thr Ala Pro Gly Ser Gln Ala Ser Gln Ala Gln Leu
        275                 280                 285

Gly Glu Ala Ala Gly Ser Ala Ser Glu Thr Pro Ala Gly Thr Glu Ser
    290                 295                 300

Pro His Ser Ser Ala Ser Pro Cys Gln Glu His Lys Arg Gly Gly Leu
305                 310                 315                 320

Ser Glu Leu Lys Gly Ala Pro Ala Ser Ala Leu Ser Pro Pro Glu Pro
                325                 330                 335

Ala Pro Ser Pro Gly Gln Gln Gln Ala Ala His Leu Leu Gly
            340                 345                 350

Pro Pro His His Pro Gly Leu Pro Pro Glu Ala His Leu Lys Pro Glu
        355                 360                 365

His His Tyr Ala Phe Asn His Pro Phe Ser Ile Asn Asn Leu Met Ser
    370                 375                 380

Ser Glu Gln Gln His His Ser His His His Gln Pro His Lys
385                 390                 395                 400

Met Asp Leu Lys Ala Tyr Glu Gln Val Met His Tyr Pro Gly Gly Tyr
                405                 410                 415

Gly Ser Pro Met Pro Gly Ser Leu Ala Met Gly Pro Val Thr Asn Lys
            420                 425                 430

Ala Gly Leu Asp Ala Ser Pro Leu Ala Ala Asp Thr Ser Tyr Tyr Gln
        435                 440                 445

Gly Val Tyr Ser Arg Pro Ile Met Asn Ser Ser
    450                 455

<210> SEQ ID NO 6
<211> LENGTH: 474
<212> TYPE: PRT
<213> ORGANISM: Mus musculus

<400> SEQUENCE: 6

Met Arg Leu Ser Lys Thr Leu Ala Gly Met Asp Met Ala Asp Tyr Ser
1               5                   10                  15

Ala Ala Leu Asp Pro Ala Tyr Thr Thr Leu Glu Phe Glu Asn Val Gln
                20                  25                  30

Val Leu Thr Met Gly Asn Asp Thr Ser Pro Ser Glu Gly Ala Asn Leu
            35                  40                  45

Asn Ser Ser Asn Ser Leu Gly Val Ser Ala Leu Cys Ala Ile Cys Gly
        50                  55                  60

Asp Arg Ala Thr Gly Lys His Tyr Gly Ala Ser Ser Cys Asp Gly Cys
65                  70                  75                  80

Lys Gly Phe Phe Arg Arg Ser Val Arg Lys Asn His Met Tyr Ser Cys
                85                  90                  95

Arg Phe Ser Arg Gln Cys Val Val Asp Lys Asp Lys Arg Asn Gln Cys
            100                 105                 110

Arg Tyr Cys Arg Leu Lys Lys Cys Phe Arg Ala Gly Met Lys Lys Glu
        115                 120                 125

Ala Val Gln Asn Glu Arg Asp Arg Ile Ser Thr Arg Arg Ser Ser Tyr
    130                 135                 140

Glu Asp Ser Ser Leu Pro Ser Ile Asn Ala Leu Leu Gln Ala Glu Val
145                 150                 155                 160

Leu Ser Gln Gln Ile Thr Ser Pro Ile Ser Gly Ile Asn Gly Asp Ile
                165                 170                 175
```

```
Arg Ala Lys Lys Ile Ala Asn Ile Thr Asp Val Cys Glu Ser Met Lys
                180                 185                 190

Glu Gln Leu Leu Val Leu Val Glu Trp Ala Lys Tyr Ile Pro Ala Phe
            195                 200                 205

Cys Glu Leu Leu Leu Asp Asp Gln Val Ala Leu Leu Arg Ala His Ala
        210                 215                 220

Gly Glu His Leu Leu Leu Gly Ala Thr Lys Arg Ser Met Val Phe Lys
225                 230                 235                 240

Asp Val Leu Leu Leu Gly Asn Asp Tyr Ile Val Pro Arg His Cys Pro
                245                 250                 255

Glu Leu Ala Glu Met Ser Arg Val Ser Ile Arg Ile Leu Asp Glu Leu
            260                 265                 270

Val Leu Pro Phe Gln Glu Leu Gln Ile Asp Asp Asn Glu Tyr Ala Cys
        275                 280                 285

Leu Lys Ala Ile Ile Phe Phe Asp Pro Asp Ala Lys Gly Leu Ser Asp
    290                 295                 300

Pro Gly Lys Ile Lys Arg Leu Arg Ser Gln Val Gln Val Ser Leu Glu
305                 310                 315                 320

Asp Tyr Ile Asn Asp Arg Gln Tyr Asp Ser Arg Gly Arg Phe Gly Glu
                325                 330                 335

Leu Leu Leu Leu Leu Pro Thr Leu Gln Ser Ile Thr Trp Gln Met Ile
            340                 345                 350

Glu Gln Ile Gln Phe Ile Lys Leu Phe Gly Met Ala Lys Ile Asp Asn
        355                 360                 365

Leu Leu Gln Glu Met Leu Leu Gly Gly Ser Ala Ser Asp Ala Pro His
    370                 375                 380

Thr His His Pro Leu His Pro His Leu Met Gln Glu His Met Gly Thr
385                 390                 395                 400

Asn Val Ile Val Ala Asn Thr Met Pro Ser His Leu Ser Asn Gly Gln
                405                 410                 415

Met Cys Glu Trp Pro Arg Pro Arg Gly Gln Ala Ala Thr Pro Glu Thr
            420                 425                 430

Pro Gln Pro Ser Pro Pro Ser Gly Ser Gly Ser Glu Ser Tyr Lys Leu
        435                 440                 445

Leu Pro Gly Ala Ile Thr Thr Ile Val Lys Pro Pro Ser Ala Ile Pro
    450                 455                 460

Gln Pro Thr Ile Thr Lys Gln Glu Ala Ile
465                 470

<210> SEQ ID NO 7
<211> LENGTH: 465
<212> TYPE: PRT
<213> ORGANISM: Mus musculus

<400> SEQUENCE: 7

Met Asn Ala Gln Leu Thr Met Glu Ala Ile Gly Glu Leu His Gly Val
1               5                   10                  15

Ser His Glu Pro Val Pro Ala Pro Ala Asp Leu Leu Gly Gly Ser Pro
                20                  25                  30

His Ala Arg Ser Ser Val Gly Arg Gly Ser His Leu Pro Pro Ala
            35                  40                  45

His Pro Arg Ser Met Gly Met Ala Ser Leu Leu Asp Gly Gly Ser Gly
        50                  55                  60

Gly Ser Asp Tyr His His His His Arg Ala Pro Glu His Ser Leu Ala
65                  70                  75                  80
```

```
Gly Pro Leu His Pro Thr Met Thr Met Ala Cys Glu Thr Pro Pro Gly
             85                  90                  95

Met Ser Met Pro Thr Thr Tyr Thr Thr Leu Thr Pro Leu Gln Pro Leu
            100                 105                 110

Pro Pro Ile Ser Thr Val Ser Asp Lys Phe Pro His His His His
            115                 120                 125

His His His His His His Pro His His His Gln Arg Leu Ala Gly Asn
        130                 135                 140

Val Ser Gly Ser Phe Thr Leu Met Arg Asp Glu Arg Gly Leu Ala Ser
145                 150                 155                 160

Met Asn Asn Leu Tyr Thr Pro Tyr His Lys Asp Val Ala Gly Met Gly
                165                 170                 175

Gln Ser Leu Ser Pro Leu Ser Gly Ser Gly Leu Gly Ser Ile His Asn
            180                 185                 190

Ser Gln Gln Gly Leu Pro His Tyr Ala His Pro Gly Ala Ala Met Pro
        195                 200                 205

Thr Asp Lys Met Leu Thr Pro Asn Gly Phe Glu Ala His His Pro Ala
    210                 215                 220

Met Leu Gly Arg His Gly Glu Gln His Leu Thr Pro Thr Ser Ala Gly
225                 230                 235                 240

Met Val Pro Ile Asn Gly Leu Pro Pro His His Pro His Ala His Leu
                245                 250                 255

Asn Ala Gln Gly His Gly Gln Leu Leu Gly Thr Ala Arg Glu Pro Asn
            260                 265                 270

Pro Ser Val Thr Gly Ala Gln Val Ser Asn Gly Ser Asn Ser Gly Gln
        275                 280                 285

Met Glu Glu Ile Asn Thr Lys Glu Val Ala Gln Arg Ile Thr Thr Glu
    290                 295                 300

Leu Lys Arg Tyr Ser Ile Pro Gln Ala Ile Phe Ala Gln Arg Val Leu
305                 310                 315                 320

Cys Arg Ser Gln Gly Thr Leu Ser Asp Leu Leu Arg Asn Pro Lys Pro
                325                 330                 335

Trp Ser Lys Leu Lys Ser Gly Arg Glu Thr Phe Arg Arg Met Trp Lys
            340                 345                 350

Trp Leu Gln Glu Pro Glu Phe Gln Arg Met Ser Ala Leu Arg Leu Ala
        355                 360                 365

Ala Cys Lys Arg Lys Glu Gln Glu His Gly Lys Asp Arg Gly Asn Thr
    370                 375                 380

Pro Lys Lys Pro Arg Leu Val Phe Thr Asp Val Gln Arg Arg Thr Leu
385                 390                 395                 400

His Ala Ile Phe Lys Glu Asn Lys Arg Pro Ser Lys Glu Leu Gln Ile
                405                 410                 415

Thr Ile Ser Gln Gln Leu Gly Leu Glu Leu Ser Thr Val Ser Asn Phe
            420                 425                 430

Phe Met Asn Ala Arg Arg Arg Ser Leu Asp Lys Trp Gln Asp Glu Gly
        435                 440                 445

Gly Ser Asn Ser Gly Ser Ser Ser Ser Ser Ser Thr Cys Thr Lys
    450                 455                 460

Ala
465
```

```
<210> SEQ ID NO 8
<211> LENGTH: 295
<212> TYPE: PRT
<213> ORGANISM: Mus musculus

<400> SEQUENCE: 8

Met Glu Lys Met Ser Arg Gln Leu Pro Leu Asn Pro Thr Phe Ile Pro
1               5                   10                  15

Pro Pro Tyr Gly Val Leu Arg Ser Leu Leu Glu Asn Pro Leu Lys Leu
            20                  25                  30

Pro Leu His Pro Glu Asp Ala Phe Ser Lys Glu Lys Asp Lys Gly Lys
        35                  40                  45

Lys Leu Asp Asp Glu Ser Ser Ser Pro Thr Val Pro Gln Ser Ala Phe
50                  55                  60

Leu Gly Pro Thr Leu Trp Asp Lys Thr Leu Pro Tyr Asp Gly Asp Thr
65                  70                  75                  80

Phe Gln Leu Glu Tyr Met Asp Leu Glu Glu Phe Leu Ser Glu Asn Gly
                85                  90                  95

Ile Pro Pro Ser Pro Ser Gln His Asp His Ser Pro His Pro Pro Gly
            100                 105                 110

Leu Gln Pro Ala Ser Ser Thr Ala Pro Ser Val Met Asp Leu Ser Ser
        115                 120                 125

Arg Ala Thr Ala Pro Leu His Pro Gly Ile Pro Ser Pro Asn Cys Met
130                 135                 140

Gln Ser Pro Ile Arg Pro Gly Gln Leu Leu Pro Ala Asn Arg Asn Thr
145                 150                 155                 160

Pro Ser Pro Ile Asp Pro Asp Thr Ile Gln Val Pro Val Gly Tyr Glu
                165                 170                 175

Pro Asp Pro Ala Asp Leu Ala Leu Ser Ser Ile Pro Gly Gln Glu Met
            180                 185                 190

Phe Asp Pro Arg Lys Arg Lys Phe Ser Glu Glu Glu Leu Lys Pro Gln
        195                 200                 205

Pro Met Ile Lys Lys Ala Arg Lys Val Phe Ile Pro Asp Asp Leu Lys
210                 215                 220

Asp Asp Lys Tyr Trp Ala Arg Arg Arg Lys Asn Asn Met Ala Ala Lys
225                 230                 235                 240

Arg Ser Arg Asp Ala Arg Arg Leu Lys Glu Asn Gln Ile Ala Ile Arg
                245                 250                 255

Ala Ser Phe Leu Glu Lys Glu Asn Ser Ala Leu Arg Gln Glu Val Ala
            260                 265                 270

Asp Leu Arg Lys Glu Leu Gly Lys Cys Lys Asn Ile Leu Ala Lys Tyr
        275                 280                 285

Glu Ala Arg His Gly Pro Leu
        290                 295

<210> SEQ ID NO 9
<211> LENGTH: 271
<212> TYPE: PRT
<213> ORGANISM: Mus musculus

<400> SEQUENCE: 9

Met Gln Phe Pro His Pro Gly Pro Ala Ala Ala Pro Ala Val Gly Val
1               5                   10                  15

Pro Leu Tyr Ala Pro Thr Pro Leu Leu Gln Pro Ala His Pro Thr Pro
            20                  25                  30
```

```
Phe Tyr Ile Asp Asp Ile Leu Gly Arg Gly Pro Ala Pro Thr Pro
             35                  40                  45

Thr Pro Thr Leu Pro Ser Pro Asn Ser Ser Phe Thr Ser Leu Val Ser
 50                  55                  60

Ser Tyr Arg Thr Pro Val Tyr Glu Pro Thr Pro Val His Pro Ala Phe
 65                  70                  75                  80

Ser His His Pro Ala Ala Ala Leu Ala Ala Ala Tyr Gly Pro Ser Gly
                 85                  90                  95

Phe Gly Gly Pro Leu Tyr Pro Phe Pro Arg Thr Val Asn Asp Tyr Thr
                100                 105                 110

His Ala Leu Leu Arg His Asp Pro Leu Gly Lys Pro Leu Leu Trp Ser
            115                 120                 125

Pro Phe Leu Gln Arg Pro Leu His Lys Arg Lys Gly Gly Gln Val Arg
130                 135                 140

Phe Ser Asn Asp Gln Thr Val Glu Leu Glu Lys Lys Phe Glu Thr Gln
145                 150                 155                 160

Lys Tyr Leu Ser Pro Pro Glu Arg Lys Arg Leu Ala Lys Met Leu Gln
                165                 170                 175

Leu Ser Glu Arg Gln Val Lys Thr Trp Phe Gln Asn Arg Arg Ala Lys
            180                 185                 190

Trp Arg Arg Leu Lys Gln Glu Asn Pro Gln Ser Asn Lys Lys Asp Ala
        195                 200                 205

Leu Asp Ser Leu Asp Thr Ser Cys Glu Gln Gly Gln Asp Leu Pro Ser
    210                 215                 220

Glu Gln Asn Lys Gly Ala Ser Leu Asp Arg Ser Gln Cys Ser Pro Ser
225                 230                 235                 240

Pro Ala Ser Gln Glu Asp Pro Asp Ser Glu Ile Ser Glu Asp Ser Asp
                245                 250                 255

Gln Glu Val Asp Ile Glu Gly Asp Lys Gly Tyr Phe Asn Ala Gly
            260                 265                 270

<210> SEQ ID NO 10
<211> LENGTH: 1234
<212> TYPE: PRT
<213> ORGANISM: Mus musculus

<400> SEQUENCE: 10

Met Ser Lys Glu Arg Pro Lys Arg Asn Ile Ile Gln Lys Lys Tyr Asp
 1               5                  10                  15

Asp Ser Asp Gly Ile Pro Trp Ser Glu Glu Arg Val Val Arg Lys Val
                20                  25                  30

Leu Tyr Leu Ser Leu Lys Glu Phe Lys Asn Ala Gln Lys Arg Gln His
             35                  40                  45

Gly Glu Gly Leu Ala Gly Ser Leu Lys Ala Val Asn Gly Leu Leu Gly
 50                  55                  60

Asn Ala Gln Ala Lys Ala Leu Gly Pro Ala Ser Glu Gln Ser Glu Asn
 65                  70                  75                  80

Glu Lys Asp Asp Ala Ser Gln Val Ser Ser Thr Ser Asn Asp Val Ser
                 85                  90                  95

Ser Ser Asp Phe Glu Glu Gly Pro Ser Arg Lys Arg Pro Arg Leu Gln
                100                 105                 110

Ala Gln Arg Lys Phe Ala Gln Ser Gln Pro Asn Ser Pro Ser Thr Thr
            115                 120                 125

Pro Val Lys Ile Val Glu Pro Leu Leu Pro Pro Ala Thr Gln Ile
130                 135                 140
```

```
Ser Asp Leu Ser Lys Arg Lys Pro Lys Thr Glu Asp Phe Leu Thr Phe
145                 150                 155                 160

Leu Cys Leu Arg Gly Ser Pro Ala Leu Pro Asn Ser Met Val Tyr Phe
            165                 170                 175

Gly Ser Ser Gln Asp Glu Glu Asp Val Glu Glu Glu Asp Asp Glu Thr
            180                 185                 190

Glu Asp Val Lys Ala Thr Thr Asn Asn Ala Ser Ser Ser Cys Gln Ser
            195                 200                 205

Thr Pro Arg Lys Gly Lys Thr His Lys His Val His Asn Gly His Val
            210                 215                 220

Phe Asn Gly Ser Ser Arg Ser Ala Arg Glu Lys Glu Pro Ala His Lys
225                 230                 235                 240

His Arg Ser Lys Glu Ala Thr Pro Gly Lys Glu Lys His Ser Glu Pro
            245                 250                 255

Arg Ala Asp Ser Arg Arg Glu Gln Ala Ser Gly Ala Gln Pro Thr Ala
            260                 265                 270

Ala Ser Ala Ala Ala Ser Ser Ala Lys Gly Leu Ala Ala Asn His Gln
            275                 280                 285

Pro Pro Pro Ser His Arg Ser Ala Gln Asp Leu Arg Lys Gln Val Ser
290                 295                 300

Lys Val Asn Gly Val Thr Arg Met Ser Ser Leu Gly Ala Gly Thr Asn
305                 310                 315                 320

Ser Ala Lys Lys Ile Arg Glu Val Arg Pro Ser Pro Ser Lys Thr Val
            325                 330                 335

Lys Tyr Thr Ala Thr Val Thr Lys Gly Thr Val Thr Tyr Thr Lys Ala
            340                 345                 350

Lys Arg Glu Leu Val Lys Glu Thr Lys Pro Asn His His Lys Pro Ser
            355                 360                 365

Ser Ala Val Asn His Thr Ile Ser Gly Lys Thr Glu Ser Ser Asn Ala
            370                 375                 380

Lys Thr Arg Lys Gln Val Leu Ser Leu Gly Gly Ala Ser Lys Ser Thr
385                 390                 395                 400

Gly Pro Ala Ala Ser Gly Leu Lys Ala Ser Ser Arg Leu Asn Pro Lys
            405                 410                 415

Ser Cys Thr Lys Glu Val Gly Gly Arg Gln Leu Arg Glu Gly Leu Arg
            420                 425                 430

Asn Ser Lys Arg Arg Leu Glu Glu Ala Gln Gln Val Asp Lys Pro Gln
            435                 440                 445

Ser Pro Pro Lys Lys Met Lys Gly Val Ala Gly Asn Ala Glu Ala Pro
450                 455                 460

Gly Lys Lys Ala Ser Ala Ala Ser Gly Glu Lys Ser Leu Leu Asn Gly
465                 470                 475                 480

His Val Lys Lys Glu Val Pro Glu Arg Ser Leu Glu Arg Asn Arg Pro
            485                 490                 495

Lys Arg Ala Ala Ala Gly Lys Asn Met Leu Gly Lys Gln Ala His Gly
            500                 505                 510

Lys Thr Glu Gly Thr Pro Cys Glu Asn Arg Ser Thr Ser Gln Pro Glu
            515                 520                 525

Ser Ser His Lys Pro His Asp Pro Gln Gly Lys Pro Glu Lys Gly Ser
            530                 535                 540

Gly Lys Ser Gly Trp Ala Ala Met Asp Glu Ile Pro Val Leu Arg Pro
545                 550                 555                 560
```

-continued

```
Ser Ala Lys Glu Phe His Asp Pro Leu Ile Tyr Ile Glu Ser Val Arg
            565                 570                 575
Ala Gln Val Glu Lys Tyr Gly Met Cys Arg Val Ile Pro Pro Pro Asp
        580                 585                 590
Trp Arg Pro Glu Cys Lys Leu Asn Asp Glu Met Arg Phe Val Thr Gln
    595                 600                 605
Ile Gln His Ile His Lys Leu Gly Arg Arg Trp Gly Pro Asn Val Gln
610                 615                 620
Arg Leu Ala Cys Ile Lys Lys His Leu Arg Ser Gln Gly Ile Thr Met
625                 630                 635                 640
Asp Glu Leu Pro Leu Ile Gly Gly Cys Glu Leu Asp Leu Ala Cys Phe
                645                 650                 655
Phe Arg Leu Ile Asn Glu Met Gly Gly Met Gln Gln Val Thr Asp Leu
            660                 665                 670
Lys Lys Trp Asn Lys Leu Ala Asp Met Leu Arg Ile Pro Lys Thr Ala
        675                 680                 685
Gln Asp Arg Leu Ala Lys Leu Gln Glu Ala Tyr Cys Gln Tyr Leu Leu
    690                 695                 700
Ser Tyr Asp Ser Leu Ser Pro Glu Glu His Arg Arg Leu Glu Lys Glu
705                 710                 715                 720
Val Leu Met Glu Lys Glu Ile Leu Glu Lys Arg Lys Gly Pro Leu Glu
                725                 730                 735
Gly His Thr Glu Ser Asp His His Lys Phe His Ser Leu Pro Arg Phe
            740                 745                 750
Glu Pro Lys Asn Gly Leu Val His Gly Val Thr Pro Arg Asn Gly Phe
        755                 760                 765
Arg Ser Lys Leu Lys Glu Val Gly Arg Ala Pro Leu Lys Thr Gly Arg
    770                 775                 780
Arg Arg Leu Phe Ala Gln Glu Lys Glu Val Val Lys Glu Glu Glu
785                 790                 795                 800
Asp Lys Gly Val Leu Asn Asp Phe His Lys Cys Ile Tyr Lys Gly Arg
                805                 810                 815
Ser Val Ser Leu Thr Thr Phe Tyr Arg Thr Ala Arg Asn Ile Met Asn
            820                 825                 830
Met Cys Phe Ser Lys Glu Pro Ala Pro Ala Glu Ile Glu Gln Glu Tyr
        835                 840                 845
Trp Arg Leu Val Glu Glu Lys Cys His Val Ala Val His Cys Gly
    850                 855                 860
Lys Val Asp Thr Asn Thr His Gly Ser Gly Phe Pro Val Gly Lys Ser
865                 870                 875                 880
Glu Pro Phe Ser Arg His Gly Trp Asn Leu Thr Val Leu Pro Asn Asn
                885                 890                 895
Thr Gly Ser Ile Leu Arg His Leu Gly Ala Val Pro Gly Val Thr Ile
            900                 905                 910
Pro Trp Leu Asn Ile Gly Met Val Phe Ser Thr Ser Cys Trp Ser Arg
        915                 920                 925
Asp Gln Asn His Leu Pro Tyr Ile Asp Tyr Leu His Thr Gly Ala Asp
    930                 935                 940
Cys Ile Trp Tyr Cys Ile Pro Ala Glu Glu Asn Lys Leu Glu Asp
945                 950                 955                 960
Val Val His Thr Leu Leu Gln Gly Asn Gly Thr Pro Gly Leu Gln Met
                965                 970                 975
```

```
Leu Glu Ser Asn Val Met Ile Ser Pro Glu Val Leu Cys Lys Lys Gly
            980                 985                 990

Ile Lys Val His Arg Thr Val Gln Gln Ser Gly Gln Phe Val Val Cys
        995                1000                1005

Phe Pro Gly Ser Phe Val Ser Lys Val Cys Cys Gly Tyr Asn Val
   1010                1015                1020

Ser Glu Thr Val His Phe Ala Thr Thr Gln Trp Thr Ser Met Gly
   1025                1030                1035

Phe Glu Thr Ala Lys Glu Met Lys Arg Arg His Ile Ala Lys Pro
   1040                1045                1050

Phe Ser Met Glu Lys Leu Leu Tyr Gln Ile Ala Gln Ala Glu Ala
   1055                1060                1065

Lys Lys Glu Asn Gly Pro Thr Leu Ser Thr Ile Ser Ala Leu Leu
   1070                1075                1080

Asp Glu Leu Arg Asp Thr Glu Leu Arg Gln Arg Leu Leu Phe
   1085                1090                1095

Glu Ala Gly Leu His Ser Ser Ala Arg Tyr Gly Ser His Asp Gly
   1100                1105                1110

Asn Ser Thr Val Ala Asp Gly Lys Lys Lys Pro Arg Lys Trp Leu
   1115                1120                1125

Gln Leu Glu Thr Ser Glu Arg Arg Cys Gln Ile Cys Gln His Leu
   1130                1135                1140

Cys Tyr Leu Ser Met Val Val Gln Glu Asn Glu Asn Val Val Phe
   1145                1150                1155

Cys Leu Glu Cys Ala Leu Arg His Val Glu Lys Gln Lys Ser Cys
   1160                1165                1170

Arg Gly Leu Lys Leu Met Tyr Arg Tyr Asp Glu Glu Gln Ile Ile
   1175                1180                1185

Ser Leu Val Asn Gln Ile Cys Gly Lys Val Ser Gly Lys His Gly
   1190                1195                1200

Gly Ile Glu Asn Cys Leu Asn Lys Pro Thr Pro Lys Arg Gly Pro
   1205                1210                1215

Arg Lys Arg Ala Thr Val Asp Val Pro Pro Ser Arg Leu Pro Ser
   1220                1225                1230

Ser

<210> SEQ ID NO 11
<211> LENGTH: 420
<212> TYPE: PRT
<213> ORGANISM: Mus musculus

<400> SEQUENCE: 11

Met Ala Met Val Val Ser Ser Trp Arg Asp Pro Gln Asp Asp Val Ala
 1               5                  10                  15

Gly Gly Asn Pro Gly Gly Pro Asn Pro Ala Ala Gln Ala Ala Arg Gly
            20                  25                  30

Gly Gly Gly Gly Glu Gln Gln Gln Ala Gly Ser Gly Ala Pro His Thr
        35                  40                  45

Pro Gln Thr Pro Gly Gln Pro Gly Ala Pro Ala Thr Pro Gly Thr Ala
    50                  55                  60

Gly Asp Lys Gly Gln Gly Pro Pro Gly Ser Gly Gln Ser Gln Gln His
65                  70                  75                  80

Ile Glu Cys Val Val Cys Gly Asp Lys Ser Ser Gly Lys His Tyr Gly
                85                  90                  95
```

-continued

```
Gln Phe Thr Cys Glu Gly Cys Lys Ser Phe Lys Arg Ser Val Arg
                100                 105                 110

Arg Asn Leu Thr Tyr Thr Cys Arg Ala Asn Arg Asn Cys Pro Ile Asp
        115                 120                 125

Gln His His Arg Asn Gln Cys Gln Tyr Cys Arg Leu Lys Lys Cys Leu
    130                 135                 140

Lys Val Gly Met Arg Arg Glu Ala Val Gln Arg Gly Arg Met Pro Pro
145                 150                 155                 160

Thr Gln Pro Asn Pro Gly Gln Tyr Ala Leu Thr Asn Gly Asp Pro Leu
                165                 170                 175

Asn Gly His Cys Tyr Leu Ser Gly Tyr Ile Ser Leu Leu Leu Arg Ala
            180                 185                 190

Glu Pro Tyr Pro Thr Ser Arg Tyr Gly Ser Gln Cys Met Gln Pro Asn
        195                 200                 205

Asn Ile Met Gly Ile Glu Asn Ile Cys Glu Leu Ala Ala Arg Leu Leu
    210                 215                 220

Phe Ser Ala Val Glu Trp Ala Arg Asn Ile Pro Phe Phe Pro Asp Leu
225                 230                 235                 240

Gln Ile Thr Asp Gln Val Ser Leu Leu Arg Leu Thr Trp Ser Glu Leu
                245                 250                 255

Phe Val Leu Asn Ala Ala Gln Cys Ser Met Pro Leu His Val Ala Pro
            260                 265                 270

Leu Leu Ala Ala Ala Gly Leu His Ala Ser Pro Met Ser Ala Asp Arg
        275                 280                 285

Val Val Ala Phe Met Asp His Ile Arg Ile Phe Gln Glu Gln Val Glu
    290                 295                 300

Lys Leu Lys Ala Leu His Val Asp Ser Ala Glu Tyr Ser Cys Leu Lys
305                 310                 315                 320

Ala Ile Val Leu Phe Thr Ser Asp Ala Cys Gly Leu Ser Asp Ala Ala
                325                 330                 335

His Ile Glu Ser Leu Gln Glu Lys Ser Gln Cys Ala Leu Glu Glu Tyr
            340                 345                 350

Val Arg Ser Gln Tyr Pro Asn Gln Pro Ser Arg Phe Gly Lys Leu Leu
        355                 360                 365

Leu Arg Leu Pro Ser Leu Arg Thr Val Ser Ser Ser Val Ile Glu Gln
    370                 375                 380

Leu Phe Phe Val Arg Leu Val Gly Lys Thr Pro Ile Glu Thr Leu Ile
385                 390                 395                 400

Arg Asp Met Leu Leu Ser Gly Ser Ser Phe Asn Trp Pro Tyr Met Ser
                405                 410                 415

Ile Gln Cys Ser
        420

<210> SEQ ID NO 12
<211> LENGTH: 560
<212> TYPE: PRT
<213> ORGANISM: Mus musculus

<400> SEQUENCE: 12

Met Ser Ala Ser Leu Asp Thr Gly Asp Phe Gln Glu Phe Leu Lys His
1               5                   10                  15

Gly Leu Thr Ala Ile Ala Ser Ala Pro Gly Ser Glu Thr Arg His Ser
            20                  25                  30

Pro Lys Arg Glu Glu Gln Leu Arg Glu Lys Arg Ala Gly Leu Pro Asp
        35                  40                  45
```

```
Arg His Arg Arg Pro Ile Pro Ala Arg Ser Arg Leu Val Met Leu Pro
 50                  55                  60
Lys Val Glu Thr Glu Ala Pro Gly Leu Val Arg Ser His Gly Glu Gln
 65                  70                  75                  80
Gly Gln Met Pro Glu Asn Met Gln Val Ser Gln Phe Lys Met Val Asn
                 85                  90                  95
Tyr Ser Tyr Asp Glu Asp Leu Glu Glu Leu Cys Pro Val Cys Gly Asp
             100                 105                 110
Lys Val Ser Gly Tyr His Tyr Gly Leu Leu Thr Cys Glu Ser Cys Lys
             115                 120                 125
Gly Phe Phe Lys Arg Thr Val Gln Asn Gln Lys Arg Tyr Thr Cys Ile
130                 135                 140
Glu Asn Gln Asn Cys Gln Ile Asp Lys Thr Gln Arg Lys Arg Cys Pro
145                 150                 155                 160
Tyr Cys Arg Phe Lys Lys Cys Ile Asp Val Gly Met Lys Leu Glu Ala
                165                 170                 175
Val Arg Ala Asp Arg Met Arg Gly Gly Arg Asn Lys Phe Gly Pro Met
            180                 185                 190
Tyr Lys Arg Asp Arg Ala Leu Lys Gln Gln Lys Lys Ala Leu Ile Arg
            195                 200                 205
Ala Asn Gly Leu Lys Leu Glu Ala Met Ser Gln Val Ile Gln Ala Met
210                 215                 220
Pro Ser Asp Leu Thr Ser Ala Ile Gln Asn Ile His Ser Ala Ser Lys
225                 230                 235                 240
Gly Leu Pro Leu Ser His Val Ala Leu Pro Pro Thr Asp Tyr Asp Arg
                245                 250                 255
Ser Pro Phe Val Thr Ser Pro Ile Ser Met Thr Met Pro Pro His Ser
            260                 265                 270
Ser Leu His Gly Tyr Gln Pro Tyr Gly His Phe Pro Ser Arg Ala Ile
            275                 280                 285
Lys Ser Glu Tyr Pro Asp Pro Tyr Ser Ser Ser Pro Glu Ser Met Met
            290                 295                 300
Gly Tyr Ser Tyr Met Asp Gly Tyr Gln Thr Asn Ser Pro Ala Ser Ile
305                 310                 315                 320
Pro His Leu Ile Leu Glu Leu Leu Lys Cys Glu Pro Asp Glu Pro Gln
                325                 330                 335
Val Gln Ala Lys Ile Met Ala Tyr Leu Gln Gln Glu Gln Ser Asn Arg
            340                 345                 350
Asn Arg Gln Glu Lys Leu Ser Ala Phe Gly Leu Leu Cys Lys Met Ala
            355                 360                 365
Asp Gln Thr Leu Phe Ser Ile Val Glu Trp Ala Arg Ser Ser Ile Phe
            370                 375                 380
Phe Arg Glu Leu Lys Val Asp Asp Gln Met Lys Leu Leu Gln Asn Cys
385                 390                 395                 400
Trp Ser Glu Leu Leu Ile Leu Asp His Ile Tyr Arg Gln Val Ala His
                405                 410                 415
Gly Lys Glu Gly Thr Ile Phe Leu Val Thr Gly Glu His Val Asp Tyr
            420                 425                 430
Ser Thr Ile Ile Ser His Thr Glu Val Ala Phe Asn Asn Leu Leu Ser
            435                 440                 445
Leu Ala Gln Glu Leu Val Val Arg Leu Arg Ser Leu Gln Phe Asp Gln
450                 455                 460
```

```
Arg Glu Phe Val Cys Leu Lys Phe Leu Val Leu Phe Ser Ser Asp Val
465                 470                 475                 480

Lys Asn Leu Glu Asn Leu Gln Leu Val Glu Gly Val Gln Glu Gln Val
                485                 490                 495

Asn Ala Ala Leu Leu Asp Tyr Thr Val Cys Asn Tyr Pro Gln Gln Thr
            500                 505                 510

Glu Lys Phe Gly Gln Leu Leu Arg Leu Pro Glu Ile Arg Ala Ile
        515                 520                 525

Ser Lys Gln Ala Glu Asp Tyr Leu Tyr Tyr Lys His Val Asn Gly Asp
530                 535                 540

Val Pro Tyr Asn Asn Leu Leu Ile Glu Met Leu His Ala Lys Arg Ala
545                 550                 555                 560

<210> SEQ ID NO 13
<211> LENGTH: 484
<212> TYPE: PRT
<213> ORGANISM: Mus musculus

<400> SEQUENCE: 13

Met Val Met Gln Phe Gln Gly Leu Glu Asn Pro Ile Gln Ile Ser Leu
1               5                   10                  15

His His Ser His Arg Leu Ser Gly Phe Val Pro Glu Gly Met Ser Val
                20                  25                  30

Lys Pro Ala Lys Gly Met Leu Thr Glu His Ala Ala Gly Pro Leu Gly
            35                  40                  45

Gln Asn Leu Asp Leu Glu Ser Tyr Ser Pro Tyr Asn Asn Val Pro Phe
        50                  55                  60

Pro Gln Val Gln Pro Gln Ile Ser Ser Ser Tyr Tyr Ser Asn Leu
65                  70                  75                  80

Gly Phe Tyr Pro Gln Gln Pro Glu Asp Trp Tyr Ser Pro Gly Ile Tyr
                85                  90                  95

Glu Leu Arg Arg Met Pro Ala Glu Thr Gly Tyr Gln Gly Glu Thr Glu
            100                 105                 110

Val Ser Glu Met Pro Val Thr Lys Lys Pro Arg Met Ala Ala Ala Ser
        115                 120                 125

Ala Gly Arg Ile Lys Gly Asp Glu Leu Cys Val Val Cys Gly Asp Arg
130                 135                 140

Ala Ser Gly Tyr His Tyr Asn Ala Leu Thr Cys Glu Gly Cys Lys Gly
145                 150                 155                 160

Phe Phe Arg Arg Ser Ile Thr Lys Asn Ala Val Tyr Lys Cys Lys Asn
                165                 170                 175

Gly Gly Asn Cys Val Met Asp Met Tyr Met Arg Arg Lys Cys Gln Glu
            180                 185                 190

Cys Arg Leu Arg Lys Cys Lys Glu Met Gly Met Leu Ala Glu Cys Leu
        195                 200                 205

Leu Thr Glu Ile Gln Cys Lys Ser Lys Arg Leu Arg Lys Asn Val Lys
    210                 215                 220

Gln His Ala Asp Gln Thr Ala Asn Glu Asp Ser Glu Gly Arg Asp
225                 230                 235                 240

Leu Arg Gln Val Thr Ser Thr Thr Lys Phe Cys Arg Glu Lys Thr Glu
                245                 250                 255

Leu Thr Ala Asp Gln Gln Thr Leu Leu Asp Tyr Ile Met Asp Ser Tyr
            260                 265                 270

Asn Lys Gln Arg Met Pro Gln Glu Ile Thr Asn Lys Ile Leu Lys Glu
        275                 280                 285
```

```
Glu Phe Ser Ala Glu Glu Asn Phe Leu Ile Leu Thr Glu Met Ala Thr
290                 295                 300

Ser His Val Gln Ile Leu Val Glu Phe Thr Lys Lys Leu Pro Gly Phe
305                 310                 315                 320

Gln Thr Leu Asp His Glu Asp Gln Ile Ala Leu Leu Lys Gly Ser Ala
            325                 330                 335

Val Glu Ala Met Phe Leu Arg Ser Ala Glu Ile Phe Asn Lys Lys Leu
            340                 345                 350

Pro Ala Gly His Ala Asp Leu Leu Glu Glu Arg Ile Arg Lys Ser Gly
            355                 360                 365

Ile Ser Asp Glu Tyr Ile Thr Pro Met Phe Ser Phe Tyr Lys Ser Val
370                 375                 380

Gly Glu Leu Lys Met Thr Gln Glu Glu Tyr Ala Leu Leu Thr Ala Ile
385                 390                 395                 400

Val Ile Leu Ser Pro Asp Arg Gln Tyr Ile Lys Asp Arg Glu Ala Val
            405                 410                 415

Glu Lys Leu Gln Glu Pro Leu Leu Asp Val Leu Gln Lys Leu Cys Lys
            420                 425                 430

Met Tyr Gln Pro Glu Asn Pro Gln His Phe Ala Cys Leu Leu Gly Arg
            435                 440                 445

Leu Thr Glu Leu Arg Thr Phe Asn His His His Ala Glu Met Leu Met
450                 455                 460

Ser Trp Arg Val Asn Asp His Lys Phe Thr Pro Leu Leu Cys Glu Ile
465                 470                 475                 480

Trp Asp Val Gln

<210> SEQ ID NO 14
<211> LENGTH: 431
<212> TYPE: PRT
<213> ORGANISM: Mus musculus

<400> SEQUENCE: 14

Met Arg Pro Glu Glu Ser Trp Ser Arg Val Gly Leu Val Gln Cys Glu
1               5                   10                  15

Glu Ala Asp Ser Ala Leu Glu Glu Pro Ile Asn Val Glu Glu Glu Asp
            20                  25                  30

Gly Gly Leu Gln Ile Cys Arg Val Cys Gly Asp Lys Ala Asn Gly Tyr
        35                  40                  45

His Phe Asn Val Met Thr Cys Glu Gly Cys Lys Gly Phe Phe Arg Arg
50                  55                  60

Ala Met Lys Arg Asn Val Arg Leu Arg Cys Pro Phe Arg Lys Gly Thr
65                  70                  75                  80

Cys Glu Ile Thr Arg Lys Thr Arg Arg Gln Cys Gln Ala Cys Arg Leu
                85                  90                  95

Arg Lys Cys Leu Glu Ser Gly Met Lys Lys Glu Met Ile Met Ser Asp
            100                 105                 110

Ala Ala Val Glu Gln Arg Arg Ala Leu Ile Lys Arg Lys Lys Arg Glu
        115                 120                 125

Lys Ile Glu Ala Pro Pro Gly Gly Gln Gly Leu Thr Glu Glu Gln
130                 135                 140

Gln Ala Leu Ile Gln Glu Leu Met Asp Ala Gln Met Gln Thr Phe Asp
145                 150                 155                 160

Thr Thr Phe Ser His Phe Lys Asp Phe Arg Leu Pro Ala Val Phe His
                165                 170                 175
```

```
Ser Gly Cys Glu Leu Pro Glu Phe Leu Gln Ala Ser Leu Leu Glu Asp
        180                 185                 190

Pro Ala Thr Trp Ser Gln Ile Met Lys Asp Arg Val Pro Met Lys Ile
    195                 200                 205

Ser Leu Gln Leu Arg Gly Glu Asp Gly Ser Ile Trp Asn Tyr Gln Pro
210                 215                 220

Pro Ser Lys Ser Asp Gly Lys Glu Ile Ile Pro Leu Leu Pro His Leu
225                 230                 235                 240

Ala Asp Val Ser Thr Tyr Met Phe Lys Gly Val Ile Asn Phe Ala Lys
                245                 250                 255

Val Ile Ser Tyr Phe Arg Asp Leu Pro Ile Glu Asp Gln Ile Ser Leu
                260                 265                 270

Leu Lys Gly Ala Thr Phe Glu Met Cys Ile Leu Arg Phe Asn Thr Met
            275                 280                 285

Phe Asp Thr Glu Thr Gly Thr Trp Glu Cys Gly Arg Leu Ala Tyr Cys
        290                 295                 300

Phe Glu Asp Pro Asn Gly Gly Phe Gln Lys Leu Leu Leu Asp Pro Leu
305                 310                 315                 320

Met Lys Phe His Cys Met Leu Lys Lys Leu Gln Leu His Lys Glu Glu
                325                 330                 335

Tyr Val Leu Met Gln Ala Ile Ser Leu Phe Ser Pro Asp Arg Pro Gly
                340                 345                 350

Val Val Gln Arg Ser Val Val Asp Gln Leu Gln Glu Arg Phe Ala Leu
            355                 360                 365

Thr Leu Lys Ala Tyr Ile Glu Cys Ser Arg Pro Tyr Pro Ala His Arg
        370                 375                 380

Phe Leu Phe Leu Lys Ile Met Ala Val Leu Thr Glu Leu Arg Ser Ile
385                 390                 395                 400

Asn Ala Gln Gln Thr Gln Gln Leu Leu Arg Ile Gln Asp Ser His Pro
                405                 410                 415

Phe Ala Thr Pro Leu Met Gln Glu Leu Phe Ser Ser Thr Asp Gly
                420                 425                 430

<210> SEQ ID NO 15
<211> LENGTH: 55
<212> TYPE: DNA
<213> ORGANISM: oligonucleotide

<400> SEQUENCE: 15
cgggatcccg gcgcgccgac tagtcgacgc gtcgaggtaa cctacggacc ggttt       55

<210> SEQ ID NO 16
<211> LENGTH: 58
<212> TYPE: DNA
<213> ORGANISM: oligonucleotide

<400> SEQUENCE: 16
ccgggtgaac atgttgttga ggctaggatc ctagcctcaa caacatgttc acttttg      58

<210> SEQ ID NO 17
<211> LENGTH: 169
<212> TYPE: PRT
<213> ORGANISM: Mus musculus
```

<400> SEQUENCE: 17

Met Gly Arg Arg Phe Leu Val Thr Val Arg Ile Gln Arg Ala Gly Arg
1               5                   10                  15

Pro Leu Gln Glu Arg Val Phe Leu Val Lys Phe Val Arg Ser Arg Arg
            20                  25                  30

Pro Arg Thr Ala Ser Cys Ala Leu Ala Phe Val Asn Met Leu Leu Arg
        35                  40                  45

Leu Glu Arg Ile Leu Arg Arg Gly Pro His Arg Asn Pro Gly Pro Gly
    50                  55                  60

Asp Asp Asp Gly Gln Arg Ser Arg Ser Ser Ser Ala Gln Leu Arg
65                  70                  75                  80

Cys Arg Phe Glu Leu Arg Gly Pro His Tyr Leu Leu Pro Pro Gly Ala
                85                  90                  95

Arg Arg Ser Ala Gly Arg Leu Pro Gly His Ala Gly Gly Ala Ala Arg
            100                 105                 110

Val Arg Gly Ser Ala Gly Cys Ala Arg Cys Leu Gly Ser Pro Ala Ala
        115                 120                 125

Arg Leu Gly Pro Arg Ala Gly Thr Ser Arg His Arg Ala Ile Phe Ala
    130                 135                 140

Phe Arg Trp Val Leu Phe Val Phe Arg Trp Val Val Phe Val Tyr Arg
145                 150                 155                 160

Trp Glu Arg Arg Pro Asp Arg Arg Ala
                165

<210> SEQ ID NO 18
<211> LENGTH: 929
<212> TYPE: DNA
<213> ORGANISM: Mus musculus

<400> SEQUENCE: 18
tctcgaggtg cctcaacgcc gaaggggctg ggggcggcgc ttctcacctc gcttgtcaca      60
gtgaggccgc cgctgaggga gtacagcagc gggagcatgg gtcgcaggtt cttggtcact     120
gtgaggattc agcgcgcggg ccgcccactc aagagaggg ttttcttggt gaagttcgtg     180
cgatcccgga gacccaggac agcgagctgc gctctggctt tcgtgaacat gttgttgagg     240
ctagagagga tcttgagaag agggccgcac cggaatcctg gaccaggtga tgatgatggg     300
caacgttcac gtagcagctc ttctgctcaa ctacggtgca gattcgaact gcgaggaccc     360
cactaccttc tcccgcccgg tgcacgacgc agcgcgggaa ggcttcctgg acacgctggt     420
ggtgctgcac gggtcagggg ctcggctgga tgtgcgcgat gcctgggtc gcctgccgct     480
cgacttggcc caagagcggg acatcaaga catcgtgcga tatttgcgtt ccgctgggtg     540
ctctttgtgt ccgctgggt ggtctttgtg taccgctggg aacgtcgccc agaccgacgg     600
gcatagcttc agctcaagca cgcccagggc cctggaactt cgcggccaat cccaagagca     660
gagctaaatc cggcctcagc ccgccttttt cttcttagct tcacttctag cgatgctagc     720
gtgtctagca tgtggcttta aaaatacat aataatgctt ttttgcaat cacgggaggg     780
agcagaggga gggagcagaa ggagggaggg agggagggag ggacctggac aggaaaggaa     840
tggcatgaga aactgagcga aggcggccgc gaagggaata atggctggat tgtttaaaaa     900
aataaaataa agatactttt taaaatgtc                                        929

<210> SEQ ID NO 19
<211> LENGTH: 2039
<212> TYPE: DNA
<213> ORGANISM: Mus musculus

<400> SEQUENCE: 19

```
gcgggactcc cgggctgtgt gcctcaggtc ggaactcggg gctagtgcct gtagagagac      60
cgaagcactc ggttccccca gggggggcctc agcctgggtg tgtgggggcg caggccccgg    120
ggatgctggg ctcagtgaag atggaggctc atgacctggc cgagtggagc tactacccgg    180
aggcgggcga ggtgtattct ccagtgaatc ctgtgcccac catggcccct ctcaactcct    240
acatgacctt gaacccactc agctctccct accctcccgg agggcttcag gcctccccac    300
tgcctacagg accoctggca ccoccagccc ccactgcgcc cttggggccc accttcccaa    360
gcttgggcac tggtggcagc accggaggca gtgcttccgg gtatgtagcc cagggcccg    420 ggcttgtaca tggaaaagag atggcaaagg gtaccggcg gccactggcc cacgccaaac    480
caccatattc ctacatctct ctcataacca tggctattca gcaggctcca ggcaagatgc    540
tgaccctgag tgaaatctac caatggatca tggacctctt cccgtactac cgggagaacc    600
agcaacgttg gcagaactcc atccggcatt cgctgtcctt caatgactgc ttcgtcaagg    660
tggcacgctc cccagacaag ccaggcaaag gctcctactg ggccttgcat ccagctctg    720 ggaacatgtt tgagaacggc tgctatctcc gccggcagaa gcgcttcaag ctggaggaga    780
aggcaaagaa aggaaacagc gccacatcgg ccagcaggaa tggtactgcg gggtcagcca    840
cctctgccac cactacagct gccactgcag tcacctcccc ggctcagccc cagcctacgc    900
catctgagcc cgaggcccag agtggggatg atgtgggggg tctggactgc gcctcacctc    960
cttcgtccac accttatttc agcggcctgg agctcccggg ggaactaaag ttggatgcgc   1020
cctataactt caaccaccct ttctctatca acaacctgat gtcagaacag acatcgacac   1080
cttccaaact ggatgtgggg tttgggggct acggggctga gagtgggggag cctggagtct   1140 actaccagag cctctattcc cgctctctgc ttaatgcatc ctagcagcgc aattgggaac   1200
gccatgatgg gcgtgggctg caacgttctt gggctctgat cttttctggtt acactttgct   1260 tgtcccatta attaacatct tatttggtct attactgtga tatgacccat tggctactgt   1320
ggtaactgcc atggactctt tggtaggcct agggttgggg tattaggaag gcagatgcgt   1380
ttggaagtgc tgcgaaggtg gtcatgttgg acatattgtg aaggcagtta gactggtgta   1440
ctatgaaagc tgccatatta agtgaagcca ttgggtgatt gatccactgg gtgcctgatg   1500
gtcgtgatgt tggatgacac atgtctggtc ctttggatga tgtgttggac atcttgattg   1560 acctttgag tatgtgacag aacacatctt ctttggctca ttttatcctg ggatcgcctc   1620
ttttttttcc tcttcttttt ctttttcttt ttcttttttt cttttccttt tttctttttt   1680
ttttcttttt tggcagactt cttggttcag cagatgccaa attggccacc atatcacatg   1740
gtgtcttttt tgacattctg gatgcatgga aggtcactgt attggcaagg tgacatctca   1800
gcatgctgct atgcaccaag atagatggtt accacaggcc tgccatcacc atctccttgg   1860
tggaggttgg gtgaggggaa gaggtgagca gaccctatga gttttctctg aagcccatcc   1920
ccaccctgtc tgtgagaaag ggctagtgtg ggtgtcggga gttcctactg aggtcaagtt   1980
cttgtctggg gcttgggaat actgcctgtg tttggccatt aaaaaggcac catctccat   2039
```

```
<210> SEQ ID NO 20
<211> LENGTH: 3203
<212> TYPE: DNA
<213> ORGANISM: Mus musculus

<400> SEQUENCE: 20
aaacagagca ggcaggggcc ctgattcact ggccgctggg gccagggttg ggggctgggg      60
gtgcccacag agcttgacta gtgggatttg ggggggcagt gggtgcagcg agcccggtcc     120
gttgactgcc agcctgccgg caggtagaca ccggccgtgg gtggggagg cggctagctc      180 agtggccttg gccgcgtgg cctggtggca gcggagccat ggtttctaag ctgagccagc      240
tgcagacgga gctcctggct gccctgctcg agtctggcct gagcaaagag gccctgatcc     300
aggccttggg ggagccaggg ccctacctga tggttggaga gggtcccctg gacaaggggg     360
agtcctgcgt ggggagtcga ggggacctga ccgagttgcc taatggcctt ggagaaacgc     420
gtggctctga agatgacacg gatgacgatg gggaagactt cgcgccaccc attctgaaag     480
agctggagaa cctcagccca gaggaggcag cccaccagaa agccgtggtg gagtcacttc     540
ttcaggagga cccatggcgc gtggcgaaga tggtcaagtc gtacttgcag cagcacaaca     600
tcccccagcg ggaggtggtg acaccacgg tctcaaccca gtcccacctg tcacagcacc      660
tcaacaaggg cacacccatg aagacacaga agcgggccgc tctgtacacc tggtacgtcc     720
gcaagcagcg agaggtggct cagcaattca cccacgcagg gcagggcgga ctgattgaag     780
agcccacagg cgatgagctg ccaactaaga agggggcgtag gaaccggttc aagtggggcc     840
ccgcatccca gcagatcctg ttccaggcct acgagaggca aaaaaacccc agcaaggaag     900
agcgagagac cttggtggag gagtgtaata gggcggagtg catccagagg ggggtgtcac     960
catcgcaggc ccagggggcta ggctccaacc ttgtcacgga ggtgcgtgtc tacaactggt    1020
ttgccaaccg gcgcaaggag gaagccttcc ggcacaagtt ggccatggac acctataacg    1080
gacctccacc ggggccaggc ccgggccctg cgctgcctgc tcacagttcc cccggcctgc    1140
ccacaaccac cctctctccc agtaaggtcc acggtgtacg gtacggacag tctgcaacca    1200
gtgaggcagc cgaggtgccc tccagcagcg gaggtccctt agtcacagtg tctgcggcct    1260
tacaccaagt atcccccaca ggcctggagc ccagcagcct gctgagcaca gaggccaagc    1320
tggtctcagc cacgggggt cccctgcctc ccgtcagcac cctgacagca ctgcacagct     1380
tggagcagac atctccgggt ctcaaccagc agccgcagaa ccttatcatg gcctcgctac    1440 ctgggggtcat gaccatcggg cccggggagc ctgcctccct gggacccacg ttcacgaaca    1500
cgggcgcctc caccctggtt atcggtctgg cctccactca ggcacagagc gtgcctgtca    1560
tcaacagcat ggggagtagc ctgaccacgc tgcagccggt ccagttttcc caaccactgc    1620
atccctccta tcagcagcct ctcatgcccc ccgtacagag ccacgtggcc cagagcccct    1680
tcatggcaac catggcccag ctgcagagcc cccacgcctt atacagccac aagcctgagg    1740
tggcccagta cacgcacacc agcctgctcc cgcagaccat gttgatcaca gacaccaacc    1800
tcagcaccct tgccagcctc acacccacca gcaggtctt caccctcagac acagaggcct    1860 ccagtgagcc cgggcttcac gagccaccct ctccagccac caccatccac atccccagcc    1920
aggacccgtc gaacatccag cacctgcagc ctgctcaccg gctcagcacc agtcccacag    1980
tgtcctccag cagcctggtg ttgtatcaga gttccgactc caacgggcac agccacctgc    2040
tgccatccaa ccatagtgtc atcgagactt ttatctccac ccagatgcc tcctcttccc     2100 agtaaccgtg gtgactgcct cccaggagct gggtccccag ggcctgcact gcctgcatag    2160
```

| | |
|---|---|
| ggggtgagga gggccgcagc cacactgcct ggaggatatc tgagcctgcc atgccacctg | 2220 |
| acacaggctg ctggccttcc cagaagtcta cgcattcatt gacactgctg ctcctccatc | 2280 |
| atcaggaagg gatggctctg aggtgtctca gcctgacaag cgagcctcga ggagctggag | 2340 |
| gacggcccaa tctgggcagt attgtggacc accatccctg ctgtttagaa taggaaattt | 2400 |
| aatgcttggg acaggagtgg ggaagctcgt ggtgcccgca ccccccagt cagagcctgc | 2460 |
| aggccttcaa ggatctgtgc tgagctctga ggccctagat caacacagct gcctgctgcc | 2520 |
| tcctgcacct ccccaggcca ttccaccctg caccagagac ccacgtgcct gtttgaggat | 2580 |
| taccctcccc accacgggga tttcctaccc agctgttctg ctaggctcgg agctgaggg | 2640 |
| gaagccactc ggggctctcc taggcttccc cctaccaagc catcccttct cccagcccca | 2700 |
| ggactgcact tgcaggccat ctgttcccctt ggatgtgtct tctgatgcca gcctggcaac | 2760 |
| ttgcatccac tagaaaggcc atttcagggc tcgggttgtc atccctgttc cttaggacct | 2820 |
| gcaactcatg ccaagaccac accatggaca atccactcct ctgcctgtag gcccctgaca | 2880 |
| acttccttcc tgctatgagg gagacctgca gaactcagaa gtcaaggcct gggcagtgtc | 2940 |
| tagtggagag ggtaccaaga ccagcagaga gaagccacct aagtggcctg ggggctagca | 3000 |
| gccattctga gaaatcctgg gtcccgagca gcccagggaa acacagcaca catgactgtc | 3060 |
| tcctcgggcc tactgcaggg aacctggcct tcagccagct cctttgtcat cctggactgt | 3120 |
| agcctacggc caaccataag tgagcctgta tgtttattta acttttagta aagtcagtaa | 3180 |
| aaagcaaaaa aaaaaaaaaa aaa | 3203 |

<210> SEQ ID NO 21
<211> LENGTH: 3393
<212> TYPE: DNA
<213> ORGANISM: Mus musculus

<400> SEQUENCE: 21

| | |
|---|---|
| aggggacaag ccggaggccc gcagagtggc cgcccgaggc tcagccgcag ttgcagctcc | 60 |
| gcggactcac ggagatcgcg ccggttttct gggaaactgg agctggccag gactgccgct | 120 |
| tcgcttcgaa gggaccgggc cctctttgtc attcttcgct ggagccgctc tggagctagc | 180 |
| agctgcgcct gggtgtgtag caggcagaaa gcaaggacta ggcttcttta gccggtgggt | 240 |
| gatccgaagg cctgctcagg gtgttcgaga ccagcctgga ctgcgtctgg gcacctccag | 300 |
| cctctgggcc ctggaataga gtccgccctc ccgcacgatt tctggagcaa ccgcaaatcc | 360 |
| aatttgggat tttcttttc ctgagcaaac cagagcctag aggtttctgc tttgatgctg | 420 |
| gatttaattc gtatatattt tgagcgagtt gggcctctcc tcgttttttg atctccggtt | 480 |
| gttttttttt tgggggggg gttagttttt gggttttgt tttgttttgt tttgttttga | 540 |
| ttttggtga cagttccgca caccgcatt ctagttcttg tctgcctcgt gctcagagct | 600 |
| tggggcgatg taccaaagcc tggccatggc cgccaaccac ggcccccgc ccggcgccta | 660 |
| cgaagcaggt ggccctggcg ccttcatgca cagcgcgggc gccgcgtcct cgcccgtcta | 720 |
| cgtgcccact ccgcgggtgc cgtcctctgt gctgggcctg tcctacctgc agggcggtgg | 780 |
| cagtgccgct gcagctggaa ccacctcggg tggcagctcc ggggccggcc gtcgggtgc | 840 |
| agggcctggg acccagcagg gtagccctgg ctggagccaa gctggagccg agggagccgc | 900 |
| ctacacccg ccgccgtgt cccgcgcgctt ctctttcccg gggactactg ggtccctggc | 960 |
| ggccgctgcc gccgctgccg cagccccggga agctgcagcc tacggcagtg gcggcggggc | 1020 |
| ggcgggcgct ggtctggctg gccgagagca gtacgggcgt ccgggcttcg ccggctccta | 1080 |

```
ctccagcccc tacccagcct acatggccga cgtgggagca tcctgggccg cagccgctgc    1140
cgcctctgcc ggcccttcg acagcccagt cctgcacagc ctgcctggac gggccaaccc    1200
tggaagacac cccaatctcg atatgtttga tgacttctca gaaggcagag agtgtgtcaa    1260
ttgtggggca atgtccaccc cactctggag gcgagatggg acgggacact acctgtgcaa    1320
tgcctgtggc ctctatcaca agatgaacgg catcaaccgg cccctcatta agcctcagcg    1380
ccgcctgtcc gcttcccgcc gggtaggcct ctcctgtgcc aactgccaga ctaccaccac    1440
cacgctgtgg cgtcgtaatg ccgagggtga gcctgtatgt aatgcctgcg gcctctacat    1500
gaagctccat ggggttccca ggcctcttgc aatgcggaag gagggattc aaaccagaaa    1560
acggaagccc aagaacctga ataaatctaa gacgccagca ggtcctgctg gtgagaccct    1620
ccctccctcc agtggtgcct ccagcggtaa ctccagcaat gccactagca gcagcagcag    1680
cagtgaagag atgcgcccca tcaagacaga gcccgggctg tcatctcact atgggcacag    1740
cagctccatg tcccagacat tcagtactgt gtccggccac gggcccctcca tccatccagt    1800
gctgtctgct ctgaagctgt ccccacaagg ctatgcatct cctgtcactc agacatcgca    1860
ggccagctcc aagcaggact cttggaacag cctggtcctg gctgacagtc atggggacat    1920
aatcaccgcg taatcagcgc ccccccttcc ctcttcaaat tcctgctcgg acttgggacg    1980
tggggccag caaagtaaaa ggctggggca cccttggcca gccccttgt ctgggaacaa    2040
ctcctgaaga caactgggt agaacttgaa gttgttgaca atcacttagg gatatgggtg    2100
ttccggggttg ttcaaacacc tttccaggtg gagcactgga aaagcctgcg ttcttacaga    2160
gaagcccacc ttggctgcaa gcacagcaca gtgaggcaag agacttcttc cttccttatt    2220
ctccacctgc ctgtccagga cagacacata atctccttca ccccagctcc ccacccagtt    2280
gtggtggtgg gttttctttt gtgatcctag agtggctgta ggggcggagg cttcaagaca    2340
ccatctacag tctgagcagg gtgtctactt gttgtagact agacatagaa gccctgccct    2400
tgtccaacac tccccttgct tgaggcatgg cacatctctg catgtcccat accagatctg    2460
actccaaagt gctgggttca atgcagatgt tactgaatgc ttcctgggga gattaggtga    2520
ggggaaggca catcacccat cacacagaat agcttcatca aatcgcagcc tggccatggt    2580
gccttccctt cctctcccag gaacatcaaa ccccttgctc tccagcctga acatctaccc    2640
tctgcaaaag tagagcccag ttgtgcagct aatgccacta ggtgctatat cccagcatcc    2700
tttttcacccc ttcacacaca ggggttccaa ggaggaacaa aacctgctac caaagcagcc    2760
ttggtgacta tggctcatct gcacctcagg gggtggggga gggccctctg gaggttgtgt    2820
ctacagcaca atactgttcc caggactcta gcttgcttgc cccgagcctg ccaagccaag    2880
ccctcttaag tcagacagtt acctggctct ggactttct ccagcacaga tcctttgtct    2940
agaaaataca gactgtttgc aaaataaatt caaagcagaa acaactaaag gaaatttgtg    3000
aaaggacaaa ggtgatagac gggagaagat gtccccaggg ctggcgggac agtcatgata    3060
gcagctgtcc taggattggc ctccctccca tctcccacca ttactggggc tcccagagat    3120
tcttccttgt cctcatcacc cacagagctg tagccaactg tggcattact ttatttttacc    3180
caaaattccc agccccaccc ctaaacctta ctggccgtag cagagaatag cttcgaacca    3240
agattctgtt gtaatcattt tcgctgtttc tccctcaagg ccgccttccc catgcctgcc    3300
cctcctccac aaacccgttaa cattgtctta aggtgaaatg gctgtaaaat cagtatttaa    3360
ctaataaatt tatctgtatt cctgtttcct ccg                                 3393
```

<210> SEQ ID NO 22
<211> LENGTH: 2046
<212> TYPE: DNA
<213> ORGANISM: Homo Sapiens

<400> SEQUENCE: 22

| | | | | | |
|---|---|---|---|---|---|
| ggagcccggg | gcgggcgagg | gcggggggtgt | cccggctata | aagcgtggcc | gcctcccgcg | 60 |
| gcgctcggga | cagccgtacc | ccgggcggtc | ggacgggcgg | gcgccggtgg | gagctcgggc | 120 |
| cgtgcccgct | gagagatcca | gagcgctccg | ttccccgggg | gccggagcgg | gggcgggtgg | 180 |
| gggcgtaagc | ccgggggatg | ctgggctcag | tgaagatgga | ggcccatgac | ctggccgagt | 240 |
| ggagctacta | cccggaggcg | ggcgaggtct | actcgccggt | gacccccagtg | cccaccatgg | 300 |
| ccccccctcaa | ctcctacatg | accctgaatc | ctctaagctc | tccctatccc | cctgggggc | 360 |
| tccctgcctc | cccactgccc | tcaggacccc | tggcaccccc | agcacctgca | gccccctgg | 420 |
| ggcccacttt | cccaggcctg | ggtgtcagcg | gtggcagcag | cagctcccggg | tacggggccc | 480 |
| cgggtcctgg | gctggtgcac | gggaaggaga | tgccgaaggg | gtatcggcgg | cccctggcac | 540 |
| acgccaagcc | accgtattcc | tatatctcac | tcatcaccat | ggccatccag | caggcgccgg | 600 |
| gcaagatgct | gaccttgagt | gaaatctacc | agtggatcat | ggacctcttc | ccttactacc | 660 |
| gggagaatca | gcagcgctgg | cagaactcca | ttcgccactc | gctgtctttc | aacgactgct | 720 |
| tcgtcaaggt | ggcgcgttcc | ccagacaagc | tggcaagggg | ctcctactgg | gccctacacc | 780 |
| ccagctcagg | gaacatgttt | gagaatggct | gctacctgcg | ccgccagaaa | cgcttcaagc | 840 |
| tggaggagaa | ggtgaaaaaa | gggggcagcg | gggctgccac | caccaccagg | aacgggacag | 900 |
| ggtctgctgc | ctcgaccacc | accccgcgg | ccacagtcac | ctccccgccc | cagccccgc | 960 |
| ctccagcccc | tgagcctgag | gcccagggcg | gggaagatgt | gggggctctg | gactgtggct | 1020 |
| cacccgcttc | ctccacaccc | tatttcactg | gcctggagct | cccaggggag | ctgaagctgg | 1080 |
| acgcgcccta | caacttcaac | cacccctttct | ccatcaacaa | cctaatgtca | gaacagacac | 1140 |
| cagcacctcc | caaactggac | gtggggtttg | ggggctacgg | ggctgaaggt | ggggagcctg | 1200 |
| gagtctacta | ccagggcctc | tattcccgct | ctttgcttaa | tgcatcctag | caggggttgg | 1260 |
| gaacatggtg | gtgggtatgg | ctggagctca | caccacgaag | ctcttggggc | ctgatccttc | 1320 |
| tggtgacact | tcacttgtcc | cattggttaa | catctgggtg | ggtctattac | ttactgtgat | 1380 |
| gactgctgtc | tcagtgggca | tggtgttgat | ccacggggta | ctgtgataac | caccatggat | 1440 |
| acattttggt | ggcccactgg | gtactgtgag | gactgctaca | ttgatggatg | ttattggcta | 1500 |
| atccactgca | tggtttgatg | gccaccatct | cggttggccc | tttgggtgtg | atggtgatag | 1560 |
| catttcagtg | acatcttctt | tggccccccc | cattaggtgc | tgtgcccact | tctttttttgg | 1620 |
| tgtacttggc | acagtaggtg | ccaagttggc | caccattctg | tgtaacacct | ttttggccc | 1680 |
| attgggtgct | ttgatggaca | tcatactggg | taggtgacaa | cgtcagtggg | ccaccatgtg | 1740 |
| ccatgatggc | tgctgcagcc | ccgtgttggc | catgtcgtca | ccattctctc | tggcatgggt | 1800 |
| tgggtagggg | atgagggtga | gaatactcct | tggttttctc | tgaagcccac | cctttccccc | 1860 |
| aactctggtc | caggagaaac | cagaaaaggc | tggttagggt | gtgggaatt | tctactgaag | 1920 |
| tctgattctt | tcccgggaag | cggggtactg | gctgtgttta | atcattaaag | gtaccgtgtc | 1980 |
| cgcctcttaa | aaaaaaaaa | aaaaaaaaa | aaaaaaaaa | aaaaaaaaa | aaaaaaaaa | 2040 |
| aaaaaa | | | | | | 2046 |

<210> SEQ ID NO 23
<211> LENGTH: 3241
<212> TYPE: DNA
<213> ORGANISM: Homo Sapiens

<400> SEQUENCE: 23

| | | | | | |
|---|---|---|---|---|---|
| cgtggccctg | tggcagccga | gccatggttt | ctaaactgag | ccagctgcag | acggagctcc | 60 |
| tggcggccct | gctcgagtca | gggctgagca | aagaggcact | gatccaggca | ctgggtgagc | 120 |
| cggggcccta | cctcctggct | ggagaaggcc | cctggacaa | gggggagtcc | tgcggcggcg | 180 |
| gtcgagggga | gctggctgag | ctgcccaatg | ggctggggga | gactcggggc | tccgaggacg | 240 |
| agacggacga | cgatggggaa | gacttcacgc | cacccatcct | caaagagctg | agaaccctca | 300 |
| gccctgagga | ggcggcccac | cagaaagccg | tggtggagac | ccttctgcag | gaggacccgt | 360 |
| ggcgtgtggc | gaagatggtc | aagtcctacc | tgcagcagca | caacatccca | cagcgggagg | 420 |
| tggtcgatac | cactggcctc | aaccagtccc | acctgtccca | cacctcaac | aagggcactc | 480 |
| ccatgaagac | gcagaagcgg | gccgccctgt | acacctggta | cgtccgcaag | cagcgagagg | 540 |
| tggcgcagca | gttcacccat | gcagggcagg | gagggctgat | tgaagagccc | acaggtgatg | 600 |
| agctaccaac | caagaagggg | cggaggaacc | gtttcaagtg | gggcccagca | tcccagcaga | 660 |
| tcctgttcca | ggcctatgag | aggcagaaga | accctagcaa | ggaggagcga | gagacgctag | 720 |
| tggaggagtg | caatagggcg | gaatgcatcc | agagaggggt | gtccccatca | caggcacagg | 780 |
| ggctgggctc | caacctcgtc | acggaggtgc | gtgtctacaa | ctggtttgcc | aaccggcgca | 840 |
| aagaagaagc | cttccggcac | aagctggcca | tggacacgta | cagcgggccc | ccccagggc | 900 |
| caggcccggg | acctgcgctg | cccgctcaca | gctcccctgg | cctgcctcca | cctgccctct | 960 |
| ccccccagtaa | ggtccacggt | gtgcgctatg | acagcctgc | gaccagtgag | actgcagaag | 1020 |
| taccctcaag | cagcggcggt | cccttagtga | cagtgtctac | acccctccac | caagtgtccc | 1080 |
| ccacgggcct | ggagcccagc | cacagcctgc | tgagtacaga | agccaagctg | gtctcagcag | 1140 |
| ctgggggccc | cctccccct | gtcagcaccc | tgacagcact | gcacagcttg | gagcagacat | 1200 |
| ccccaggcct | caaccagcag | ccccagaacc | tcatcatggc | ctcacttcct | ggggtcatga | 1260 |
| ccatcgggc | tggtgagcct | gcctccctgg | gtcctacgtt | caccaacaca | ggtgcctcca | 1320 |
| ccctggtcat | cggcctggcc | tccacgcagg | cacagagtgt | gccggtcatc | aacagcatgg | 1380 |
| gcagcagcct | gaccaccctg | cagcccgtcc | agttctccca | gccgctgcac | ccctcctacc | 1440 |
| agcagccgct | catgccacct | gtgcagagcc | atgtgaccca | gagccccttc | atggccacca | 1500 |
| tggctcagct | gcagagcccc | cacgccctct | acagccacaa | gcccgaggtg | gcccagtaca | 1560 |
| cccacacggg | cctgctcccg | cagactatgc | tcatcaccga | caccaccaac | ctgagcgccc | 1620 |
| tggccagcct | cacgcccacc | aagcaggtct | tcacctcaga | cactgaggcc | tccagtgagt | 1680 |
| ccgggctt ca | cacgccggca | tctcaggcca | ccaccctcca | cgtccccagc | caggaccctg | 1740 |
| ccggcatcca | gcacctgcag | ccggcccacc | ggctcagcgc | cagccccaca | gtgtcctcca | 1800 |
| gcagcctggt | gctgtaccag | agctcagact | ccagcaatgg | ccagagccac | ctgctgccat | 1860 |
| ccaaccacag | cgtcatcgag | accttcatct | ccacccagat | ggcctcttcc | tcccagtaac | 1920 |
| cacggcacct | gggccctggg | gcctgtactg | cctgcttggg | gggtgatgag | ggcagcagcc | 1980 |
| agccctgcct | ggaggacctg | agcctgccga | gcaaccgtgg | ccttcctgg | acagctgtgc | 2040 |
| ctcgctcccc | actctgctct | gatgcatcag | aaagggaggg | ctctgaggcg | ccccaacccg | 2100 |
| tggaggctgc | tcggggtgca | caggaggggg | tcgtggagag | ctaggagcaa | agcctgttca | 2160 |

| | |
|---|---:|
| tggcagatgt aggagggact gtcgctgctt cgtgggatac agtcttctta cttggaactg | 2220 |
| aaggggcgg cctatgactt gggcacccc agcctgggcc tatggagagc cctgggaccg | 2280 |
| ctacaccact ctggcagcca cacttctcag gacacaggcc tgtgtagctg tgacctgctg | 2340 |
| agctctgaga ggccctggat cagcgtggcc ttgttctgtc accaatgtac ccaccgggcc | 2400 |
| actccttcct gccccaactc cttccagcta gtgacccaca tgccatttgt actgaccca | 2460 |
| tcacctactc acacaggcat ttcctgggtg gctactctgt gccagagcct ggggctctaa | 2520 |
| cgcctgagcc cagggaggcc gaagctaaca gggaaggcag gcagggctct cctggcttcc | 2580 |
| catcccagc gattccctct cccaggcccc atgacctcca gctttcctgt atttgttccc | 2640 |
| aagagcatca tgcctctgag gccagcctgg cctcctgcct ctactgggaa ggctacttcg | 2700 |
| gggctgggaa gtcgtcctta ctcctgtggg agcctcgcaa cccgtgccaa gtccaggtcc | 2760 |
| tggtggggca gctcctctgt ctcgagcgcc ctgcagaccc tgcccttgtt tggggcagga | 2820 |
| gtagctgagc tcacaaggca gcaaggcccg agcagctgag cagggccggg gaactggcca | 2880 |
| agctgaggtg cccaggagaa gaaagaggtg accccagggc acaggagcta cctgtgtgga | 2940 |
| caggactaac actcagaagc ctgggggcct ggctggctga gggcagttcg cagccaccct | 3000 |
| gaggagtctg aggtcctgag cactgccagg agggacaaag gagcctgtga acccaggaca | 3060 |
| agcatggtcc cacatccctg ggcctgctgc tgagaacctg gccttcagtg taccgcgtct | 3120 |
| accctgggat tcaggaaaag gctggggtg acccggcacc cctgcagct tgtagcagc | 3180 |
| cggggcgagt ggcacgttta tttaactttt agtaaagtca aggagaaatg cggtggaaaa | 3240 |
| a | 3241 |

<210> SEQ ID NO 24
<211> LENGTH: 3419
<212> TYPE: DNA
<213> ORGANISM: Homo Sapiens

<400> SEQUENCE: 24

| | |
|---|---:|
| ttggaggcgg ccggcgcagg ggccgcgaga ggcttcgtcg ccgctgcagc tccgggggct | 60 |
| cccaggggag cgtgcgcgga acctccaggc ccagcaggac cccggctgcg gcgaggagga | 120 |
| aggagccagc ctagcagctt ctgcgcctgt ggccgcgggt gtcctggagg cctctcggtg | 180 |
| tgacgagtgg gggaccccgaa ggctcgtgcg ccacctccag gcctggacgc tgccctccgt | 240 |
| cttctgcccc caataggtgc gccggacctt caggccctgg ggtgaattca gctgctccta | 300 |
| catcagcttc cggaaccacc aaaaattcaa attgggattt tccggagtaa acaagagcct | 360 |
| agagcccttt gctcaatgct ggatttaata cgtatatatt tttaagcgag ttggtttttt | 420 |
| cccctttgat ttttgatctt cgcgacagtt cctcccacgc atattatcgt tgttgccgtc | 480 |
| gttttctctc cccgcgtggc tccttgacct gcgagggaga gagaggacac cgaagccggg | 540 |
| agctcgcagg gaccatgtat cagagcttgg ccatggccgc caaccacggg ccgcccccg | 600 |
| gtgcctacga ggcgggcggc cccggcgcct tcatgcacgg cgcgggcgcc cgtcctcgc | 660 |
| cagtctacgt gcccacaccg cgggtgccct cctccgtgct gggcctgtcc tacctccagg | 720 |
| gcggaggcgc gggctctgcg tccgaggcg ctcgggcgg cagctccggt ggggccgcgt | 780 |
| ctggtgcggg gccgggacc cagcagggca gcccgggatg gagccaggcg ggagccgacg | 840 |
| gagccgctta caccccgccg ccggtgtcgc gcgcgcttctc cttcccgggg accaccgggt | 900 |
| ccctggcgg cgccgccgcc gctgccgcgg cccgggaagc tgcggcctac agcagtggcg | 960 |
| gcggagcggc gggtgcgggc ctggcgggcc gcgagcagta cggcgcgcc ggcttcgcgg | 1020 |

```
gctcctactc cagcccctac ccggcttaca tggccgacgt gggcgcgtcc tgggccgcag    1080
ccgccgccgc ctccgccggc cccttcgaca gcccggtcct gcacagcctg cccggccggg    1140
ccaacccggc cgcccgacac cccaatctcg atatgtttga cgacttctca gaaggcagag    1200
agtgtgtcaa ctgtggggct atgtccaccc cgctctggag gcgagatggg acgggtcact    1260
atctgtgcaa cgcctgcggc ctctaccaca agatgaacgg catcaaccgg ccgctcatca    1320
agcctcagcg ccggctgtcc gcctcccgcc gagtgggcct ctcctgtgcc aactgccaga    1380
ccaccaccac cacgctgtgg cgccgcaatg cggagggcga gcctgtgtgc aatgcctgcg    1440
gcctctacat gaagctccac ggggtcccca ggcctcttgc aatgcggaaa gaggggatcc    1500
aaaccagaaa acggaagccc aagaacctga ataaatctaa gacaccagca gctccttcag    1560
gcagtgagag ccttcctccc gccagcggtg cttccagcaa ctccagcaac gccaccacca    1620
gcagcagcga ggagatgcgt cccatcaaga cggagcctgg cctgtcatct cactacgggc    1680
acagcagctc cgtgtcccag acgttctcag tcagtgcgat gtctggccat gggccctcca    1740
tccaccctgt cctctcggcc ctgaagctct ccccacaagg ctatgcgtct cccgtcagcc    1800
agtctccaca gaccagctcc aagcaggact cttggaacag cctggtcttg gccgacagtc    1860
acggggacat aatcactgcg taatcttccc tcttccctcc tcaaattcct gcacggacct    1920
gggacttgga ggatagcaaa gaaggaggcc ctgggctccc aggggccggc ctcctctgcc    1980
tggtaatgac tccagaacaa caactgggaa gaaacttgaa gtcgcaaatc tggttagggg    2040
aagcgggtgt tggattttct cagatgcctt tacacgctga tgggactgga gggagcccac    2100
ccttcagcac gagcacactg catctctcct gtgagttgga gacttctttc ccaagatgtc    2160
cttgtcccct gcgttcccca ctgtggccta gaccgtgggt tttgcattgt gtttctagca    2220
ccgaggatct gagaacaagc ggagggccgg gccctgggac ccctgctcca gcccgaatga    2280
cggcatctgt ttgccatgta cctggatgcg acgggcccct ggggacaggc ccttgcccca    2340
tccatccgct tgaggcatgg caccgccctg catccctaat accaaatctg actccaaaat    2400
tgtggggtgt gacatacaag tgactgaaca cttcctgggg agctacaggg gcacttaacc    2460
caccacagca cagcctcatc aaaatgcagc tggcaacttc tccccaggt gccttccccc    2520 tgctgccggc ctttgctcct tcacttccaa catctctcaa aataaaaatc cctcttcccg    2580
ctctgagcga ttcagctctg cccgcagctt gtacatgtct ctcccctggc aaaacaagag    2640
ctgggtagtt tagccaaacg gcacccctc gagttcactg cagacccttc gttcaccgtg    2700
tcacacatag aggggttctg agtaagaaca aacgttctg ctgctcaagc cagtctggca    2760
agcactcagc ccagcctcga ggtccttctg gggagagtgt aagtggacag agtcctggtc    2820
agggggcagg agtgtcccaa gggctggccc acctgctgtc tgtctgctcc tcctagccct    2880
tggtcagatg gcagccagag tccctcagga cctgcagcct cgccccggca gaagtctttt    2940
gtccaggagg caaaaagcca gagattctgc aacacgaatt cgaagcaaac aaacacaaca    3000
caacagaatt cctggaaaga agacgactgc taagacacgg cagggggcc tggagggagc    3060 ctccgactct gagctgctcc gggatctgcc gcgttctcct ctgcacattg ctgtttctgc    3120
ccctgatgct ggagctcaag gagactcctt cctctttctc agcagagctg tagctgactg    3180
tggcattact acgcctcccc acacgcccag accctcact ccaaaatcct actggctgta    3240
gcagagaata cctttgaacc aagattctgt tttaatcatc atttacattg ttttcttcca    3300
aaggccccct cgtatcccct ccctaaccca caaacctgtt aacattgtct taaggtgaaa    3360
tggctggaaa atcagtattt aactaataaa tttatctgta ttcctcttaa aaaaaaaaa    3419
```

<210> SEQ ID NO 25
<211> LENGTH: 350
<212> TYPE: PRT
<213> ORGANISM: Homo Sapiens

<400> SEQUENCE: 25

Met Leu Gly Ser Val Lys Met Glu Ala His Asp Leu Ala Glu Trp Ser
1               5                   10                  15

Tyr Tyr Pro Glu Ala Gly Glu Val Tyr Ser Pro Val Thr Pro Val Pro
            20                  25                  30

Thr Met Ala Pro Leu Asn Ser Tyr Met Thr Leu Asn Pro Leu Ser Ser
        35                  40                  45

Pro Tyr Pro Pro Gly Gly Leu Pro Ala Ser Pro Leu Pro Ser Gly Pro
50                  55                  60

Leu Ala Pro Pro Ala Pro Ala Ala Pro Leu Gly Pro Thr Phe Pro Gly
65                  70                  75                  80

Leu Gly Val Ser Gly Gly Ser Ser Ser Ser Gly Tyr Gly Ala Pro Gly
                85                  90                  95

Pro Gly Leu Val His Gly Lys Glu Met Pro Lys Gly Tyr Arg Arg Pro
            100                 105                 110

Leu Ala His Ala Lys Pro Pro Tyr Ser Tyr Ile Ser Leu Ile Thr Met
        115                 120                 125

Ala Ile Gln Gln Ala Pro Gly Lys Met Leu Thr Leu Ser Glu Ile Tyr
130                 135                 140

Gln Trp Ile Met Asp Leu Phe Pro Tyr Tyr Arg Glu Asn Gln Gln Arg
145                 150                 155                 160

Trp Gln Asn Ser Ile Arg His Ser Leu Ser Phe Asn Asp Cys Phe Val
                165                 170                 175

Lys Val Ala Arg Ser Pro Asp Lys Pro Gly Lys Gly Ser Tyr Trp Ala
            180                 185                 190

Leu His Pro Ser Ser Gly Asn Met Phe Glu Asn Gly Cys Tyr Leu Arg
        195                 200                 205

Arg Gln Lys Arg Phe Lys Leu Glu Glu Lys Val Lys Lys Gly Gly Ser
210                 215                 220

Gly Ala Ala Thr Thr Thr Arg Asn Gly Thr Gly Ser Ala Ala Ser Thr
225                 230                 235                 240

Thr Thr Pro Ala Ala Thr Val Thr Ser Pro Pro Gln Pro Pro Pro Pro
                245                 250                 255

Ala Pro Glu Pro Glu Ala Gln Gly Gly Glu Asp Val Gly Ala Leu Asp
            260                 265                 270

Cys Gly Ser Pro Ala Ser Ser Thr Pro Tyr Phe Thr Gly Leu Glu Leu
        275                 280                 285

Pro Gly Glu Leu Lys Leu Asp Ala Pro Tyr Asn Phe Asn His Pro Phe
290                 295                 300

Ser Ile Asn Asn Leu Met Ser Glu Gln Thr Pro Ala Pro Pro Lys Leu
305                 310                 315                 320

Asp Val Gly Phe Gly Gly Tyr Gly Ala Glu Gly Gly Glu Pro Gly Val
                325                 330                 335

Tyr Tyr Gln Gly Leu Tyr Ser Arg Ser Leu Leu Asn Ala Ser
            340                 345                 350

<210> SEQ ID NO 26
<211> LENGTH: 631
<212> TYPE: PRT
<213> ORGANISM: Homo Sapiens

```
<400> SEQUENCE: 26

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Arg Gly Glu Leu Ala Glu Leu Pro Asn Gly Leu
50                  55                  60

Gly Glu Thr Arg Gly Ser Glu Asp Glu Thr Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
                100                 105                 110

Trp Arg Val Ala Lys Met Val Lys Ser Tyr Leu Gln Gln His Asn Ile
            115                 120                 125

Pro Gln Arg Glu Val Val Asp Thr Thr Gly Leu Asn Gln Ser His Leu
            130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
        210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
        275                 280                 285

Pro Pro Pro Gly Pro Gly Pro Gly Pro Ala Leu Pro Ala His Ser Ser
        290                 295                 300

Pro Gly Leu Pro Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
        355                 360                 365

Leu Val Ser Ala Ala Gly Gly Pro Leu Pro Pro Val Ser Thr Leu Thr
        370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415
```

```
Gly Glu Pro Ala Ser Leu Gly Pro Thr Phe Thr Asn Thr Gly Ala Ser
            420                 425                 430

Thr Leu Val Ile Gly Leu Ala Ser Thr Gln Ala Gln Ser Val Pro Val
        435                 440                 445

Ile Asn Ser Met Gly Ser Ser Leu Thr Thr Leu Gln Pro Val Gln Phe
    450                 455                 460

Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
                485                 490                 495

Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
        515                 520                 525

Asn Leu Ser Ala Leu Ala Ser Leu Thr Pro Thr Lys Gln Val Phe Thr
    530                 535                 540

Ser Asp Thr Glu Ala Ser Ser Glu Ser Gly Leu His Thr Pro Ala Ser
545                 550                 555                 560

Gln Ala Thr Thr Leu His Val Pro Ser Gln Asp Pro Ala Gly Ile Gln
                565                 570                 575

His Leu Gln Pro Ala His Arg Leu Ser Ala Ser Pro Thr Val Ser Ser
            580                 585                 590

Ser Ser Leu Val Leu Tyr Gln Ser Ser Asp Ser Ser Asn Gly Gln Ser
        595                 600                 605

His Leu Leu Pro Ser Asn His Ser Val Ile Glu Thr Phe Ile Ser Thr
    610                 615                 620

Gln Met Ala Ser Ser Ser Gln
625                 630

<210> SEQ ID NO 27
<211> LENGTH: 442
<212> TYPE: PRT
<213> ORGANISM: Homo Sapiens

<400> SEQUENCE: 27

Met Tyr Gln Ser Leu Ala Met Ala Ala Asn His Gly Pro Pro Pro Gly
1               5                   10                  15

Ala Tyr Glu Ala Gly Gly Pro Gly Ala Phe Met His Gly Ala Gly Ala
            20                  25                  30

Ala Ser Ser Pro Val Tyr Val Pro Thr Pro Arg Val Pro Ser Ser Val
        35                  40                  45

Leu Gly Leu Ser Tyr Leu Gln Gly Gly Gly Ala Gly Ser Ala Ser Gly
    50                  55                  60

Gly Ala Ser Gly Gly Ser Gly Gly Ala Ser Gly Ala Gly Pro
65                  70                  75                  80

Gly Thr Gln Gln Gly Ser Pro Gly Trp Ser Gln Ala Gly Ala Asp Gly
                85                  90                  95

Ala Ala Tyr Thr Pro Pro Pro Val Ser Pro Arg Phe Ser Phe Pro Gly
            100                 105                 110

Thr Thr Gly Ser Leu Ala Ala Ala Ala Ala Ala Ala Ala Ala Arg Glu
        115                 120                 125

Ala Ala Ala Tyr Ser Ser Gly Gly Gly Ala Ala Gly Ala Gly Leu Ala
    130                 135                 140

Gly Arg Glu Gln Tyr Gly Arg Ala Gly Phe Ala Gly Ser Tyr Ser Ser
145                 150                 155                 160
```

-continued

```
Pro Tyr Pro Ala Tyr Met Ala Asp Val Gly Ala Ser Trp Ala Ala Ala
            165                 170                 175

Ala Ala Ala Ser Ala Gly Pro Phe Asp Ser Pro Val Leu His Ser Leu
            180                 185                 190

Pro Gly Arg Ala Asn Pro Ala Ala Arg His Pro Asn Leu Asp Met Phe
            195                 200                 205

Asp Asp Phe Ser Glu Gly Arg Glu Cys Val Asn Cys Gly Ala Met Ser
    210                 215                 220

Thr Pro Leu Trp Arg Arg Asp Gly Thr Gly His Tyr Leu Cys Asn Ala
225                 230                 235                 240

Cys Gly Leu Tyr His Lys Met Asn Gly Ile Asn Arg Pro Leu Ile Lys
            245                 250                 255

Pro Gln Arg Arg Leu Ser Ala Ser Arg Arg Val Gly Leu Ser Cys Ala
            260                 265                 270

Asn Cys Gln Thr Thr Thr Thr Leu Trp Arg Arg Asn Ala Glu Gly
            275                 280                 285

Glu Pro Val Cys Asn Ala Cys Gly Leu Tyr Met Lys Leu His Gly Val
    290                 295                 300

Pro Arg Pro Leu Ala Met Arg Lys Glu Gly Ile Gln Thr Arg Lys Arg
305                 310                 315                 320

Lys Pro Lys Asn Leu Asn Lys Ser Lys Thr Pro Ala Ala Pro Ser Gly
            325                 330                 335

Ser Glu Ser Leu Pro Pro Ala Ser Gly Ala Ser Ser Asn Ser Ser Asn
            340                 345                 350

Ala Thr Thr Ser Ser Ser Glu Glu Met Arg Pro Ile Lys Thr Glu Pro
            355                 360                 365

Gly Leu Ser Ser His Tyr Gly His Ser Ser Ser Val Ser Gln Thr Phe
            370                 375                 380

Ser Val Ser Ala Met Ser Gly His Gly Pro Ser Ile His Pro Val Leu
385                 390                 395                 400

Ser Ala Leu Lys Leu Ser Pro Gln Gly Tyr Ala Ser Pro Val Ser Gln
            405                 410                 415

Ser Pro Gln Thr Ser Ser Lys Gln Asp Ser Trp Asn Ser Leu Val Leu
            420                 425                 430

Ala Asp Ser His Gly Asp Ile Ile Thr Ala
            435                 440
```

HEPATOCYTE-LIKE CELLS AND USES THEREOF

CROSS REFERENCE TO RELATED APPLICATION

This application is a 35 U.S.C. §371 national stage application of International Application No. PCT/CN2011/001857, filed Nov. 4, 2011, which claims priority of Chinese Application No. 201010531420.4 filed on Nov. 4, 2010. The content of the application is incorporated by reference in its entirety.

FIELD OF THE INVENTION

This invention relates to hepatocyte-like cells, related compositions, and related methods that are useful for improving liver function and treating various liver disorders.

BACKGROUND OF THE INVENTION

The liver is a vital organ in various vertebrates and some other animals. In the human body, the liver is the largest internal organ and provides many essential functions, including metabolic, exocrine and endocrine functions. The liver is necessary for survival. Without liver function, a human can only survive up to 24 hours. Currently, there is no way to compensate for long term absence of liver function, although liver dialysis can be used short term.

Disorders of the liver, including liver failure and end-stage liver diseases, are responsible for a huge number of deaths around the world and are a major burden on the health care system. Although liver transplantation has been successfully used for treat the disorders, its efficacy is limited and connected to many complications such as infection or rejection. Liver transplantation is also limited due to shortage of available donor organs and lifelong use of immunosuppression in recipients. Cell-based therapy, such as those based hepatocytes, on are believed to hold a great promise for treating these severe diseases.

Hepatocytes, the principal cell type in the liver, are responsible for function and regeneration of the adult liver. Along with biliary epithelial cells, hepatocytes are derived from the embryonic endoderm. Human hepatocytes can be used for modeling and understanding liver diseases, drug efficacy and toxicity testing, and cell replacement therapy. However, primary human hepatocytes are scarce and, despite their ability to efficiently proliferate in vivo, cannot be expanded in vitro.

Thus, there is a continuing unmet need for an unlimited source of human hepatocytes or hepatocyte-like cells.

SUMMARY OF INVENTION

This invention relates to a novel method for generating hepatocyte-like cells, related cells, and related methods.

One aspect of this invention features a method of generating hepatocyte-like cells. The method includes expressing in a starting cell a heterologous Hnf polypeptide and a heterologous Foxa polypeptide; and culturing the starting cell in a medium for a period of time to obtain one or more progeny cells thereof thereby generating hepatocyte-like cells. In one embodiment, the method further includes expressing in the starting cell a heterologous GATA4 polypeptide. The Hnf, Foxa, and GATA4 polypeptides can include the sequences of SEQ ID NOs: 1-3, respectively. In a preferred embodiment, the method further includes expressing in the starting cell one or more polypeptides that have sequences selected from the group consisting of SEQ ID NO: 4-14.

The starting cell can be a somatic cell. It can be a cell from an adult source, an embryonic source, or a fetal source. Examples of the cell include a fibroblast, an epithelium cell, a blood cell, a neuron, an embryonic cell, or a cell derived from a tissue or organ of a subject. Preferably, the starting cell is $p19^{Arf}$ null or expresses the $p19^{Arf}$ gene at a level lower than a predetermined level so that the cells can proliferate in vitro for a period of time and do not undergo cellular death or senescence as discussed below. The predetermined level can be one obtained from a control cell, e.g., a wildtype cell from a corresponding tissue or organ. To generate the hepatocyte-like cells, one can express the above-mentioned heterologous polypeptides in the starting cells and then culture the cells for a period of time, e.g., at least 2, 3, 4, 5, 6, 7, 10, 14 days. For example, the cell can be cultured for 2-30 days, e.g., 5-25 days, or 14-21 days.

In another aspect, this invention provides a cultured recombinant cell that contains, among others, (i) a first agent selected from a first group consisting of a heterologous Hnf polypeptide and a first nucleic acid encoding the Hnf polypeptide; and (ii) a second agent selected from a second group consisting of a heterologous Foxa polypeptide and a second nucleic acid encoding the Foxa polypeptide. The cell can further contain a third agent selected from a third group consisting of a heterologous GATA4 polypeptide and a third nucleic acid encoding the GATA4 polypeptide. The cell is positive for one or more of hepatic functional genes as shown in Tables 2 and 3 below. The cell is capable of metabolizing one or more compounds selected from group consisting of phenacetin, testosterone, and diclofenac. In one embodiment, the cell is a hepatocyte-like cell that is obtained using the method described above.

In another aspect, this invention provides a pharmaceutical composition having the above-described cell and a pharmaceutically acceptable carrier. The invention also provides a bioartificial device having the cell. As discussed in detail below, the cell, pharmaceutical composition, and device can be used in a method for improving the liver function of a subject. To that end, one can administer to a subject in need thereof the cell, or implanting the device in the subject, thereby improving the liver function.

In yet another aspect, this invention provides a method of evaluating toxicity, carcinogenicity, or biotransformation activity of a test substance. The method includes contacting a test substance with the above-described cell, and examining a level of metabolic activity or viability of the cell. The value of the level indicates the toxicity, carcinogenicity, or biotransformation activity of the test substance.

This invention further provides a composition having (i) a first agent selected from a first group consisting of an isolated Hnf polypeptide and an isolated first nucleic acid encoding the Hnf polypeptide; and (ii) a second agent selected from a second group consisting of an isolated Foxa polypeptide and an isolated second nucleic acid encoding the Foxa polypeptide. In a preferred embodiment, the composition further contains a third agent selected from a third group consisting of an isolated GATA4 polypeptide and an isolated third nucleic acid encoding the GATA4 polypeptide. Also featured is a kit having the composition and a starting cell.

The details of one or more embodiments of the invention are set forth in the description below. Other features, objects, and advantages of the invention will be apparent from the description and from the claims.

BRIEF DESCRIPTION OF THE DRAWINGS

FIGS. 1a-f are diagrams and photographs of an experimental design (1a), results showing that three transcription factors induce hepatic conversion of tail-tip fibroblasts (1b-d), and effects of individual factor withdrawal from 3TF on epithelial colony formation (1f), where each scale bar represents 100 μm and the data are presented as mean±s.d.

FIGS. 2a-l are diagrams and photographs of characterization of iHep cells in vitro, showing that 3TF-induced iHep cells had typical epithelial morphology (2a); that epithelial conversion of TTFs was confirmed by immunofluorescent staining of Tjp1 and E-cadherin (2b and c); that expression of indicated genes was analyzed by RT-PCR during the induction of iHep cells (2d); global gene expression by cDNA microarray assay (2e); glycogen storage shown by PAS staining (2f); DiI-ac-LDL uptake in iHep cells (2g); ICG uptake in iHep cells (2h); secretory albumin protein levels as measured by ELISA during hepatic conversion (2i); and CYP metabolic activities of iHep cells (2j-1). *: $P<0.05$, t-test. All scale bars: 50 mm. Data are presented as mean±s.d. in 2i-1.

FIGS. 3a-d are diagrams and photographs showing: (a) a schematic outline of iHep cell transplantation into livers of $Fah^{-/-}Rag2^{-/-}$ mice; (b) Kaplan-Meier survival curves of primary-hepatocyte-transplanted $Fah^{-/-}Rag2^{-/-}$ mice ("Hepa-F/R," n=10), iHep-cell-transplanted $Fah^{-/-}Rag2^{-/-}$ mice ("iHep-F/R," n=12), TTF-transplanted $Fah^{-/-}Rag2^{-/-}$ mice ("TTF-F/R," n=6), and control $Fah^{-/-}Rag2^{-/-}$ mice ("FIR," n=10) after NTBC withdrawal (*, $P<0.02$, log-rank test); (c) repopulation of iHep cells in $Fah^{-/-}Rag2^{-/-}$ livers as determined by Fah immunostaining; and (d) Fah immunostaining and Y-chromosome FISH staining of serial liver sections from male $Fah^{-/-}Rag2^{-/-}$ livers transplanted with female iHep cells, where the boundary of the $Fah^+$ nodule is indicated by a dashed yellow line.

FIGS. 4a-g are diagrams and photographs showing that iHep cells restored liver functions of $Fah^{-/-}Rag2^{-/-}$ mice, including (a) representative photographs of whole livers from $Fah^{-/-}Rag2^{-/-}$ and iHep-$Fah^{-/-}Rag2^{-/-}$ mice; (b-f) diagrams showing serum levels of tyrosine (4b), phenylalanine (4c), total bilirubin (4d), ALT (4e) and AST (4f) in wild-type (n=6), Hepa-$Fah^{-/-}Rag2^{-/-}$ (n=5), iHep-$Fah^{-/-}Rag2^{-/-}$ (n=5, sera collected 8 weeks after iHep transplantation) and control $Fah^{-/-}Rag2^{-/-}$ mice (n=4, sera collected upon losing 20% of body weight). (*: P, 0.05, t-test. Data are presented as mean±s.d.).; and (g) representative photographs of iHep and PLC/PRF/5 cells (human hepatoma cell line) that were subcutaneously transplanted into the left and right flanks of NOD/SCID mice, respectively, where PLC/PRF/5-generated tumours are indicated by the dotted ovals.

FIGS. 5a-c are photographs showing that (a) hepatic marker genes Albumin and Tdo2 were induced by a combination of 14 transcription factors in 3T3 cells, wildtype MEFs and TTFs 5 days after infection; (b) wildtype TTFs underwent proliferation arrest and cell death 7 days after transduction of 14TF, while epithelial cells were formed in $p19Arf^{-/-}$ TTFs after 14TF transduction; and (c) expressions of hepatic genes Albumin, Tdo2 and Ttr were analyzed by RT-PCR in 14TF-transduced $p19^{Arf-/-}$ TTFs.

FIGS. 6a and b are photographs showing mRNA levels of exogenous hepatic transcription factors (a) and of hepatic genes (b) in individual epithelial colonies derived from 14TF-transduced $p19Arf^{-/-}$ TTFs.

FIGS. 7a-d are diagrams and photographs showing: (a) expression of indicated genes as analyzed by RT-PCR in $p19Arf^{-/-}$ TTFs after transduction by different transcription factors; (b) and (c) effects of individual factor withdrawal from 6TF and 5TF on epithelial colony formation (data are presented as mean±s.d.); and (d) stronger expression of hepatic genes (Albumin, Tdo2, Transferrin and E-cadherin) induced by the combination of Gata4, Hnf1α and Foxa3 than that of Gata4, Hnf1α and Foxa2, where endogenous Foxa2 and Foxa3 were induced by combination of Gata4, Hnf1α and Foxa3.

FIG. 8 is a set of photographs showing hepatic conversion of MEFs by Gata4, Hnf1α and Foxa3, where hepatic genes Albumin, Tdo2, Transferrin and E-cadherin were determined by RT-PCR in MEFs with overexpression of Gata4, Hnf1α and Foxa3.

FIGS. 9a-c are diagram and a set of photographs showing that p19Arf knockdown facilitates hepatic conversion of wildtype TTFs, where (a) efficient shRNA-mediated p19Arf knockdown ("p19Arf-shRNA") was confirmed by qRT-PCR in TTFs. (*: t-test, $P<0.05$); (b) TTFs with p19Arf knockdown were induced to show epithelial morphology after 3TF transduction; and (c) hepatic genes were up-regulated in p19Arf-knockdown TTFs after 3TF transduction.

FIGS. 10a-f are diagrams and photographs of hepatic gene expression study in iHep cells, where (a) that albumin positive cells were determined by flow cytometry analysis in 3TF-transduced TTFs; (b) mRNA levels of indicated genes were measured by qRT-PCR in TTF cells, primary hepatocytes cultured for 6 days ("Hepa") and iHep cells (*: t-test, $P<0.05$); (c) and (d) albumin and Hnf4α proteins were detected by immunofluorescent staining; (e) expressions of exogenous 3TF were measured by qRT-PCR during hepatic conversion; (f) five 3TF-induced iHep cell colonies were picked up for mRNA expression analysis of hepatic genes (Albumin, Transferrin, Cps1, CK8, CK18, E-cadherin, Tip1, Cldn2, Foxa2, Hnf4α and Afp) and fibroblast-enriched genes (Col1a1, Pdgfrβ, Postn, Thy1 and Csf1) by RT-PCR.

FIGS. 11 a-f are diagrams and photographs of comparison of iHep cells with other cell lineages, where (a) expressions of hepatoblast marker genes were determined by PCR during hepatic conversion; (b) iHep cells were pretreated with 50 μM 3-methylcholanthrene for 48 hours and levels of Cyp1a1, Cyp1a2, Cyp3a11 and Cyp3a13 were measured by qRT-PCR; (c) bile duct marker genes were analyzed by PCR; (d) bile duct cells formed branching structures in a 3-dimension culture system (arrow heads), while iHep cells stopped proliferation under this condition; (e) marker genes for pancreatic exocrine cells (Prss1, Cela2a and Amy2a5) and endocrine cells (Ins), Ins2 and Glucagon) were analyzed in iHep cells, TTFs, primary hepatocytes and pancreatic cells; and (f) expressions of intestine marker genes were determined by PCR. *: t-test, $P<0.05$.

FIGS. 14a-e are a diagram and a set of photographs showing: (a) repopulation of primary hepatocytes in $Fah^{-/-}Rag^{2-/-}$ livers as shown by Fah staining of the liver; (b) body weight measured every week after NTBC removal (data are presented as mean±s.d. *: $P<0.03$, t-test); (c) repopulation of iHep cells in $Fah^{-/-}Rag^{2-/-}$ livers as shown by Fah staining of repopulated iHep cells in F/R liver sections (brown staining; pictures of 4 areas were merged into one using ADOBE PHOTOSHOP (ADOBE SYSTEMS)); (d) Fah wildtype allele and p19Arf wildtype and null alleles as analyzed by PCR using genomic DNA extracted from liver sections; and (e) female iHep donor cells that were transplanted into male F/R recipient mice, where serial liver sections of 8 Fah-positive (Fah) nodules were shown (nodule #2-#9), $Fah^+$ nodules are Y-FISH negative (Y-FISH−) (nodule #2 and #3). Note the Y-FISH positive endothelial cells (arrowhead) and inflammatory cells (arrows) from host in the Fah⁺ nodules (nodule #4-#6). Yellow dash lines indicate the boundaries of Fah⁺ nodules (nodule #7-#9).

FIGS. 15a-g are diagrams and photographs for study of restoring liver functions of Fah$^{-/-}$Rag2$^{-/-}$ mice by iHep cell transplantation showing: (a) representative pictures of H&E stained liver sections from F/R and iHep-F/R mice, with arrowheads indicating dead hepatocytes in F/R livers; (b) serial liver sections stained by H&E and Fah⁺ immunostaining with H&E staining showing normal hepatic architecture formed by Fah⁺ cells (scale bars: 200 μm); (c) immunostaining for Fah and Albumin of livers re-populated by iHep cells or primary hepatocytes; (d) Fah⁺ nodules isolated by laser-captured microdissection from serial liver sections and mRNA levels of indicated genes measured in repopulated iHep cells and repopulated primary hepatocytes in F/R recipient livers; and (e-g) serum levels of ornithine, alanine and glycine in WT (n=6), Hepa-F/R (n=5), iHep-F/R (n=5, sera collected 8 weeks after iHep transplantation) and control F/R mice (n=4, sera collected upon losing 20% of body weight).*: P<0.05, t-test.

FIGS. 16a and b are photographs and a diagram showing that iHep cells are not tumorigenic after transplantation, where (a) serial sections of F/R livers 8 weeks after iHep cell transplantation were stained by Fah and Ki67 and Fah⁺ iHep cells were negatively stained for Ki67; (b) karyotypes of iHep cells were analyzed by measurement of chromosome numbers during mitosis.

FIG. 17 is a set of photographs showing expression of hepatic genes, Albumin, Afp, Transferrin, Ttr and Tat as analyzed by RT-PCR using mRNAs isolated from 293FT cells 6 days after Lentiviral infection.

FIGS. 18A-E are photographs showing that epithelial iHep cells formation was induced in human 293 FT cells (B-D) or in primary p19Arf-null mouse TTF cultures (E) by overexpression of human FOXA2, HNF1A and GATA4 (B), human FOXA3, HNF1A and GATA4 (C), mouse Foxa3, Hnf1α and Gata4 (D), and human FOXA3, HNF1A and GATA4 (E), where 293 FT cells expressing GFP was used as a control (A).

FIG. 19 is a photograph showing that overexpression of human FOXA3, HNF1A, and GATA4 induced the formation of epithelial human iHep cells from primary human fetal skin fibroblasts.

DETAILED DESCRIPTION OF THE INVENTION

Figure 12:
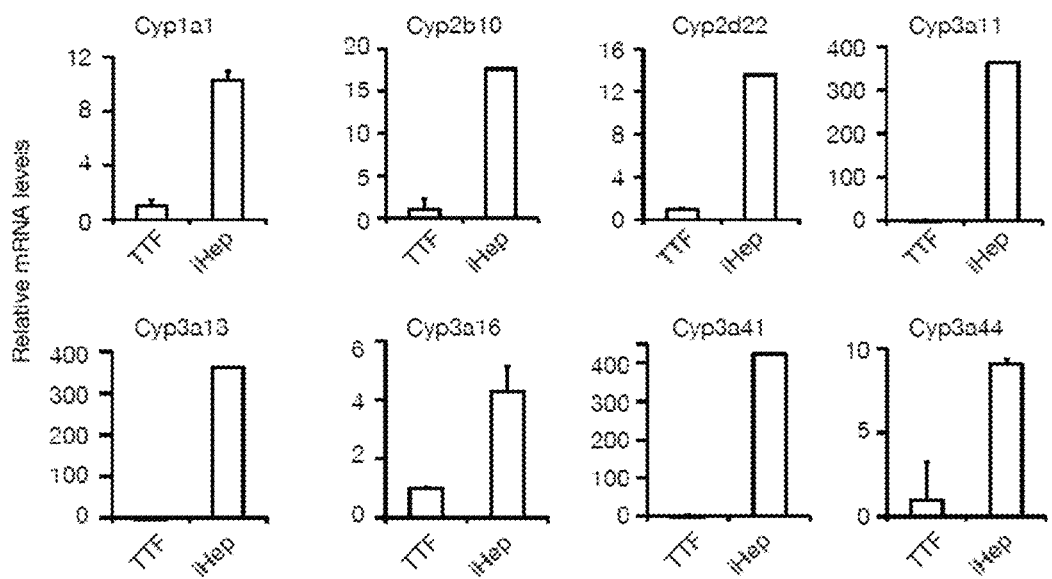
FIG. 12 is diagrams showing qRT-PCR results that confirmed up-regulated mRNA expression of several CYP enzymes in iHep cells after Phenolbarbital treatment.

This invention is based, at least in part, on unexpected discoveries that non-liver cells (e.g., adult fibroblast cells) can be converted to hepatocyte-like cells via (i) over-expressing as few as 2 (e.g., Hnf and Foxa) or 3 (Hnf, Foxa and GATA) heterologous transcription factors and (ii) decreasing expression of a cell cycle inhibitor (e.g., p19$^{Arf}$) thereby increasing cell proliferation and by-passing proliferation arrest and associated cell death.

A hepatocyte-like cell (iHep cell) refers to a cell displaying one or more properties that are characteristic of mature, parenchymal hepatocytes as disclosed below. Preferably, an iHep cell may display at least one, two, three, four, five or more of the following properties: ability to use pyruvate as a sole carbon source; phase I biotransformation capacity (e.g. ethoxyresorufin, pentoxyresorufin, testosterone); phase II biotransformation capacity (e.g. 1-chloro-2,4 dinitrobenzene, 1,2-dichloro-4-nitrobenzene, 7-chloro-4-nitrobenzene-2-oxa-1,3-diazole, estradiol, estrogen), the presence of cytochrome P450 protein and gene expression; inducibility of phase I and phase II biotransformation enzymes (e.g. beta-naphthoflavone, phenobarbital, methylcholantrene); albumin secretion, urea production, glycogen storage, the presence of the expression of one or more of endogenous ALB, AFP, gamma-glutyryltransferase, hepatocyte nuclear factor (HNF) 1α, HNF 1β, HNF 3α, HNF 3β, HNF 4, HNF-6, anti-trypsin, CX32, MRP2, C/EBPa, transthyretin, CK-18 and/or CFTR; polygonal morphology. In one embodiment, iHep cells of this invention showed an expression profile and hepatic function close to those of mature hepatocytes where some CYP genes were not induced, and CK19 and Afp were upregulated. The iHep cells are not identical to hepatocytes. The iHep cells of this invention are genetically stable and not prone to tumor formation. They can be used for disease modeling, transplantation, and tissue engineering.

As mentioned above, there is an unmet need for an unlimited source of human hepatocytes or hepatocyte-like cells. Differentiating human embryonic stem cells (hESCs) into hepatocytes or the like has been recently developed. Although these hESCs derived cells show typical morphology and phenotypes of human hepatocytes, their uses as patient-compatible hepatocytes or the like are limited by the number of hESC lines available. The success in generating induced pluripotent stem cell (iPSC) makes it possible to produce hepatocytes from patient's own cells, when iPSCs are differentiated to hepatic endoderm. Yet, cells derived from either hESC or iPSC pose the concern for contamination of undifferentiated pluripotent stem cells that could form teratoma in vivo. Multipotential mesenchymal stem cells (MSCs), which show in vitro proliferation and multiple lineage differentiations, can be differentiated in vitro into hepatocyte-like cells with appropriate hepatic gene expression and functional attributes. However, the application of MSC-derived hepatocyte-like cells is limited by the low efficiency and a mixture of differentiated cells derived.

As disclosed herein, conversion of mouse tail-tip fibroblasts to induce exogenous hepatocyte-like (iHep) cells were established by over-expression of transcription factor Hnf1α, Foxa3, Gata4 and inactivation of p19$^{Arf}$. It was found that epithelial colony from fibroblasts was induced as early as 5 days after transduction of transcription factors, and iHep cells were obtained and readily expandable. iHep cells appeared to be epigenetically stable since exogenous transcription factors were silenced after lineage conversion. Remarkably, iHep cells with expression profile close to mature hepatocytes showed multiple hepatic functions in vitro, such as glycogen storage, Albumin secretion, low-density-lipoprotein transportation and metabolism of xenobiotics. By rigorous analysis of lineage markers, fibroblasts were only converted to mature hepatic cells, but not to hepatic progenitor cells or other cell lineages.

As disclosed herein, transcription factors Foxa3 and optionally, Gata4, can act as pioneer factors to trigger a global chromatin modification during hepatic conversion (Zaret et al. Cold Spring Harb. Symp. Quant. Biol. 73, 119-126 (2008) and Cirillo et al. Mol. Cell. 9, 279-289 (2002)) and Hnf1α can stabilize the hepatic gene expression, as Hnf1α, Foxa2 and Hnf4α occupy each other's promoters and maintain the hepatic phenotype (Kyrmizi et al. Genes Dev. 20, 2293-2305 (2006) and Odom et al. Science 303, 1378-1381 (2004)). Proliferative iHep cells can be obtained by inactivating p19$^{Arf}$, a key component of the cellular senescence pathway that inhibits induced pluripotent stem cell reprogramming (Li et al. Nature 460, 1136-1139 (2009)). Inactivating other components of this pathway, such as p38 (Hui et al. Nature Genet. 39, 741-749 (2007)), can also be used to facilitate hepatic conversion as disclosed herein.

Transcription Factors Useful for the Invention

Various transcription factors can be used in this invention to generate iHep cells. Examples of them include those of the hepatocyte nuclear factor (Hnf) 1 or 4 subfamily (e.g., Hnf1α and Hnf4α), the forkhead box A protein (Foxa) family (e.g., Foxa1, Foxa2, and Foxa3), and the GATA family (e.g., GATA4). Other examples include members of the Hlf, Hhex, Jarid2, Coup-TF1, Lrh1, Fxr, and Pxr family or sub-family. Listed in Table 1 below are mouse genes encoding exemplary members of the transcription factors. Homologous from other species (e.g., human or other mammals) can also be used.

TABLE 1

| Gene Name | GenBank Number | SEQ ID NO for corresponding polypeptides |
|---|---|---|
| Hnf1α | NM_009327 | 1 |
| Foxa3 | NM_008260 | 2 |
| Gata4 | NM_008092 | 3 |
| Foxa1 | NM_008259 | 4 |
| Foxa2 | NM_010446 | 5 |
| Hnf4α | NM_008261 | 6 |
| Hnf6 | NM_008262 | 7 |
| Hlf | NM_172563 | 8 |
| Hhex | NM_008245 | 9 |
| Jarid2 | NM_021878 | 10 |
| Coup-TF1 | NM_010151 | 11 |
| Lrh1 | NM_030676 | 12 |
| Fxr | NM_009108 | 13 |
| Pxr | NM_010936 | 14 |

Mouse Hnf1α (SEQ ID NO: 1):

MVSKLSQLQTELLAALLESGLSKEALIQALGEPGPYLMVGEGPLDKGESCGGSRGDLTELPNGLGETRGSED
DTDDDGEDFAPPILKELENLSPEEAAHQKAVVESLLQEDPWRVAKMVKSYLQQHNIPQREVVDTTGLNQSHL
SQHLNKGTPMKTQKRAALYTWYVRKQREVAQQFTHAGQGGLIEEPTGDELPTKKGRRNRFKWGPASQQILFQ
AYERQKNPSKEERETLVEECNRAECIQRGVSPSQAQGLGSNLVTEVRVYNWFANRRKEEAFRHKLAMDTYNG
PPPGPGPGPALPAHSSPGLPTTTLSPSKVHGVRYGQSATSEAAEVPSSSGGPLVTVSAALHQVSPTGLEPSS
LLSTEAKLVSATGGPLPPVSTLTALHSLEQTSPGLNQQPQNLIMASLPGVMTIGPGEPASLGPTFTNTGAST
LVIGLASTQAQSVPVINSMGSSLTTLQPVQFSQPLHPSYQQPLMPPVQSHVAQSPFMATMAQLQSPHALYSH
KPEVAQYTHTSLLPQTMLITDTNLSTLASLTPTKQVFTSDTEASSEPGLHEPPSPATTIHIPSQDPSNIQHL
QPAHRLSTSPTVSSSSLVLYQSSDSNGHSHLLPSNHSVIETFISTQMASSSQ

Mouse Foxa3 (SEQ ID NO: 2):

MLGSVKMEAHDLAEWSYYPEAGEVYSPVNPVPTMAPLNSYMTLNPLSSPYPPGGLQASPLPTGPLAPPAPTA
PLGPTFPSLGTGGSTGGSASGYVAPGPGLVHGKEMAKGYRRPLAHAKPPYSYISLITMAIQQAPGKMLTLSE
IYQWIMDLFPYYRENQQRWQNSIRHSLSFNDCFVKVARSPDKPGKGSYWALHPSSGNMFENGCYLRRQKRFK
LEEKAKKGNSATSASRNGTAGSATSATTTAATAVTSPAQPQPTPSEPEAQSGDDVGGLDCASPPSSTPYFSG
LELPGELKLDAPYNFNHPFSINNLMSEQTSTPSKLDVGFGGYGAESGEPGVYYQSLYSRSLLNAS

Mouse Gata4 (SEQ ID NO: 3):

MYQSLAMAANHGPPPGAYEAGGPGAFMHSAGAASSPVYVPTPRVPSSVLGLSYLQGGGSAAAAGTTSGGSSG
AGPSGAGPGTQQGSPGWSQAGAEGAAYTPPPVSPRFSFPGTTGSLAAAAAAAAREAAAYGSGGGAAGAGLA
GREQYGRPGFAGSYSSPYPAYMADVGASWAAAAAASAGPFDSPVLHSLPGRANPGRHPNLDMFDDFSEGREC
VNCGAMSTPLWRRDGTGHYLCNACGLYHKMNGINRPLIKPQRRLSASRRVGLSCANCQTTTTTLWRRNAEGE
PVCNACGLYMKLHGVPRPLAMRKEGIQTRKRKPKNLNKSKTPAGPAGETLPPSSGASSGNSSNATSSSSSSE
EMRPIKTEPGLSSHYGHSSSMSQTFSTVSGHGPSIHPVLSALKLSPQGYASPVTQTSQASSKQDSWNSLVLA
DSHGDIITA

Mouse Foxa1: (SEQ ID NO: 4):

MLGTVKMEGHESNDWNSYYADTQEAYSSVPVSNMNSGLGSMNSMNTYMTMNTMTTSGNMTPASFNMSYANTG
LGAGLSPGAVAGMPGASAGAMNSMTAAGVTAMGTALSPGGMGSMGAQPATSMNGLGPYAAAMNPCMSPMAYA
PSNLGRSRAGGGGDAKTFKRSYPHAKPPYSYISLITMAIQQAPSKMLTLSEIYQWIMDLFPYYRQNQQRWQN
SIRHSLSFNDCFVKVARSPDKPGKGSYWTLHPDSGNMFENGCYLRRQKRFKCEKQPGAGGGSGGGGSKGGPE
SRKDPSGPGNPSAESPLHRGVHGKASQLEGAPAPGPAASPQTLDHSGATATGGASELKSPASSSAPPISSGP
GALASVPPSHPAHGLAPHESQLHLKGDPHYSFNHPFSINNLMSSSEQQHKLDFKAYEQALQYSPYGATLPAS
LPLGSASVATRSPIEPSALEPAYYQGVYSRPVLNTS

TABLE 1-continued

| Gene Name GenBank Number | SEQ ID NO for corresponding polypeptides |
|---|---|

Mouse Foxa2 (SEQ ID NO: 5):

MLGAVKMEGHEPSDWSSYYAEPEGYSSVSNMNAGLGMNGMNTYMSMSAAAMGGGSGNMSAGSMNMSSYVGAG
MSPSLAGMSPGAGAMAGMSGSAGAAGVAGMGPHLSPSLSPLGGQAAGAMGGLAPYANMNSMSPMYGQAGLSR
ARDPKTYRRSYTHAKPPYSYISLITMAIQQSPNKMLTLSEIYQWIMDLFPFYRQNQQRWQNSIRHSLSFNDC
FLKVPRSPDKPGKGSFWTLHPDSGNMFENGCYLRRQKRFKCEKQLALKEAAGAASSGGKKTAPGSQASQAQL
GEAAGSASETPAGTESPHSSASPCQEHKRGGLSELKGAPASALSPPEPAPSPGQQQQAAAHLLGPPHHPGLP
PEAHLKPEHHYAFNHPFSINNLMSSEQQHHHSHHHHQPHKMDLKAYEQVMHYPGGYGSPMPGSLAMGPVTNK
AGLDASPLAADTSYYQGVYSRPIMNSS

Mouse Hnf4α (SEQ ID NO: 6):

MRLSKTLAGMDMADYSAALDPAYTTLEFENVQVLTMGNDTSPSEGANLNSSNSLGVSALCAICGDRATGKHY
GASSCDGCKGFFRRSVRKNHMYSCRFSRQCVVDKDKRNQCRYCRLKKCFRAGMKKEAVQNERDRISTRRSSY
EDSSLPSINALLQAEVLSQQITSPISGINGDIRAKKIANITDVCESMKEQLLVLVEWAKYIPAFCELLLDDQ
VALLRAHAGEHLLLGATKRSMVFKDVLLLGNDYIVPRHCPELAEMSRVSIRILDELVLPFQELQIDDNEYAC
LKAIIFFDPDAKGLSDPGKIKRLRSQVQVSLEDYINDRQYDSRGRFGELLLLLPTLQSITWQMIEQIQFIKL
FGMAKIDNLLQEMLLGGSASDAPHTHHPLHPHLMQEHMGTNVIVANTMPSHLSNGQMCEWPRPRGQAATPET
PQPSPPSGSGSESYKLLPGAITTIVKPPSAIPQPTITKQEAI

Mouse Hnf6 (SEQ ID NO: 7):

MNAQLTMEAIGELHGVSHEPVPAPADLLGGSPHARSSVGHRGSHLPPAHPRSMGMASLLDGGSGGSDYHHHH
RAPEHSLAGPLHPTMTMACETPPGMSMPTTYTTLTPLQPLPPISTVSDKFPHHHHHHHHHHPHHHQRLAGN
VSGSFTLMRDERGLASMNNLYTPYHKDVAGMGQSLSPLSGSGLGSIHNSQQGLPHYAHPGAAMPTDKMLTPN
GFEAHHPAMLGRHGEQHLTPTSAGMVPINGLPPHHPHAHLNAQGHGQLLGTAREPNPSVTGAQVSNGSNSGQ
MEEINTKEVAQRITTELKRYSIPQAIFAQRVLCRSQGTLSDLLRNPKPWSKLKSGRETFRRMWKWLQEPEFQ
RMSALRLAACKRKEQEHGKDRGNTPKKPRLVFTDVQRRTLHAIFKENKRPSKELQITISQQLGLELSTVSNF
FMNARRRSLDKWQDEGGSNSGSSSSSSSTCTKA

Mouse Hlf (SEQ ID NO: 8):

MEKMSRQLPLNPTFIPPPYGVLRSLLENPLKLPLHPEDAFSKEKDKGKKLDDESSSPTVPQSAFLGPTLWDK
TLPYDGDTFQLEYMDLEEFLSENGIPPSPSQHDHSPHPPGLQPASSTAPSVMDLSSRATAPLHPGIPSPNCM
QSPIRPGQLLPANRNTPSPIDPDTIQVPVGYEPDPADLALSSIPGQEMFDPRKRKFSEEELKPQPMIKKARK
VFIPDDLKDDKYWARRRKNNMAAKRSRDARRLKENQTATRASFLEKENSALRQEVADLRKELGKCKNILAKY
EARHGPL

Mouse Hhex (SEQ ID NO: 9):

MQFPHPGPAAAPAVGVPLYAPTPLLQPAHPTPFYIDDILGRGPAAPTPTPTLPSPNSSFTSLVSSYRTPVYE
PTPVHPAFSHHPAAALAAAYGPSGFGGPLYPFPRTVNDYTHALLRHDPLGKPLLWSPFLQRPLHKRKGGQVR
FSNDQTVELEKKFETQKYLSPPERKRLAKMLQLSERQVKTWFQNRRAKWRRLKQENPQSNKKDALDSLDTSC
EQGQDLPSEQNKGASLDRSQCSPSPASQEDPDSEISEDSDQEVDIEGDKGYFNAG

Mouse Jarid2 (SEQ ID NO: 10):

MSKERPKRNIIQKKYDDSDGIPWSEERVVRKVLYLSLKEFKNAQKRQHGEGLAGSLKAVNGLLGNAQAKALG
PASEQSENEKDDASQVSSTSNDVSSSDFEEGPSRKRPRLQAQRKFAQSQPNSPSTTPVKIVEPLLPPPATQI
SDLSKRKPKTEDFLTFLCLRGSPALPNSMVYFGSSQDEEDVEEEDDETEDVKATTNNASSSCQSTPRKGKTH
KHVHNGHVFNGSSRSAREKEPAHKHRSKEATPGKEKHSEPRADSRREQASGAQPTAASAAASSAKGLAANHQ
PPPSHRSAQDLRKQVSKVNGVTRMSSLGAGTNSAKKIREVRPSPSKTVKYTATVTKGTVTYTKAKRELVKET
KPNHHKPSSAVNHTISGKTESSNAKTRKQVLSLGGASKSTGPAASGLKASSRLNPKSCTKEVGGRQLREGLR
NSKRRLEEAQQVDKPQSPPKKMKGVAGNAEAPGKKASAASGEKSLLNGHVKKEVPERSLERNRPKRAAAGKN
MLGKQAHGKTEGTPCENRSTSQPESSHKPHDPQGKPEKGSGKSGWAAMDEIPVLRPSAKEFHDPLIYIESVR
AQVEKYGMCRVIPPPDWRPECKLNDEMRFVTQIQHIHKLGRRWGPNVQRLACIKKHLRSQGITMDELPLIGG
CELDLACFFRLINEMGGMQQVTDLKKWNKLADMLRIPKTAQDRLAKLQEAYCQYLLSYDSLSPEEHRRLEKE
VLMEKEILEKRKGPLEGHTESDHHKFHSLPRFEPKNGLVHGVTPRNGFRSLKEVGRAPLKTGRRRLFAQEK
EVVKEEEEDKGVLNDFHKCIYKGRSVSLTTFYRTARNIMNMCFSKEPAPAEIEQEYWRLVEEKDCHVAVHCG
KVDTNTHGSGFPVGKSEPFSRHGWNLTVLPNNTGSILRHLGAVPGVTIPWLNIGMVFSTCWSRDQNHLPYI
DYLHTGADCIWYCIPAEEENKLEDVVHTLLQGNGTPGLQMLESNVMISPEVLCKKGIKVHRTVQQSGQFVVC
FPGSFVSKVCCGYNVSETVHFATTQWTSMGFETAKEMKRRHIAKPFSMEKLLYQIAQAEAKKENGPTLSTIS
ALLDELRDTELRQRRLLFEAGLHSSARYGSHDGNSTVADGKKKPRKWLQLETSERRCQICQHLCYLSMVVQE
NENVVFCLECALRHVEKQKSCRGLKLMYRYDEEQIISLVNQICGKVSGKHGGIENCLNKPTPKRGPRKRATV
DVPPSRLPSS

Mouse Coup-TF1 (SEQ ID NO: 11):

MAMVVSSWRDPQDDVAGGNPGGPNPAAQAARGGGGGEQQQAGSGAPHTPQTPGQPGAPATPGTAGDKGQGPP
GSGQSQQHIECVVCGDKSSGKHYGQFTCEGCKSFFKRSVRRNLTYTCRANRNCPIDQHHRNQCQYCRLKKCL
KVGMRREAVQRGRMPPTQPNPGQYALTNGDPLNGHCYLSGYISLLLRAEPYPTSRYGSQCMQPNNIMGIENI
CELAARLLFSAVEWARNIPFFPDLQITDQVSLLRLTWSELFVLNAAQCSMPLHVAPLLAAAGLHASPMSADR
VVAFMDHIRIFQEQVEKLKALHVDSAEYSCLKAIVLFTSDACGLSDAAHIESLQEKSQCALEEYVRSQYPNQ
PSRFGKLLLRLPSLRTVSSSVIEQLFFVRLVGKTPIETLIRDMLLSGSSFNWPYMSIQCS

TABLE 1-continued

| Gene Name GenBank Number | SEQ ID NO for corresponding polypeptides |
|---|---|

Mouse Lrh1 (SEQ ID NO: 12):

MSASLDTGDFQEFLKHGLTAIASAPGSETRHSPKREEQLREKRAGLPDRHRRPIPARSRLVMLPKVETEAPG
LVRSHGEQGQMPENMQVSQFKMVNYSYDEDLEELCPVCGDKVSGYHYGLLTCESCKGFFKRTVQNQKRYTCI
ENQNCQIDKTQRKRCPYCRFKKCIDVGMKLEAVRADRMRGGRNKFGPMYKRDRALKQQKKALIRANGLKLEA
MSQVIQAMPSDLTSAIQNIHSASKGLPLSHVALPPTDYDRSPFVTSPISMTMPPHSSLHGYQPYGHFPSRAI
KSEYPDPYSSSPESMMGYSYMDGYQTNSPASIPHLILELLKCEPDEPQVQAKIMAYLQQEQSNRNRQEKLSA
FGLLCKMADQTLFSIVEWARSSIFFRELKVDDQMKLLQNCWSELLILDHIYRQVAHGKEGTIFLVTGEHVDY
STIISHTEVAFNNLLSLAQELVVRLRSLQFDQREFVCLKFLVLFSSDVKNLENLQLVEGVQEQVNAALLDYT
VCNYPQQTEKFGQLLLRLPEIRAISKQAEDYLYYKHVNGDVPYNNLLIEMLHAKRA

Mouse Fxr (SEQ ID NO: 13):

MVMQFQGLENPIQISLHHSHRLSGFVPEGMSVKPAKGMLTEHAAGPLGQNLDLESYSPYNNVPFPQVQPQIS
SSSYYSNLGFYPQQPEDWYSPGIYELRRMPAETGYQGETEVSEMPVTKKPRMAAASAGRIKGDELCVVCGDR
ASGYHYNALTCEGCKGFFRRSITKNAVYKCKNGGNCVMDMYMRRKCQECRLRKCKEMGMLAECLLTEIQCKS
KRLRKNVKQHADQTANEDDSEGRDLRQVTSTTKFCREKTELTADQQTLLDYIMDSYNKQRMPQEITNKILKE
EFSAEENFLILTEMATSHVQILVEFTKKLPGFQTLDHEDQIALLKGSAVEAMFLRSAEIFNKKLPAGHADLL
EERIRKSGISDEYITPMFSFYKSVGELKMTQEEYALLTAIVILSPDRQYIKDREAVEKLQEPLLDVLQKLCK
MYQPENPQHFACLLGRLTELRTFNHHHAEMLMSWRVNDHKFTPLLCEIWDVQ

Mouse Pxr (SEQ ID NO: 14):

MRPEESWSRVGLVQCEEADSALEEPINVEEEDGGLQICRVCGDKANGYHFNVMTCEGCKGFFRRAMKRNVRL
RCPFRKGTCEITRKTRRQCQACRLRKCLESGMKKEMIMSDAAVEQRRALIKRKKREKIEAPPPGGQGLTEEQ
QALIQELMDAQMQTFDTTFSHFKDFRLPAVFHSGCELPEFLQASLLEDPATWSQIMKDRVPMKISLQLRGED
GSIWNYQPPSKSDGKEIIPLLPHLADVSTYMFKGVINFAKVISYFRDLPIEDQISLLKGATFEMCILRFNTM
FDTETGTWECGRLAYCFEDPNGGFQKLLLDPLMKFHCMLKKLQLHKEEYVLMQAISLFSPDRPGVVQRSVVD
QLQERFALTLKAYIECSRPYPAHRFLFLKIMAVLTELRSINAQQTQQLLRIQDSHPFATPLMQELFSSTDG

Listed below are some of the cDNA sequences that can be used in this invention.

cDNA sequence for mouse Foxa3 gene, which encodes mouse Foxa3 protein:
(SEQ ID NO: 19)

```
001 gcgggactcc cgggctgtgt gcctcaggtc ggaactcggg gctagtgcct gtagagagac
061 cgaagcactc ggttccccca gggggggcctc agcctgggtg tgtgggggcg caggcccgg
121 ggatgctggg ctcagtgaag atggaggctc atgacctggc cgagtggagc tactaccgg
181 aggcgggcga ggtgtattct ccagtgaatc ctgtgcccac catggcccct ctcaactcct
241 acatgacctt gaacccactc agctctccct accctcccgg agggcttcag gcctccccac
301 tgcctacagg accctggca cccccagccc ccactgcgcc cttggggccc accttccaa
361 gcttgggcac tggtggcagc accggaggca gtgcttccgg gtatgtagcc ccagggcccg
421 ggcttgtaca tggaaaagag atggcaaagg ggtaccggcg gccactggcc cacgccaaac
481 caccatattc ctacatctct ctcataacca tggctattca gcaggctcca ggcaagatgc
541 tgaccctgag tgaaatctac caatggatca tggacctctt cccgtactac cgggagaacc
601 agcaacgttg gcagaactcc atccggcatt cgctgtcctt caatgactgc ttcgtcaagg
661 tggcacgctc cccagacaag ccaggcaaag ctcctactg ggccttgcat cccagctctg
721 ggaacatgtt tgagaacggc tgctatctcc gccggcagaa gcgcttcaag ctggaggaga
781 aggcaaagaa aggaaacagc gccacatcgg ccagcaggaa tggtactgcg gggtcagcca
841 cctctgccac cactacagct gccactgcag tcacctcccc ggctcagccc cagcctacgc
901 catctgagcc cgaggcccag agtggggatg atgtggggg tctggactgc gcctcacctc
961 cttcgtccac accttatttc agcggcctgg agctcccggg ggaactaaag ttggatgcgc
1021 cctataactt caaccaccct ttctctatca caacctgat gtcagaacag acatcgacac
1081 cttccaaact ggatgtgggg tttgggggct acggggctga gagtggggag cctggagtct
1141 actaccagag cctctattcc cgctctctgc ttaatgcatc ctagcagcgc aattgggaac
```

-continued

```
1201 gccatgatgg gcgtgggctg caacgttctt gggctctgat ctttctggtt acactttgct 1261 tgtcccatta attaacatct tatttggtct attactgtga tatgacccat tggctactgt 1321 ggtaactgcc atggactctt tggtaggcct agggttgggg tattaggaag cagatgcgt 1381 ttggaagtgc tgcgaaggtg gtcatgttgg acatattgtg aaggcagtta gactggtgta 1441 ctatgaaagc tgccatatta agtgaagcca ttgggtgatt gatccactgg gtgcctgatg 1501 gtcgtgatgt tggatgacac atgtctggtc ctttggatga tgtgttggac atcttgattg 1561 acctttgag tatgtgacag aacacatctt ctttggctca ttttatcctg ggatcgcctc 1621 ttttttttcc tcttcttttt ctttttcttt ttctttttt cttttccttt tttcttttt 1681 ttttcttttt tggcagactt cttggttcag cagatgccaa attggccacc atatcacatg 1741 gtgtcttttt tgacattctg gatgcatgga aggtcactgt attggcaagg tgacatctca 1801 gcatgctgct atgcaccaag atagatggtt accacaggcc tgccatcacc atctccttgg 1861 tggaggttgg gtgaggggaa gaggtgagca gaccctatga gttttctctg aagcccatcc 1921 ccaccctgtc tgtgagaaag ggctagtgtg ggtgtcggga gttcctactg aggtcaagtt 1981 cttgtctggg gcttgggaat actgcctgtg tttggccatt aaaaaggcac catctccat
``` cDNA sequence for mouse HNF1a gene, which encodes mouse HNF1a protein:

(SEQ ID NO: 20)

```
   1 aaacagagca ggcagggcc ctgattcact ggccgctggg gccagggttg ggggctgggg 61 gtgcccacag agcttgacta gtgggatttg ggggggcagt gggtgcagcg agcccggtcc 121 gttgactgcc agcctgccgg caggtagaca ccggccgtgg gtggggagg cggctagctc 181 agtggccttg ggccgcgtgg cctggtggca gcggagccat ggtttctaag ctgagccagc 241 tgcagacgga gctcctggct gccctgctcg agtctggcct gagcaaagag gccctgatcc 301 aggccttggg ggagccaggg ccctacctga tggttggaga gggtcccctg acaaggggg 361 agtcctgcgg tgggagtcga ggggacctga ccgagttgcc taatggcctt ggagaaacgc 421 gtggctctga agatgacacg gatgacgatg gggaagactt cgcgccaccc attctgaaag 481 agctggagaa cctcagccca gaggaggcag cccaccagaa agccgtggtg gagtcacttc 541 ttcaggagga cccatggcgc gtggcgaaga tggtcaagtc gtacttgcag cagcacaaca 601 tcccccagcg ggaggtggtg gacaccacgg gtctcaacca gtcccacctg tcacagcacc 661 tcaacaaggg cacacccatg aagacacaga gcgggccgc tctgtacacc tggtacgtcc 721 gcaagcagcg agaggtggct cagcaattca cccacgcagg gcagggcgga ctgattgaag 781 agcccacagg cgatgagctg ccaactaaga ggggcgtag gaaccggttc aagtggggcc 841 ccgcatccca gcagatcctg ttccaggcct acgagaggca aaaaaacccc agcaaggaag 901 agcgagagac cttggtggag gagtgtaata gggcggagtg catccagagg ggggtgtcac 961 catcgcaggc ccaggggcta ggctccaacc ttgtcacgga ggtgcgtgtc tacaactggt 1021 ttgccaaccg gcgcaaggag gaagccttcc ggcacaagtt ggccatggac acctataacg 1081 gacctccacc gggccaggc ccgggccctg cgctgcctgc tcacagttcc cccggcctgc 1141 ccacaaccac cctctctccc agtaaggtcc acggtgtacg gtacggacag tctgcaacca 1201 gtgaggcagc cgaggtgccc tccagcagcg gaggtccctt agtcacagtg tctgcggcct 1261 tacaccaagt atccccaca ggcctggagc ccagcagcct gctgagcaca gaggccaagc 1321 tggtctcagc cacgggggt ccctgcctc ccgtcagcac cctgacagca ctgcacagct 1381 tggagcagac atctccgggt ctcaaccagc agccgcagaa ccttatcatg gcctcgctac 1441 ctgggtcat gaccatcggg cccggggagc ctgcctccct gggacccacg ttcacgaaca
```

-continued

```
1501 cgggcgcctc caccctggtt atcggtctgg cctccactca ggcacagagc gtgcctgtca 1561 tcaacagcat ggggagtagc ctgaccacgc tgcagccggt ccagttttcc caaccactgc 1621 atccctccta tcagcagcct ctcatgcccc ccgtacagag ccacgtggcc cagagcccct 1681 tcatggcaac catggcccag ctgcagagcc cccacgcctt atacagccac aagcctgagg 1741 tggcccagta cacgcacacc agcctgctcc cgcagaccat gttgatcaca gacaccaacc 1801 tcagcaccct tgccagcctc acacccacca agcaggtctt cacctcagac acagaggcct 1861 ccagtgagcc cgggcttcac gagccaccct ctccagccac caccatccac atccccagcc 1921 aggacccgtc gaacatccag cacctgcagc ctgctcaccg gctcagcacc agtcccacag 1981 tgtcctccag cagcctggtg ttgtatcaga gttccgactc caacgggcac agccacctgc 2041 tgccatccaa ccatagtgtc atcgagactt ttatctccac ccagatggcc tcctcttccc 2101 agtaaccgtg gtgactgcct cccaggagct gggtccccag ggcctgcact gcctgcatag 2161 ggggtgagga gggccgcagc cacactgcct ggaggatatc tgagcctgcc atgccacctg 2221 acacaggctg ctggccttcc cagaagtcta cgcattcatt gacactgctg ctcctccatc 2281 atcaggaagg gatggctctg aggtgtctca gcctgacaag cgagcctcga ggagctggag 2341 gacggcccaa tctgggcagt attgtggacc accatccctg ctgtttagaa taggaaattt 2401 aatgcttggg acaggagtgg ggaagctcgt ggtgcccgca ccccccagt cagagcctgc 2461 aggccttcaa ggatctgtgc tgagctctga ggccctagat caacacagct gcctgctgcc 2521 tcctgcacct ccccaggcca ttccaccctg caccagagac ccacgtgcct gtttgaggat 2581 taccctcccc accacgggga tttcctaccc agctgttctg ctaggctcgg gagctgaggg 2641 gaagccactc ggggctctcc taggctttcc cctaccaagc catcccttct cccagcccca 2701 ggactgcact tgcaggccat ctgttccctt ggatgtgtct tctgatgcca gcctggcaac 2761 ttgcatccac tagaaaggcc atttcagggc tcgggttgtc atccctgttc cttaggacct 2821 gcaactcatg ccaagaccac accatggaca atccactcct ctgcctgtag gcccctgaca 2881 acttccttcc tgctatgagg gagacctgca gaactcagaa gtcaaggcct gggcagtgtc 2941 tagtggagag ggtaccaaga ccagcagaga gaagccacct aagtggcctg ggggctagca 3001 gccattctga gaaatcctgg gtcccgagca gcccagggaa acacagcaca catgactgtc 3061 tcctcgggcc tactgcaggg aacctggcct tcagccagct cctttgtcat cctggactgt 3121 agcctacggc caaccataag tgagcctgta tgtttattta acttttagta aagtcagtaa 3181 aaagcaaaaa aaaaaaaaa aaa
``` cDNA sequence for mouse Gata4 gene, which encodes mouse Gata4 protein:

(SEQ ID NO: 21)
```
  1 aggggacaag ccggaggccc gcagagtggc cgcccgaggc tcagccgcag ttgcagctcc 61 gcggactcac ggagatcgcg ccggttttct gggaaactgg agctggccag gactgccgct 121 tcgcttcgaa gggaccgggc cctctttgtc attcttcgct ggagccgctc tggagctagc 181 agctgcgcct gggtgtgtag caggcagaaa gcaaggacta ggcttcttta gccggtgggt 241 gatccgaagg cctgctcagg gtgttcgaga ccagcctgga ctgcgtctgg cacctccag 301 cctctgggcc ctggaataga gtccgccctc ccgcacgatt tctggagcaa ccgcaaatcc 361 aatttgggat tttctttttc ctgagcaaac cagagcctag aggtttctgc tttgatgctg 421 gatttaattc gtatatattt tgagcgagtt gggcctctcc tcgttttttg atctccggtt 481 gttttttttt tgggggggg gttagttttt gggtttttgt tttgttttgt tttgttttga 541 tttttggtga cagttccgca cacccgcatt ctagttcttg tctgcctcgt gctcagagct
```

-continued

```
 601 tggggcgatg taccaaagcc tggccatggc cgccaaccac ggccccccgc ccggcgccta
 661 cgaagcaggt ggccctggcg ccttcatgca cagcgcgggc gccgcgtcct cgcccgtcta
 721 cgtgcccact ccgcgggtgc cgtcctctgt gctgggcctg tcctacctgc agggcggtgg
 781 cagtgccgct gcagctggaa ccacctcggg tggcagctcc ggggccggcc cgtcgggtgc
 841 agggcctggg acccagcagg gtagccctgg ctggagccaa gctggagccg agggagccgc
 901 ctacaccccg ccgcccgtgt ccccgcgctt ctctttcccg gggactactg ggtccctggc
 961 ggccgctgcc gccgctgccg cagcccggga agctgcagcc tacggcagtg gcggcggggc
1021 ggcgggcgct ggtctggctg gccgagagca gtacgggcgt ccgggcttcg ccggctccta
1081 ctccagcccc tacccagcct acatggccga cgtgggagca tcctgggccg cagccgctgc
1141 cgcctctgcc ggcccttcg acagcccagt cctgcacagc ctgcctggac gggccaaccc
1201 tggaagacac cccaatctcg atatgtttga tgacttctca gaaggcagag agtgtgtcaa
1261 ttgtggggcc atgtccaccc cactctggag gcgagatggg acgggacact acctgtgcaa
1321 tgcctgtggc ctctatcaca agatgaacgg catcaaccgg cccctcatta gcctcagcg
1381 ccgcctgtcc gcttcccgcc gggtaggcct ctcctgtgcc aactgccaga ctaccaccac
1441 cacgctgtgg cgtcgtaatg ccgagggtga gcctgtatgt aatgcctgcg gcctctacat
1501 gaagctccat ggggttccca ggcctcttgc aatgcggaag gagggattc aaaccagaaa
1561 acggaagccc aagaacctga ataaatctaa gacgccagca ggtcctgctg gtgagaccct
1621 ccctccctcc agtggtgcct ccagcggtaa ctccagcaat gccactagca gcagcagcag
1681 cagtgaagag atgcgcccca tcaagacaga gcccgggctg tcatctcact atgggcacag
1741 cagctccatg tcccagacat tcagtactgt gtccggccac gggccctcca tccatccagt
1801 gctgtctgct ctgaagctgt ccccacaagg ctatgcatct cctgtcactc agacatcgca
1861 ggccagctcc aagcaggact cttggaacag cctggtcctg gctgacagtc atgggacat
1921 aatcaccgcg taatcagcgc ccccccttcc ctcttcaaat tcctgctcgg acttgggacg
1981 tgggggccag caaagtaaaa ggctggggca cccttggcca gcccctttgt ctgggaacaa
2041 ctcctgaaga caactgggt agaacttgaa gttgttgaca atcacttagg gatatgggtg
2101 ttccggggttg ttcaaacacc tttccaggtg gagcactgga aaagcctgcg ttcttacaga
2161 gaagcccacc ttggctgcaa gcacagcaca gtgaggcaag agacttcttc cttccttatt
2221 ctccacctgc ctgtccagga cagacacata atctccttca ccccagctcc ccacccagtt
2281 gtggtggtgg gttttttcttt gtgatcctag agtggctgta ggggcggagg cttcaagaca
2341 ccatctacag tctgagcagg gtgtctactt gttgtagact agacatagaa gccctgccct
2401 tgtccaacac tccccttgct tgaggcatgg cacatctctg catgtcccat accagatctg
2461 actccaaagt gctgggttca atgcagatgt tactgaatgc ttcctgggga gattaggtga
2521 ggggaaggca catcacccat cacacagaat agcttcatca aatcgcagcc tggccatggt
2581 gccttcccct cctctcccag gaacatcaaa ccccttgctc tccagcctga acatctaccc
2641 tctgcaaaag tagagcccag ttgtgcagct aatgccacta ggtgctatat cccagcatcc
2701 ttttcacccc ttcacacaca ggggttccaa ggaggaacaa aacctgctac caaagcagcc
2761 ttggtgacta tggctcatct gcacctcagg gggtggggga gggccctctg gaggttgtgt
2821 ctacagcaca atactgttcc caggactcta gcttgcttgc cccgagcctg ccaagccaag
2881 ccctcttaag tcagacagtt acctggctct gggactttct ccagcacaga tcctttgtct
2941 agaaaataca gactgtttgc aaaataaatt caaagcagaa acaactaaag gaaatttgtg
3001 aaaggacaaa ggtgatagac gggagaagat gtccccaggg ctggcgggac agtcatgata
```

-continued

```
3061 gcagctgtcc taggattggc ctccctccca tctcccacca ttactggggc tcccagagat 3121 tcttccttgt cctcatcacc cacagagctg tagccaactg tggcattact ttattttacc 3181 caaaattccc agccccaccc ctaaaccttg ctggccgtag cagagaatag cttcgaacca 3241 agattctgtt gtaatcattt tcgctgtttc tccctcaagg ccgccttccc catgcctgcc 3301 cctcctccac aacccgttaa cattgtctta aggtgaaatg gctgtaaaat cagtatttaa 3361 ctaataaatt tatctgtatt cctgtttcct ccg
``` cDNA sequence for human Foxa3 gene, which encodes human Foxa3 protein (NM_004497.2):

(SEQ ID NO: 22)

```
   1 ggagcccggg gcgggcgagg gcggggtgt cccggctata aagcgtggcc gcctcccgcg 61 gcgctcggga cagccgtacc ccgggcggtc ggacgggcgg gcgccggtgg gagctcgggc 121 cgtgcccgct gagagatcca gagcgctccg ttcccccggg gccggagcgg gggcgggtgg 181 gggcgtaagc ccgggggatg ctgggctcag tgaagatgga ggcccatgac ctggccgagt 241 ggagctacta cccggaggcg ggcgaggtct actcgccggt gacccccagtg cccaccatgg 301 ccccccctcaa ctcctacatg accctgaatc ctctaagctc tccctatccc cctgggggc 361 tccctgcctc cccactgccc tcaggacccc tggcaccccc agcacctgca gcccccctgg 421 ggcccacttt cccaggcctg ggtgtcagcg gtggcagcag cagctccggg tacggggccc 481 cgggtcctgg gctggtgcac gggaaggaga tgccgaaggg gtatcggcgg ccctggcac 541 acgccaagcc accgtattcc tatatctcac tcatcaccat ggccatccag caggcgccgg 601 gcaagatgct gaccttgagt gaaatctacc agtggatcat ggacctcttc ccttactacc 661 gggagaatca gcagcgctgg cagaactcca ttcgccactc gctgtctttc aacgactgct 721 tcgtcaaggt ggcgcgttcc ccagacaagc ctggcaaggg ctcctactgg gccctacacc 781 ccagctcagg gaacatgttt gagaatggct gctacctgcg ccgccagaaa cgcttcaagc 841 tggaggagaa ggtgaaaaaa gggggcagcg gggctgccac caccaccagg aacgggacag 901 ggtctgctgc ctcgaccacc accccgcgg ccacagtcac ctccccgccc cagccccgc 961 ctccagcccc tgagcctgag gcccagggcg gggaagatgt gggggctctg gactgtggct 1021 cacccgcttc ctccacaccc tatttcactg gcctggagct cccaggggag ctgaagctgg 1081 acgcgcccta caacttcaac caccctttct ccatcaacaa cctaatgtca gaacagacac 1141 cagcacctcc caaactggac gtggggttg ggggctacgg ggctgaaggt ggggagcctg 1201 gagtctacta ccagggcctc tattcccgct ctttgcttaa tgcatcctag caggggttgg 1261 gaacatggtg tgggtatgg ctggagctca ccacgaag ctcttggggc ctgatccttc 1321 tggtgacact tcacttgtcc cattggttaa catctgggtg ggtctattac ttactgtgat 1381 gactgctgtc tcagtgggca tggtgttgat ccacggggta ctgtgataac caccatggat 1441 acattttggt ggcccactgg gtactgtgag gactgctaca ttgatggatg ttattggcta 1501 atccactgca tggtttgatg gccaccatct cggttggccc tttgggtgtg atggtgatag 1561 catttcagtg acatcttctt tggcccccc cattaggtgc tgtgcccact tctttttttgg 1621 tgtacttggc acagtaggtg ccaagttggc caccattctg tgtaacacct ttttggccc 1681 attgggtgct tgatggaca tcatactggg taggtgacaa cgtcagtggg ccaccatgtg 1741 ccatgatggc tgctgcagcc ccgtgttggc catgtcgtca ccattctctc tggcatgggt 1801 tgggtagggg atggaggtga gaatactcct tggttttctc tgaagcccac cctttccccc 1861 aactctggtc caggagaaac cagaaaaggc tggttagggt gtggggaatt tctactgaag 1921 tctgattctt tcccgggaag cggggtactg gctgtgttta atcattaaag gtaccgtgtc
```

-continued

```
1981 cgcctcttaa aaaaaaaaaa aaaaaaaaaa aaaaaaaaaa aaaaaaaaaa 2041 aaaaaa
``` cDNA sequence for human HNF1a gene, which encodes human HNF1a protein (NM_000545.5):

(SEQ ID NO: 23)

```
   1 cgtggccctg tggcagccga gccatggttt ctaaactgag ccagctgcag acggagctcc 61 tggcggccct gctcgagtca gggctgagca agaggcact gatccaggca ctgggtgagc 121 cggggcccta cctcctggct ggagaaggcc ccctggacaa gggggagtcc tgcggcggcg 181 gtcgagggga gctggctgag ctgcccaatg ggctggggga gactcggggc tccgaggacg 241 agacggacga cgatggggaa gacttcacgc cacccatcct caaagagctg gagaacctca 301 gccctgagga ggcggcccac cagaaagccg tggtggagac ccttctgcag gaggacccgt 361 ggcgtgtggc gaagatggtc aagtcctacc tgcagcagca acatcccca cagcgggagg 421 tggtcgatac cactggcctc aaccagtccc acctgtccca cacctcaac aagggcactc 481 ccatgaagac gcagaagcgg ccgcccctgt acacctggta cgtccgcaag cagcgagagg 541 tggcgcagca gttcacccat gcagggcagg gagggctgat tgaagagccc acaggtgatg 601 agctaccaac caagaagggg cggaggaacc gtttcaagtg gggcccagca tcccagcaga 661 tcctgttcca ggcctatgag aggcagaaga ccctagcaa ggaggagcga gagacgctag 721 tggaggagtg caatagggcg gaatgcatcc agagagggt gtccccatca caggcacagg 781 ggctgggctc caacctcgtc acggaggtgc gtgtctacaa ctggtttgcc aaccggcgca 841 aagaagaagc cttccggcac aagctggcca tggacacgta cagcgggccc ccccaggggc 901 caggcccggg acctgcgctg cccgctcaca gctcccctgg cctgcctcca cctgccctct 961 cccccagtaa ggtccacggt gtgcgctatg acagcctgc gaccagtgag actgcagaag 1021 taccctcaag cagcggcgt cccttagtga cagtgtctac acccctccac caagtgtccc 1081 ccacgggcct ggagcccagc acagcctgc tgagtacaga agccaagctg gtctcagcag 1141 ctggggggcc cctccccct gtcagcaccc tgacagcact gcacagcttg gagcagacat 1201 ccccaggcct caaccagcag ccccagaacc tcatcatggc ctcacttcct ggggtcatga 1261 ccatcgggcc tggtgagcct gcctccctgg gtcctacgtt caccaacaca ggtgcctcca 1321 ccctggtcat cggcctggcc tccacgcagg cacagagtgt gccggtcatc aacagcatgg 1381 gcagcagcct gaccacccctg cagcccgtcc agttctccca gccgctgcac cctcctacc 1441 agcagccgct catgccacct gtgcagagcc atgtgaccca gagccccttc atggccacca 1501 tggctcagct gcagagcccc cacgccctct acagccacaa gccgaggtg gcccagtaca 1561 cccacacggg cctgctcccg cagactatgc tcatcaccga caccaccaac ctgagcgccc 1621 tggccagcct cacgcccacc aagcaggtct tcacctcaga cactgaggcc tccagtgagt 1681 ccgggcttca cacgccggca tctcaggcca ccacctcca cgtcccagc caggaccctg 1741 ccggcatcca gcacctgcag ccggcccacc ggctcagcgc cagccccaca gtgtcctcca 1801 gcagcctggt gctgtaccag agctcagact ccagcaatgg ccagagccac tgctgccat 1861 ccaaccacag cgtcatcgag accttcatct ccacccagat ggcctcttcc tcccagtaac 1921 cacggcacct gggccctggg gcctgtactg cctgcttggg gggtgatgag ggcagcagcc 1981 agccctgcct ggaggacctg agcctgccga gcaaccgtgg cccttcctgg acagctgtgc 2041 ctcgctcccc actctgctct gatgcatcag aaagggaggg ctctgaggcg ccccaacccg 2101 tggaggctgc tcggggtgca caggaggggg tcgtggagag ctaggagcaa agcctgttca 2161 tggcagatgt aggagggact gtcgctgctt cgtgggatac agtcttctta cttggaactg
```

-continued

```
2221 aagggggcgg cctatgactt gggcaccccc agcctgggcc tatggagagc cctgggaccg 2281 ctacaccact ctggcagcca cacttctcag gacacaggcc tgtgtagctg tgacctgctg 2341 agctctgaga ggccctggat cagcgtggcc ttgttctgtc accaatgtac ccaccgggcc 2401 actccttcct gccccaactc cttccagcta gtgacccaca tgccatttgt actgaccccca 2461 tcacctactc acacaggcat ttcctgggtg gctactctgt gccagagcct ggggctctaa 2521 cgcctgagcc cagggaggcc gaagctaaca gggaaggcag gcagggctct cctggcttcc 2581 catccccagc gattccctct cccaggcccc atgacctcca gctttcctgt atttgttccc 2641 aagagcatca tgcctctgag gccagcctgg cctcctgcct ctactgggaa ggctacttcg 2701 gggctgggaa gtcgtcctta ctcctgtggg agcctcgcaa cccgtgccaa gtccaggtcc 2761 tggtggggca gctcctctgt ctcgagcgcc ctgcagaccc tgcccttgtt tggggcagga 2821 gtagctgagc tcacaaggca gcaaggcccg agcagctgag cagggccggg gaactggcca 2881 agctgaggtg cccaggagaa gaaagaggtg accccagggc acaggagcta cctgtgtgga 2941 caggactaac actcagaagc ctgggggcct ggctggctga gggcagttcg cagccaccct 3001 gaggagtctg aggtcctgag cactgccagg agggacaaag gagcctgtga acccaggaca 3061 agcatggtcc cacatccctg ggcctgctgc tgagaacctg gccttcagtg taccgcgtct 3121 accctgggat tcaggaaaag gcctggggtg acccggcacc ccctgcagct tgtagccagc 3181 cggggcgagt ggcacgttta tttaacttttt agtaaagtca aggagaaatg cggtggaaaa 3241 a
``` cDNA sequence for human Gata4 gene, which encodes human Gata4 protein (NM_002052.3):

(SEQ ID NO: 24)

```
   1 ttggaggcgg ccggcgcagg ggccgcgaga ggcttcgtcg ccgctgcagc tccgggggct 61 cccaggggag cgtgcgcgga acctccaggc ccagcaggac cccggctgcg gcgaggagga 121 aggagccagc ctagcagctt ctgcgcctgt ggccgcgggt gtcctggagg cctctcggtg 181 tgacgagtgg gggacccgaa ggctcgtgcg ccacctccag gcctggacgc tgccctccgt 241 cttctgcccc caataggtgc gccggacctt caggccctgg ggtgaattca gctgctccta 301 catcagcttc cggaaccacc aaaaattcaa attgggattt ccggagtaa acaagagcct 361 agagcccttt gctcaatgct ggatttaata cgtatatatt tttaagcgag ttggtttttt 421 cccctttgat ttttgatctt cgcgacagtt cctcccacgc atattatcgt tgttgccgtc 481 gtttttctctc cccgcgtggc tccttgacct gcgagggaga gagaggacac cgaagccggg 541 agctcgcagg gaccatgtat cagagcttgg ccatggccgc caaccacggg ccgcccccccg 601 gtgcctacga ggcgggcggc cccggcgcct tcatgcacgg cgcgggcgcc gcgtcctcgc 661 cagtctacgt gcccacaccg cgggtgccct cctccgtgct gggcctgtcc tacctccagg 721 gcggaggcgc gggctctgcg tccggaggcg cctcgggcgg cagctccggt ggggccgcgt 781 ctggtgcggg gccgggacc cagcagggca gcccggatg gagccaggcg ggagccgacg 841 gagccgctta caccccgccg ccggtgtcgc gcgcttctc cttcccgggg accaccgggt 901 ccctggcggc cgccgccgcc gctgccgcgg cccgggaagc tgcggcctac agcagtggcg 961 gcggagcggc gggtgcgggc ctggcgggcc gcgagcagta cgggcgcgcc ggcttcgcgg 1021 gctcctactc cagcccctac ccggcttaca tggccgacgt gggcgcgtcc tgggccgcag 1081 ccgccgccgc ctccgccggc cccttcgaca gccggtcct gcacagcctg cccggccggg 1141 ccaaccggcc cgccgacac cccaatctcg atatgtttga cgacttctca gaaggcagag 1201 agtgtgtcaa ctgtgggggct atgtccaccc cgctctggag gcgagatggg acgggtcact

```

-continued

```
1261 atctgtgcaa cgcctgcggc ctctaccaca agatgaacgg catcaaccgg ccgctcatca
1321 agcctcagcg ccggctgtcc gcctcccgcc gagtgggcct ctcctgtgcc aactgccaga
1381 ccaccaccac cacgctgtgg cgccgcaatg cggagggcga gcctgtgtgc aatgcctgcg
1441 gcctctacat gaagctccac ggggtcccca ggcctcttgc aatgcggaaa gaggggatcc
1501 aaaccagaaa acggaagccc aagaacctga ataaatctaa gacaccagca gctccttcag
1561 gcagtgagag ccttcctccc gccagcggtg cttccagcaa ctccagcaac gccaccacca
1621 gcagcagcga ggagatgcgt cccatcaaga cggagcctgg cctgtcatct cactacgggc
1681 acagcagctc cgtgtcccag acgttctcag tcagtgcgat gtctggccat gggccctcca
1741 tccaccctgt cctctcggcc ctgaagctct ccccacaagg ctatgcgtct cccgtcagcc
1801 agtctccaca gaccagctcc aagcaggact cttggaacag cctggtcttg gccgacagtc
1861 acggggacat aatcactgcg taatcttccc tcttccctcc tcaaattcct gcacggacct
1921 gggacttgga ggatagcaaa gaaggaggcc ctgggctccc aggggccggc ctcctctgcc
1981 tggtaatgac tccagaacaa caactgggaa gaaacttgaa gtcgacaatc tggttagggg
2041 aagcgggtgt tggattttct cagatgcctt tacacgctga tgggactgga gggagcccac
2101 ccttcagcac gagcacactg catctctcct gtgagttgga gacttctttc caagatgtc
2161 cttgtccct gcgttcccca ctgtggccta gaccgtgggt tttgcattgt gtttctagca
2221 ccgaggatct gagaacaagc ggagggccgg gccctgggac ccctgctcca gcccgaatga
2281 cggcatctgt ttgccatgta cctggatgcg acgggcccct ggggacaggc ccttgcccca
2341 tccatccgct tgaggcatgg caccgccctg catccctaat accaaatctg actccaaaat
2401 tgtggggtgt gacatacaag tgactgaaca cttcctgggg agctacaggg gcacttaacc
2461 caccacagca cagcctcatc aaaatgcagc tggcaacttc tcccccaggt gccttccccc
2521 tgctgccggc ctttgctcct tcacttccaa catctctcaa aataaaaatc cctcttcccg
2581 ctctgagcga ttcagctctg cccgcagctt gtacatgtct ctcccctggc aaaacaagag
2641 ctgggtagtt tagccaaacg gcacccctc gagttcactg cagacccttc gttcaccgtg
2701 tcacacatag aggggttctg agtaagaaca aaacgttctg ctgctcaagc cagtctggca
2761 agcactcagc ccagcctcga ggtccttctg gggagagtgt aagtggacag agtcctggtc
2821 agggggcagg agtgtcccaa gggctggccc acctgctgtc tgtctgctcc tcctagccct
2881 tggtcagatg gcagccagag tccctcagga cctgcagcct cgccccggca gaagtctttt
2941 gtccaggagg caaaaagcca gagattctgc aacacgaatt cgaagcaaac aaacacaaca
3001 caacagaatt cctggaaaga agacgactgc taagacacgg caggggggcc tggagggagc
3061 ctccgactct gagctgctcc gggatctgcc gcgttctcct ctgcacattg ctgtttctgc
3121 ccctgatgct ggagctcaag gagactcctt cctctttctc agcagagctg tagctgactg
3181 tggcattact acgcctcccc acacgcccag acccctcact ccaaaatcct actggctgta
3241 gcagagaata ccttttgaacc aagattctgt tttaatcatc atttacattg tttttcttcca
3301 aaggcccct cgtatacccct ccctaaccca caaacctgtt aacattgtct taaggtgaaa
3361 tggctggaaa atcagtattt aactaataaa tttatctgta ttcctcttaa aaaaaaaaa
```

Human Foxa3 protein:

(SEQ ID NO: 25)

MLGSVKMEAHDLAEWSYYPEAGEVYSPVTPVPTMAPLNSYMTLNPLSSPYPPGGLPASPLPSGPLAPPAPAA

PLGPTFPGLGVSGGSSSSGYGAPGPGLVHGKEMPKGYRRPLAHAKPPYSYISLITMAIQQAPGKMLTLSEIY

QWIMDLFPYYRENQQRWQNSIRHSLSFNDCFVKVARSPDKPGKGSYWALHPSSGNMFENGCYLRRQKRFKLE

-continued

```
EKVKKGGSGAATTTRNGTGSAASTTTPAATVTSPPQPPPPAPEPEAQGGEDVGALDCGSPASSTPYFTGLEL

PGELKLDAPYNFNHPFSINNLMSEQTPAPPKLDVGFGGYGAEGGEPGVYYQGLYSRSLLNAS

Human HNF1a protein:
                                                                (SEQ ID NO: 26)
MVSKLSQLQTELLAALLESGLSKEALIQALGEPGPYLLAGEGPLDKGESCGGGRGELAELPNGLGETRGSED

ETDDDGEDFTPPILKELENLSPEEAAHQKAVVETLLQEDPWRVAKMVKSYLQQHNIPQREVVDTTGLNQSHL

SQHLNKGTPMKTQKRAALYTWYVRKQREVAQQFTHAGQGGLIEEPTGDELPTKKGRRNRFKWGPASQQILFQ

AYERQKNPSKEERETLVEECNRAECIQRGVSPSQAQGLGSNLVTEVRVYNWFANRRKEEAFRHKLAMDTYSG

PPPGPGPGPALPAHSSPGLPPPALSPSKVHGVRYGQPATSETAEVPSSSGGPLVTVSTPLHQVSPTGLEPSH

SLLSTEAKLVSAAGGPLPPVSTLTALHSLEQTSPGLNQQPQNLIMASLPGVMTIGPGEPASLGPTFTNTGAS

TLVIGLASTQAQSVPVINSMGSSLTTLQPVQFSQPLHPSYQQPLMPPVQSHVTQSPFMATMAQLQSPHALYS

HKPEVAQYTHTGLLPQTMLITDTTNLSALASLTPTKQVFTSDTEASSESGLHTPASQATTLHVPSQDPAGIQ

HLQPAHRLSASPTVSSSSLVLYQSSDSSNGQSHLLPSNHSVIETFISTQMASSSQ

Human Gata4 protein:
                                                                (SEQ ID NO: 27)
MYQSLAMAANHGPPPGAYEAGGPGAFMHGAGAASSPVYVPTPRVPSSVLGLSYLQGGGAGSASGGASGGSSG

GAASGAGPGTQQGSPGWSQAGADGAAYTPPPVSPRFSFPGTTGSLAAAAAAAAAREAAAYSSGGGAAGAGLA

GREQYGRAGFAGSYSSPYPAYMADVGASWAAAAAASAGPFDSPVLHSLPGRANPAARHPNLDMFDDFSEGRE

CVNCGAMSTPLWRRDGTGHYLCNACGLYHKMNGINRPLIKPQRRLSASRRVGLSCANCQTTTTTLWRRNAEG

EPVCNACGLYMKLHGVPRPLAMRKEGIQTRKRKPKNLNKSKTPAAPSGSESLPPASGASSNSSNATTSSSEE

MRPIKTEPGLSSHYGHSSSVSQTFSVSAMSGHGPSIHPVLSALKLSPQGYASPVSQSPQTSSKQDSWNSLVL

ADSHGDIITA
```

Members of the Hnf 1 subfamily are transcription factors that contain a POU-homeodomain and bind to DNA as homodimers. Among them, Hnf1α is highly expressed in the liver and is involved in the regulation of the expression of several liver-specific genes. Members of the Hnf4 subfamily are nuclear receptors and bind to DNA either as homodimers or RXR heterodimers. Hnf4α, as a transcription factor, binds DNA as a homodimer, and controls the expression of several genes, including Hnf1α. This transcription factor plays a role in development of the liver, kidney, and intestines. Alternative splicing of this gene results in multiple transcript variants.

Forkhead box proteins are a family of transcription factors that play important roles in regulating the expression of genes involved in cell growth, proliferation, differentiation, and longevity. Many forkhead box proteins are important to embryonic development. They are a subgroup of the helix-turn-helix class of proteins. The defining feature of these proteins is the forkhead box, a sequence of 80 to 100 amino acids forming a motif that binds to DNA. This forkhead motif is also known as the winged helix due to the butterfly-like appearance of the loops in the protein structure of the domain. Foxa1, Foxa2, and Foxa3, also known as Hnf3α, β, and γ, respectively, are members of the forkhead class of DNA-binding proteins. They are transcriptional activators for liver-specific transcripts such as albumin and transthyretin, and they also interact with chromatin.

GATA transcription factors are a family of zinc finger transcription factors. Members of this family recognize the GATA motif which is present in the promoters of many genes. Among them, GATA4 protein is known to regulate genes involved in embryogenesis and in myocardial differentiation and function. Mutations in this gene have been associated with cardiac septal defects.

As used herein, a particular transcription factor polypeptide(s) (e.g., a Hnf polypeptide, a Foxa polypeptide, a GATA4 polypeptide) refer a member(s) of a particular transcription factor family (e.g., one of the above-mentioned families), which include the corresponding transcription factor(s) described above, their homologous, polypeptide(s) having sequences thereof, and their mutant forms that retain substantial their transcription factor functions.

As disclosed herein, a forced expression of members of two or three of the above transcription factor families or subfamilies was sufficient to convert non-liver cells (such as adult fibroblast cells) to iHep cells. Accordingly, this invention provides agents that can convert non-liver cells to iHep cells, thereby supplying an unlimited cell source for modeling and understanding liver diseases, drug efficacy and toxicity testing, and cell replacement therapy.

Both polypeptides of the aforementioned transcription factors and nucleic acid encoding the polypeptides can be used to practice the invention. While many polypeptide preparations can be used, a highly purified or isolated polypeptide is preferred. The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (e.g., glycosylation or phosphorylation).

The peptide, polypeptide, or protein "of this invention" include recombinantly or synthetically produced fusion or chimeric versions of any of the aforementioned transcription factors, having the particular domains or portions that bind to the DNA site of the transcription factor and regulates the expression of a target gene of the transcription factor. The term also encompasses polypeptides that have an added amino-terminal methionine (useful for expression in prokaryotic cells).

Within the scope of this invention are fusion proteins containing one or more of the afore-mentioned sequences and a heterologous sequence. A "chimeric" or "fusion" refers to the combination of amino acid sequences of different origin in one polypeptide chain by in-frame combination of their coding nucleotide sequences. The term explicitly encompasses internal fusions, i.e., insertion of sequences of different origin within a polypeptide chain, in addition to fusion to one of its termini. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

An "isolated" or "purified" peptide, polypeptide, or protein refers to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein described in the invention can be purified from a natural source, produced by recombinant DNA techniques, or by chemical methods.

A "recombinant" peptide, polypeptide, or protein refers to a peptide, polypeptide, or protein produced by recombinant DNA techniques; i.e., produced from cells transformed by an exogenous DNA construct encoding the desired peptide. A "synthetic" peptide/polypeptide/protein refers to a peptide/polypeptide/protein prepared by chemical synthesis. The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified.

"Overexpression" refers to the expression of a RNA or polypeptide or protein encoded by a DNA introduced into a host cell, wherein the RNA or polypeptide or protein is either not normally present in the host cell, or wherein the RNA or polypeptide or protein is present in said host cell at a higher level than that normally expressed from the endogenous gene encoding the RNA or polypeptide or protein.

The amino acid composition of each of the above-mentioned peptides/polypeptides/proteins may vary without disrupting their transcription factor functions—the ability to bind to a DNA site and enhance or inhibit the respective target gene expression. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in one of the above-described transcription factors (e.g., SEQ ID NOs: 1-14) is preferably replaced with another amino acid residue from the same side chain family. Alternatively, mutations can be introduced randomly along all or part of the sequences, such as by saturation mutagenesis, and the resultant mutants can be screened for the ability to bind to the respective DNA site(s) and trigger the respective cellular response to identify mutants that retain the activity as descried below in the examples.

A functional equivalent of a peptide, polypeptide, or protein of this invention refers to a polypeptide derivative of the peptide, polypeptide, or protein, e.g., a protein having one or more point mutations, insertions, deletions, truncations, a fusion protein, or a combination thereof. It retains substantially the activity to of the above-mentioned transcription factors. The isolated polypeptide of this invention can contain one of SEQ ID NOs: 1-14, or a functional equivalent or fragment thereof. In general, the functional equivalent is at least 75% (e.g., any number between 75% and 100%, inclusive, e.g., 70%, 80%, 85%, 90%, 95%, and 99%) identical to one of SEQ ID NOs: 1-14.

A polypeptide described in this invention can be obtained as a recombinant polypeptide. For example, to prepare a recombinant polypeptide, a nucleic acid encoding it can be linked to another nucleic acid encoding a fusion partner, e.g., glutathione-s-transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention. Alternatively, the peptides/polypeptides/proteins of the invention can be chemically synthesized (see e.g., Creighton, "Proteins: Structures and Molecular Principles," W.H. Freeman & Co., NY, 1983). For additional guidance, skilled artisans may consult Ausubel et al. (Current Protocols in Molecular Biology and Short Protocols in Molecular Biology, 3rd Ed. 1987 & 1995), Sambrook et al. (Molecular Cloning, A Laboratory Manual, Cold Spring Harbor Press, Cold Spring Harbor, N.Y., 1989), and chemical synthesis Gait, M. J. Ed. (Oligonucleotide Synthesis, IRL Press, Oxford, 1984).

Due to their functions as transcription factors, the above-disclosed polypeptides can be associated with, e.g., conjugated or fused to, one or more of an amino acid sequence comprising a nuclear localization signal (NLS), a cell-penetrating peptide (CPP) sequence, and the like. In this manner, a composition of the invention as discussed below can include a transport enhancer. For example, the composition may include a penetration enhancing agent, such as MSM, for the delivery of the transcription factors or related therapeutic polypeptides to a cell and/or through the cell membrane and into the nucleus of the cell. The transcription factors then function to regulate transcription of target genes, thereby resulting in an induction of iHep cells. The transcription factors may be delivered by itself or as a fusion with one or more of an NLS, CPP, and/or other domains. See, e.g., Tachikawa et al. PNAS (2004) vol. 101, no. 42:15225-15230.

A cell-penetrating peptide (CPP) generally consists of less than 30 amino acids and has a net positive charge. CPPs internalize in living animal cells in vitro and in vivo in an endocytotic or receptor/energy-independent manner. There are several classes of CPPs with various origins, from totally protein-derived CPPs via chimeric CPPs to completely synthetic CPPs. Examples of CPPs are known in the art. See, e.g., U.S. Application Nos. 20090099066 and 20100279918. It is know that CPPs can delivery an exogenous protein to various cells.

Although the above-described transcription factors to be delivered to a cell may be fusion proteins including a NLS and/or CPP, in certain instances, the protein does not include an NLS and/or a CPP as the transport enhancer may serve the function of delivering the biologically active agent directly to the cell, and/or through the cell membrane into the cytoplasm of the cell and/or into the nucleus of the cell as desired. For instance, in certain instances, it may be desirable to deliver a biologically active protein to the cell wherein the protein is not conjugated or fused to another molecule. In such an instance, any biologically active protein may be delivered directly in conjunction with the transport enhancer.

All of naturally occurring versions, genetic engineered versions, and chemically synthesized versions of the above-mentioned transcription factors can be used to practice the invention disclosed therein. Polypeptides obtained by recombinant DNA technology may have the same amino acid sequence as a naturally occurring version (e.g., one of SEQ ID NOs: 1-14) or a functionally equivalent thereof. They also include chemically modified versions. Examples of chemically modified polypeptides include polypeptides subjected to conformational change, addition or deletion of a side chain, and those to which a compound such as polyethylene glycol has been bound. Once purified and tested by standard methods or according to the method described in the examples below or other methods known in the art, the polypeptides can be included in suitable composition.

For expressing the above-mentioned transcription factors, the invention provides a nucleic acid that encodes any of the polypeptides mentioned above. Preferably, the nucleotide sequences are isolated and/or purified. A nucleic acid refers to a DNA molecule (e.g., but not limited to, a cDNA or genomic DNA), an RNA molecule (e.g., but not limited to, an mRNA), or a DNA or RNA analog. A DNA or RNA analog can be synthesized from nucleotide analogs. The nucleic acid molecule can be single-stranded or double-stranded. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The present invention also provides recombinant constructs having one or more of the nucleotide sequences described herein. Example of the constructs include a vector, such as a plasmid or viral vector, into which a nucleic acid sequence of the invention has been inserted, in a forward or reverse orientation. In a preferred embodiment, the construct further includes regulatory sequences, including a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook et al. (2001, Molecular Cloning: A Laboratory Manual, Cold Spring Harbor Press).

Examples of expression vectors include chromosomal, nonchromosomal and synthetic DNA sequences, e.g., derivatives of or Simian virus 40 (SV40), bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the polypeptides described above can be inserted into an appropriate restriction endonuclease site(s) by procedures known in the art. Such procedures and related sub-cloning procedures are within the scope of those skilled in the art.

The nucleic acid sequence in the aforementioned expression vector is preferably operatively linked to an appropriate transcription control sequence (promoter) to direct mRNA synthesis. Examples of such promoters include: the retroviral long terminal (LTR) or SV40 promoter, the *E. coli* lac or trp promoter, the phage lambda PL promoter, and other promoters known to control expression of genes in prokaryotic or eukaryotic cells or viruses. The expression vector can also contain a ribosome binding site for translation initiation, and a transcription terminator. The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in *E. coli*.

The vector containing the appropriate nucleic acid sequences as described above, as well as an appropriate promoter or control sequence, can be employed to transform an appropriate host to permit the host to express the polypeptides described above (e.g., one of SEQ ID NOs: 1-14). Such vectors can be used in gene therapy. Examples of suitable expression hosts include bacterial cells (e.g., *E. coli, Streptomyces, Salmonella typhimurium*), fungal cells (yeast), insect cells (e.g., *Drosophila* and *Spodoptera frugiperda* (Sf9)), animal cells (e.g., CHO, COS, and HEK 293), adenoviruses, and plant cells. The selection of an appropriate host is within the scope of those skilled in the art. In some embodiments, the present invention provides methods for producing the above mentioned polypeptides by transfecting a host cell with an expression vector having a nucleotide sequence that encodes one of the polypeptides. The host cells are then cultured under a suitable condition, which allows for the expression of the polypeptide.

As mentioned above, a nucleic acid sequence of this invention can be a DNA or RNA. The terms "RNA," "RNA molecule," and "ribonucleic acid molecule" are used interchangeably herein, and refer to a polymer of ribonucleotides. The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA also can be chemically synthesized. DNA and RNA can be single-stranded (i.e., ssRNA and ssDNA, respectively) or multi-stranded (e.g., double-stranded, i.e., dsRNA and dsDNA, respectively).

Starting Cells

As disclosed herein, the invention provides methods of generating iHep cells from non-liver cells (i.e., the starting cells). In one example, the methods involve introducing into starting cells heterologous transcription factors discussed above or nucleic acids encoding them so that the starting cells over-express the transcription factors. See, e.g., FIG. 1a. The modified starting cells are then cultured for a period of time, e.g., 14-21 days to generate iHep cells.

Various cells from a subject or animal can be used as the starting cells. In some embodiments, the starting cells are stem cells. The stem cells useful for the method described herein include but not limited to embryonic stem cell, mesenchymal stem cells, bone-marrow derived stem cells, hematopoietic stem cells, chrondrocytes progenitor cells, epidermal stem cells, gastrointestinal stem cells, neural stem cells, hepatic stem cells, adipose-derived mesenchymal stem cells, pancreatic progenitor cells, hair follicular stem cells, endothelial progenitor cells, and smooth muscle progenitor cells. The stem cells can be pluripotent or multipotent. In some embodiments, the stem cell is an adult, fetal or embryonic stem cell. The stem cells can be isolated from umbilical, placenta, amniotic fluid, chorion villi, blastocysts, bone marrow, adipose tissue, brain, peripheral blood, blood vessels, skeletal muscle, and skin.

In some embodiments, the starting cells are differentiated cells. Examples include a fibroblast, an epithelium cell, a blood cell, a neuron, an embryonic cell, or a cell derived from a tissue or organ of a subject. These differentiated cells differ from stem cells in that differentiated cells generally do not undergo self-renewing proliferation while stem cells can undergo self-renewing cell division to give rise to phenotypically and genotypically identical daughters for an indefinite time and ultimately can differentiate into at least one final cell type.

The terms "proliferation" and "expansion" as used interchangeably herein refer to an increase in the number of cells of the same type by division. The term "differentiation" refers to a developmental process whereby cells become specialized for a particular function, for example, where cells acquire one or more morphological characteristics and/or functions different from that of the initial cell type. The term includes both lineage commitment and terminal differentiation processes. Differentiation may be assessed, for example, by monitoring the presence or absence of lineage markers, using immunohistochemistry or other procedures known to a skilled in the art. Differentiated progeny cells derived from progenitor cells may be, but are not necessarily, related to the same germ layer or tissue as the source tissue of the stem cells. For example, neural progenitor cells and muscle progenitor cells can differentiate into hematopoietic cell lineages.

To convert the differentiated cells to iHep cells, one needs to reprogram the differentiated cells so that they proliferate. This can be achieved by inactivating or down-regulating one or more components of the cellular senescence pathway that inhibits induced pluripotent stem cell reprogramming, such as $p19^{Arf}$ and p38 (Li, H. et al. Nature 460, 1136-1139 (2009); Hui, L. et al. Nature Genet. 39, 741-749 (2007)). Listed below are the polypeptide and cDNA sequences for one exemplary $p19^{Arf}$ (GenBank NM_009877):

```
                                                       (SEQ ID NO: 17)
MGRRFLVTVRIQRAGRPLQERVFLVKFVRSRRPRTASCALAFVNMLLRLERILRRGPHRNPGPGDDDGQRSR

SSSSAQLRCRFELRGPHYLLPPGARRSAGRLPGHAGGAARVRGSAGCARCLGSPAARLGPRAGTSRHRAIFA

FRWVLFVFRWVVFVYRWERRPDRRA
```

```
                                                       (SEQ ID NO: 18)
  1 tctcgaggtg cctcaacgcc gaaggggctg ggggcggcgc ttctcacctc gcttgtcaca 61 gtgaggccgc cgctgaggga gtacagcagc gggagcatgg gtcgcaggtt cttggtcact 121 gtgaggattc agcgcgcggg ccgcccactc caagagaggg ttttcttggt gaagttcgtg 181 cgatcccgga gacccaggac agcgagctgc gctctggctt tcgtgaacat gttgttgagg 241 ctagagagga tcttgagaag agggccgcac cggaatcctg gaccaggtga tgatgatggg 301 caacgttcac gtagcagctc ttctgctcaa ctacggtgca gattcgaact gcgaggaccc 361 cactaccttc tcccgcccgg tgcacgacgc agcgcgggaa ggcttcctgg acacgctggt 421 ggtgctgcac gggtcagggg ctcggctgga tgtgcgcgat gcctggggtc gcctgccgct 481 cgacttggcc caagagcggg gacatcaaga catcgtgcga tatttgcgtt ccgctgggtg 541 ctctttgtgt tccgctgggt ggtctttgtg taccgctggg aacgtcgccc agaccgacgg 601 gcatagcttc agctcaagca cgcccagggc cctggaactt cgcggccaat cccaagagca 661 gagctaaatc cggcctcagc ccgccttttt cttcttagct tcacttctag cgatgctagc 721 gtgtctagca tgtggcttta aaaaatacat aataatgctt tttttgcaat cacgggaggg 781 agcagaggga gggagcagaa ggagggaggg agggagggag ggacctggac aggaaaggaa 841 tggcatgaga aactgagcga aggcggccgc gaagggaata atggctggat tgtttaaaaa 901 aataaaataa agatactttt taaaatgtc
```

Various means can be used for that purpose. In one embodiment, one can use the RNA interference (RNAi) technology or antisense technology. For example, one can generate a nucleic acid sequence that encode a small interference RNA (e.g., an RNAi agent) that targets one or more of genes encoding a component of the cellular senescence pathway and inhibits its expression or activity.

The term "RNAi agent" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein or RNA) is down-regulated. Generally, an interfering RNA ("iRNA") is a double stranded short-interfering RNA (siRNA), short hairpin RNA (shRNA), or single-stranded micro-RNA (miRNA) that results in catalytic degradation of specific mRNAs, and also can be used to lower or inhibit gene expression.

The term "short interfering RNA" or "siRNA" (also known as "small interfering RNAs") refers to an RNA agent, preferably a double-stranded agent, of about 10-50 nucleotides in length, preferably between about 15-25 nucleotides, more preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

The term "shRNA" refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

The term "miRNA" or "microRNA" refers to an RNA agent, preferably a single-stranded agent, of about 10-50 nucleotides in length, preferably between about 15-25 nucleotides in length, more preferably about 17, 18, 19, 20, 21, 22, 23, 24, or 25 nucleotides in length, which is capable of directing or mediating RNA interference. Naturally-occurring miRNAs are generated from stem-loop precursor RNAs (i.e., pre-miRNAs) by Dicer. The term microRNA (or "miRNA") is used interchangeably with the term "small temporal RNA" (or "stRNA") based on the fact that naturally-occurring microRNAs (or "miRNAs") have been found to be expressed in a temporal fashion (e.g., during development).

Thus, also within the scope of this invention is utilization of RNAi featuring degradation of RNA molecules (e.g., within a cell). Degradation is catalyzed by an enzymatic, RNA-induced silencing complex (RISC). A RNA agent having a sequence sufficiently complementary to a target RNA sequence (e.g., one or more of the above-mentioned genes of the cellular senescence pathway) to direct RNAi means that the RNA agent has a homology of at least 50%, (e.g., 50%, 60%, 70%, 80%, 90%, 95%, 98%, 99%, or 100% homology) to the target RNA sequence so that the two are sufficiently complementary to each other to hybridize and trigger the destruction of the target RNA by the RNAi machinery (e.g., the RISC complex) or process. A RNA agent having a "sequence sufficiently complementary to a target RNA sequence to direct RNAi" also means that the RNA agent has a sequence sufficient to trigger the translational inhibition of the target RNA by the RNAi machinery or process. A RNA agent also can have a sequence sufficiently complementary to a target RNA encoded by the target DNA sequence such that the target DNA sequence is chromatically silenced. In other words, the RNA agent has a sequence sufficient to induce transcriptional gene silencing, e.g., to down-modulate gene expression at or near the target DNA sequence, e.g., by inducing chromatin structural changes at or near the target DNA sequence.

The above-mentioned polynucleotides can be delivered to cells in vitro or in vivo using polymeric, biodegradable microparticle or microcapsule delivery devices known in the art. Another way to achieve uptake of the polynucleotides is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of naked DNA (i.e., without a delivery vehicle) to an intramuscular, intradermal, or subcutaneous site is another means to achieve in vivo expression.

siRNA, miRNA, and asRNA (antisense RNA) molecules can be designed by methods well known in the art. siRNA, miRNA, and asRNA molecules with homology sufficient to provide sequence specificity required to uniquely degrade any RNA can be designed using programs known in the art, including, but not limited to, those maintained on websites for AMBION, Inc. and DHARMACON, Inc. Systematic testing of several designed species for optimization of the siRNA, miRNA, and asRNA sequences can be routinely performed by those skilled in the art. Considerations when designing short interfering nucleic acid molecules include, but are not limited to, biophysical, thermodynamic, and structural considerations, base preferences at specific positions in the sense strand, and homology. These considerations are well known in the art and provide guidelines for designing the above-mentioned RNA molecules.

An antisense polynucleotide (preferably DNA) of the present invention can be any antisense polynucleotide so long as it possesses a base sequence complementary or substantially complementary to that of the DNA encoding a key component of the cellular senescence pathway that inhibits induced pluripotent stem cell reprogramming and capable of suppressing expression of the component polypeptide. The base sequence can be at least about 70%, 80%, 90%, or 95% homology to the complement of the DNA encoding the polypeptide. These antisense DNAs can be synthesized using a DNA synthesizer.

The antisense DNA of the present invention may contain changed or modified sugars, bases or linkages. The antisense DNA, as well as the RNAi agent mentioned above, may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like. The inhibitory action of the antisense DNA can be examined using a cell-line or animal based gene expression system of the present invention in vivo and in vitro.

The above-discussed nucleic acids encoding one or more of the polypeptides mentioned above or RNAi agents can be cloned in a vector for delivering to cells in vitro or in vivo. For in vivo uses, the delivery can target a specific tissue or organ (e.g., liver). Targeted delivery involves the use of vectors (e.g., organ-homing peptides) that are targeted to specific organs or tissues after systemic administration. For example, the vector can have a covalent conjugate of avidin and a monoclonal antibody to a liver specific protein.

In certain embodiments, the present invention provides methods for in vivo production of the above-mentioned iHep cells. Such method would achieve its therapeutic effect by introduction of the nucleic acid sequences into cells or tissues of a human or a non-human animal in need of an increase in liver function. Delivery of the nucleic acid sequences can be achieved using a recombinant expression vector such as a chimeric virus or a colloidal dispersion system. Preferred for therapeutic delivery of the nucleic acid sequences is the use of targeted liposomes.

Various viral vectors which can be utilized for gene therapy disclosed herein include, adenovirus, herpes virus, vaccinia, or, preferably, an RNA virus such as a retrovirus and a lentivirus. Preferably, the retroviral vector is a lentivirus or a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes.

Recombinant lentivirus has the advantage of gene delivery into either dividing or non-dividing mammalian cells. The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with ViraPower™.

All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using a target-specific antibody or hormone that has a receptor in the target. Those of skill in the art will recognize that specific polynucleotide sequences can be inserted into the retroviral genome or attached to a viral envelope to allow target specific delivery of the retroviral vector.

Another targeted system for delivery of nucleic acids is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA, and intact virions can be encapsulated within the aqueous interior and delivered to cells in a biologically active form. Methods for efficient gene transfer using a liposome vehicle are known in the art. The composition of the liposome is usually a combination of phospholipids, usually in combination with steroids, especially cholesterol. Other phospholipids or other lipids may also be used. The physical charac-teristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidyl-ethanolamine, sphingolipids, cerebrosides, and gangliosides. Exemplary phospholipids include egg phosphatidylcholine, dipalmitoylphosphatidylcholine, and distearoyl-phosphatidylcholine. The targeting of liposomes is also possible based on, for example, organ-specificity, cell-specificity, and organelle-specificity and is known in the art.

When used in vivo, it is desirable to use a reversible delivery-expression system. To that end, the Cre-loxP or FLP/FRT system and other similar systems can be used for reversible delivery-expression of one or more of the above-described nucleic acids. See WO2005/112620, WO2005/039643, U.S. Applications 20050130919, 20030022375, 20020022018, 20030027335, and 20040216178. In particular, the reversible delivery-expression system described in US Application NO 20100284990 can be used to provide a selective or emergency shut-off.

Cell Conversion

To covert the starting cells to iHep cells, the starting cells are cultured in culture medium, which is a nutrient-rich buffered aqueous solution capable of sustaining cell growth. Suitable culture media include but not limited to high glucose Dulbecco's Modified Eagle's Medium (DMEM), DMEM/F-15, Liebovitz L-15, RPMI 1640, Iscove's modified Dubelcco's media (IMDM), and Opti-MEM SFM. Chemically defined medium comprises a minimum essential medium such as Iscove's Modified Dulbecco's Medium (IMDM), supplemented with human serum albumin, human Ex Cyte lipoprotein, transferrin, insulin, vitamins, essential and non essential amino acids, sodium pyruvate, glutamine and a mitogen. A mitogen refers to an agent that stimulates cell division of a cell. An agent can be a chemical, usually some form of a protein that encourages a cell to commence cell division, triggering mitosis. In one embodiment, serum free media such as those described in WO96/39487, and the "complete media" as described in U.S. Pat. No. 5,486,359. In one preferred embodiment, one can use modified Block's medium supplemented with 0.1 mM dexamethasone, 20 μg $l^{-1}$ TGF-α, 10 μg $l^{-1}$ EGF, 4.2 mgl$^{-1}$ insulin, 3.8 mgl$^{-1}$ human transferrin and 5 μg $l^{-1}$ sodiumselenite.

The starting cells are plated for culturing and differentiation onto an adherent substrate. In general, adherent substrates may be any substantially hydrophilic substrate. Adherent substrate surfaces may be generated via surface coating, e.g., coating of the polymeric or treated polymeric surfaces as above. In a non-limiting example, the coating may involve suitable poly-cations, such as, e.g., poly-ornithine or poly-lysine. For example, a coating can contain one or more components of extracellular matrix, e.g., the ECM proteins fibrin, laminin, collagen, preferably collagen type 1, glycosaminoglycans, e.g., heparin or heparan sulphate, fibronectin, gelatine, vitronectin, elastin, tenascin, aggrecan, agrin, bone sialoprotein, cartilage matrix protein, fibrinogen, fibulin, mucins, entactin, osteopontin, plasminogen, restrictin, serglycin, SPARC/osteonectin, versican, thrombo-spondin 1, or cell adhesion molecules including cadherins, connexins, selectins, by themselves or in various combinations.

In a preferred embodiment, the coating contains collagen, e.g., collagen type 1. Such coating may be particularly preferred during the differentiation protocol, since collagen, especially, collagen type 1, has been shown to aid maintenance of hepatocyte function, differentiation state and hepatic gene transcription.

After culturing for a period of time, the cultured cell population contains iHep cells. It shall be understood that the cultured cell population encompasses the progeny of a starting cell population obtainable as above, or the progeny of a fraction of the said cell population. Such progeny may be a non-clonal line, i.e., containing the offspring of multiple cells or cells from multiple colonies of a starting cell population obtainable as above; or such progeny may be a clonal subline, i.e., derived from a single cell or a single colony of the starting cell population.

Then, one can obtain a sample of the cultured cell population and confirm their status by examining one or more markers indicative of a hepatocyte-phenotype. The iHep cells generated according to the methods described herein should express characteristic markers indicative of liver function. For example, the cells are expected to express enzymes and other polypeptides associated with carbohydrate, protein, and lipid metabolism. In one embodiment, they express a polypeptide associated with glycogen storage, glucose-6-phosphatase activity, decomposition of red blood cells, or plasma protein synthesis. In another, a cell of the invention expresses a polypeptide associated with urea production or synthesis of bile. In yet another embodiment, the cell expresses a polypeptide associated with cytochrome p450 (CYP3A4) activity, which is responsible for xenobiotic detoxification. In some other embodiments, the cell expresses arginase I, which functions in physiologic detoxification and urea production.

The expression of a hepatocyte phenotype in a cell of the invention may be evaluated by analyzing mRNA. In some embodiments, the mRNAs of key enzymes and proteins expressed in the hepatocyte-like cell are evaluated by quantitative reverse transcriptase polymerase chain reaction (qRT-PCR). Alternatively, iHep cells are characterized for a hepatocyte phenotype by analyzing the expression of hepatocyte markers (e.g., polypeptides characteristically expressed in hepatocytes by an immunoassay, such as an immunocytochemical assay or a Western blot. Examples of useful marks are described in Tables 2 and 3 and in the examples below.

One can also confirm the iHep cell status by evaluating their biological functions as shown in the examples below. More specifically, the cells can be evaluated for glycogen storage using Periodic Acid Schiff (PAS) functional staining for glycogen granules (Thompson S W. in Selected Histochemical and Histopathological Methods, C. C. Tomas, Sprungfield, Ill., 1966; Sheehan D C. and Hrapchak, B B. in Theory and Practice of Histotechnology, 2nd Ed., Battelle memorial Institute, Columbus, Ohio, 1987)), for urea production using colorimetrically (Miyoshi et al., 1998, J Biomater Sci Polym Ed 9: 227-237), for bile secretion by fluorescein diacetate time lapse assay (Gebhart et al. J. Cell Sci. 1982, 56233-244), for lipid synthesis by oil red O staining, and for glycogen synthesis (Passonneau et al. 1974, Anal. Biochem. 60:405-415).

Once the hepatocyte phenotype is confirmed, the iHep cells can be further purified or enriched according to the method described in the examples below or other methods known in the art. The resulting purified or enriched cell population contains at least 60%, e.g., at least 65%, 70%, 75%, 80%, 85%, 90%, 95%, 99% of iHep cells. The cells can be used in various ways as disclosed below.

Uses of iHep Cells

The above-described iHep cells, or a cell population containing them, or the progenies thereof, can be used in a variety of applications. One example is treating diseases or liver metabolic deficiencies, e.g., liver metabolic deficiencies, liver degenerative diseases or fulminant liver failure, liver infections diseases, etc. via transplantation or implantation. Other examples include elucidating the mechanism of liver diseases and infections; screening cytotoxic compounds, carcinogens, mutagens growth/regulatory factors, pharma-ceutical compounds, etc., in vitro; evaluating metabolism, pharmacogenetics, or toxicity of an agent (e.g., a new or known drug); studying the pharmacological mechanism by which drugs and/or growth factors operate; diagnosing and monitoring cancer in a patient; gene therapy; and the production of biologically active products. Additional examples include uses in preparation of bio-artificial liver devices and liver assist devices.

The cells of this invention as used herein refers to any of the staring cells to which one or more of the above-mentioned heterologous transcription factors have been introduced, as well as progenies of the cells such as the iHep cells and progeny thereof. Progenies as used herein includes cells derived from a parent, staring, or found cell via cell division or cell fusion with other cell(s).

Treatment of Liver Diseases

In an aspect, the invention provides methods for treating liver diseases or conditions. Also, the invention provides uses for the manufacture of a medicament for treating such liver diseases or conditions using the iHep cells disclosed herein (including iHep cells from humans and non-human animals) or the progeny thereof.

Such diseases may include disorders affecting liver tissue, and conditions affecting the hepatocyte viability and/or function (e.g., birth defects, the effect of a disease condition, the effect of trauma, toxic effects, viral infections, etc). Examples of the liver diseases or conditions include genetic liver diseases (e.g., Alagille syndrome), carbohydrate metabo-lism disorders (e.g., glycogen storage disease and galactosemia, fructosemia), amino acid metabolism disorders (e.g., tyrosinemia), glycolipid and lipid metabolism disorders (e.g., Niemann-Pick disease, Hunter's disease, Hurler's disease, and Wolman's disease), glycoprotein metabolism disorders (e.g., Gaucher's disease), metal storage disorders (e.g., Hemochromatosis and Wilson's Disease), peroxisomal disorders (e.g., Zellweger syndrome and mitochondrial cytopathies); hereditary disorders of bilirubin metabolism (e.g., Crigler-Najjar syndrome, Gilbert syndrome, and Dubin-Johnson syndrome), hereditary disorders of bile formation (e.g., progressive familial intrahepatic cholestasis), bile acid biosynthesis disorders, protein biosynthesis and targeting disorders ($\alpha_1$-Antitrypsin deficiency and cystic fibrosis), acute liver failure arising from a combination of genetic and environmental factors.

The treatment methods include administering to the subject identified as in need of such treatment) an effective amount of a cell composition described herein, or a composition described herein to produce such a cell composition. Identifying a subject in need of such treatment can be in the judgment of a subject or a health care professional and can be subjective (e.g. opinion) or objective (e.g. measurable by a test or diagnostic method). Determination of those subjects "at risk" can also be made by any objective or subjective determination by a diagnostic test or opinion of a subject or health care provider (e.g., genetic test, enzyme or protein marker, family history, and the like). The compositions described herein may be also used in the treatment of any other disorders in which a reduction in liver function may be implicated.

The number of cells needed to restore liver function, fully or partially, varies depending on the degree of liver damage and the size, age and weight of the host. For example, the cells are administered in an amount effective to restore liver functions. Determination of effective amounts is well within the capability of those skilled in the art. The effective dose can be determined by using a variety of different assays designed to detect restoration of liver function. The progress of the transplant of the recipient can be determined using assays that include blood tests known as liver function tests. Such liver function tests include assays for alkaline phosphatase, alanine transaminase, aspartate transaminase and bilirubin. In addition, recipients can be examined for the presence or disappearance of features normally associated with liver disease such as, for example, jaundice, anemia, leukopenia, thrombocytopenia, increased heart rate, and high levels of insulin. Further, imaging tests such as ultrasound, computer assisted tomography (CAT) and magnetic resonance (MR) may be used to assay for liver function.

The iHep cells can be administered by conventional techniques such as injection of cells into the recipient host liver, injection into a site of liver lesion or at a site from which such cells can migrate to the site of the lesion (e.g. administration to spleen, portal vein, liver pulp, etc., e.g., by injection), or surgical transplantation of cells into the recipient host liver. In some instances it can be necessary to administer the iHep cells more than once to restore liver function. In addition, growth factors, such as G-CSF, or hormones, and TGFβ1 can be administered to the recipient prior to and following transplantation for the purpose of priming the recipient's liver and blood to accept the transplanted cells and/or to generate an environment supportive of hepatic cell proliferation.

"Treating" or "treatment" refers to administration of a compound or agent to a subject who has a disorder with the purpose to cure, alleviate, relieve, remedy, delay the onset of, prevent, or ameliorate the disorder, the symptom of the disorder, the disease state secondary to the disorder, or the predisposition toward the disorder. The terms "prevent," "preventing," "prevention," "prophylactic treatment" and the like refer to reducing the probability of developing a disorder or condition in a subject, who does not have, but is at risk of or susceptible to developing a disorder or condition.

A "subject" refers to a human and a non-human animal. In one embodiment, the subject is a human. In another, the subject is an experimental, non-human animal or animal suitable as a disease model. The term "animal" includes all vertebrate animals including humans. It also includes an individual animal in all stages of development, including embryonic and fetal stages. In particular, the term "vertebrate animal" includes, but not limited to, humans, non-human primates (particularly higher primates), canines (e.g., dogs), felines (e.g., cats); equines (e.g., horses), bovines (e.g., cattle), porcine (e.g., pigs), rodent (e.g., mouse or rat), guinea pig, cat, rabbit, as well as in avians, such as birds, amphibians, reptiles, etc. The term "avian" refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary. Examples of a non-human animal include all non-human vertebrates, e.g., non-human mammals and non-mammals mentioned above.

Tissue-Engineering

The invention also provides a tissue-engineered organ, or portion, or specific section thereof, as well as a tissue engineered device having the iHep cells of this invention or progenies thereof. A tissue engineered liver can provide a new therapy in which differentiated iHep cells are transplanted within three-dimensional polymer scaffolds to supplement or replace the function of a failing liver. Tissue-engineered organs can be used with a biocompatible scaffold to support cell growth in a three-dimensional configuration, which can be biodegradable.

The construction of a three-dimensional polymer-cell scaffold made of polymer and hepatocyte-like cell can be carried out according to WO/2003/076564 and U.S. Pat. Nos. 5,624,840 and 5,759,830. A tissue engineered liver can be made of iHep cells fabricated onto a matrix or a scaffold made of natural or manmade material. For example, the cells can be used to seed a decellularized liver scaffold as described in U.S. Patent Application 20050249816. Manmade materials that can be used are often biodegradable polymers, such as the three-dimensional tissue culture system in which cells were laid over a polymer support system (See U.S. Pat. No. 5,863,531). Materials suitable for polymer scaffold fabrication include polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon™, nylon silicon, and shape memory materials, such as poly(styrene-block-butadiene), polynorbornene, hydrogels, metallic alloys, and oligo (s-caprolactone) diol as switching segment/oligo (p-dioxyanone) diol as physical crosslink. Other suitable polymers can be obtained by reference to The Polymer Handbook, 3rd edition (Wiley, N.Y., 1989). Such tissue engineered liver can be implanted into the patient to restore liver function.

This invention also provides use of the hepatocyte-like cells of the invention as part of a bioreactor, e.g. a liver assist device. Further, the iHep cells of this invention or their progenies can be used as biological components of detoxification devices such as liver perfusion or liver assist devices. Specifically, the cells of this invention can be used to construct extracorporeal liver assist device such as a bio-artificial liver for use by subjects having liver disorders that result in hepatic failure or insufficiency. The use of such bio-artificial livers involves the perfusion of the subject's blood through the bio-artificial liver. In the blood perfusion protocol, the subject's blood is withdrawn and passed into contact with the iHep cell cultures. During such passage, molecules dissolved in the patient's blood, such as bilirubin, are taken up and metabolized by the hepatocyte cultures. In addition, the hepatocyte-like cells provide factors normally supplied by liver tissue.

An exemplary liver assist device includes a rigid, plastic outer shell and hollow semi-permeable membrane fibers which are seeded with iHep cells of this invention or their progenies. The fibers can be coated with collagen, lectin, laminin, or fibronectin, for the attachment of cells. Body fluid from a subject can perfuse through the device for detoxification according to procedures known in the art and then returned to the subject.

Drug Testing and Screening

The iHep cells of this invention or their progenies can also be used as a tool for drug testing and development process. For example, one can use the cells to assess changes in gene expression patterns caused by drugs being considered for development. The changes in gene expression pattern from potential drugs can be compared with those caused by control drugs known to affect the liver. This allows one to screen compounds for their effects on the liver earlier in the development process without using animals, thereby saving time and money. In some embodiments, the iHep cells of this invention or their progenies are used in a high throughput drug screening, such as in the manner described in U.S. Pat. No. 7,282,366.

The iHep cells of this invention or their progenies can also be used to assess toxicity of various compounds or compositions of interest, e.g. chemical, pharmaceutical, cosmetic, biocidal or biological compounds, food additives or compositions, or biological agents. The use of differentiated cells may be preferred in such assays of toxicity, as the cells more closely resemble the cell types present in the liver of an organism. For example, a particular compound or composition is considered toxic or likely toxic, if it shows a detrimental effect on the viability of cells or on one or more aspect of cellular metabolism or function. The viability of cells in vitro may be measured using techniques known in the art, including colorimetric assays, such as the MTT (or MTT derivative) assays or LDH leakage assays, or using fluorescence-based assays, such as, e.g., the Live/Dead assay, CyQuant cell proliferation assay, or assays of apoptosis. Other useful assays include those that measure particular aspects of cellular metabolism or function.

Carcinogenicity Evaluation

It is known in the art that various compounds cause tumors in experimental animals such as mice even though they fail to act as mutagens in test organisms such as bacteria or fungi. One of the reasons for this phenomenon is metabolic activation; i.e., some chemicals are metabolically altered by enzymes in the liver (the P450 oxidase system and hydroxylation systems) or other tissues, creating new compounds that are both mutagenic and carcinogenic. In order to identify such carcinogens, people have used screening assays involving incubating a test chemical compound with liver extracts or liver tissues prior to exposure of the test organism to the metabolic product (Ames et al., 1975, Mut. Res. 31:347-364; U.S. Pat. No. 7,026,137). The iHep cells of this invention or their progenies can be used as a substitute for the liver extracts or liver tissues described in the conventional assays.

Thus, the present invention also provides methods and assays to evaluate the carcinogenicity of a test compound or agent use the cells of this invention, which closely resemble the cell types present in the liver of an organism. These cells can be used in assays of both genotoxic and non-genotoxic (i.e., epigenetic) carcinogenicity. For example, one can contact the cells with a test agent and then examine neoplastic transformation or genetic stability of the cells. The agent is considered carcinogenic or likely carcinogenic, if it induces neoplastic transformation of the cells, or induces phenotypic changes in the cells that may be predictive of such neoplastic transformation, or induces genetic or metabolic changes that may potentially cause such neoplastic transformation.

Examples of phenotypic changes in the cells include, but are not limited to, morphological transformation, increased proliferation, dedifferentiation, independence of attachment, removal of contact inhibition of cells grown in monolayers, or expression of specific marker proteins. Such genetic changes in the cells may, but are not limited to, comprise DNA damage, chromosomal aberrations, e.g., chromosomal rearrangements, alterations in chromosome number (aneuploidy), or karyotype aberrations, gene mutations, e.g., point mutations, deletions or insertions. Agents that cause this kind of genetic changes are often referred to as mutagenic or mutagens. Accordingly, the cells provided by the present invention will be very useful in assays of mutagens, i.e., in assays of mutagenicity.

For the purposes of mutagenicity testing, the cells of the present invention can be genetically altered. For example, the cells may contain a transgene, encoding a polypeptide that increases the cells sensitivity to a particular proliferation-inhibiting agent. Consequently, genetic alterations in some cells removing the expression of such transgene would release these cells from this inhibition. Mutagenicity may then be assessed by methods of scoring such cells.

Other Uses

The cells of this invention can further used for various other uses. For example, they can be used in producing one or more proteins expressed in the liver.

One example is blood coagulation factors, which are useful for subjects with hemophilia and other blood clotting disorders. Currently, most of the preparations of blood coagulation factors are from donated blood and that presents the disadvantage that the danger of transmitting hepatitis. Producing blood coagulation factors in vitro from the hepatocyte-like cell described herein greatly reduces the risk of transmitting hepatitis or other blood borne diseases. To produce coagulation factors, one can cultured the cells of this invention under suitable conditions. After the cultured hepatocyte-like cells have reached confluency, the supernatant culture media can be collected and purified according to methods known in the art, such as those described in U.S. Pat. No. 4,789,733 and Kane et al. J. Biol. Chem., 256:1002-1007, 1981.

Primary hepatocytes have versatile characteristics and functions. To use iHep cells for fully recapitulating primary hepatocytes, one can improve iHep cells in vitro for specialized purposes. For example, iHep cells as disclosed herein express several Cyp genes and acquire Cyp1a, Cyp3a and Cyp2c activities. By further optimization of iHep cells to express drug transporter genes and enhanced Cyp activities, one can obtain an alternative to primary hepatocytes for the early stages of drug discovery. Interestingly, preliminary data by the inventors implicate that mouse ESC-derived hepatocyte-like cells appeared to be more immature compared with iHep cells as disclosed herein. Nonetheless, a compre-hensive comparison of iHep cells with other surrogate hepatocyte-like cells would be necessary, so that when a specialized hepatic function is desired one can decide which hepatocyte-like cells to choose.

Compositions

In a further aspect, the invention relates to a pharmaceutical composition comprising the human iHep cells, or iHep cells from other species including man, obtainable or directly obtained using the herein described methods, or a cell population comprising such as defined above, or the progeny thereof.

The term "pharmaceutical composition" refers to the combination of an active agent (e.g., cells or transcription factors disclosed herein) with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it (e.g., keeping iHep cells alive). One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

EXAMPLES

Materials and Methods

The following materials and methods apply to all examples, unless specifically noted otherwise.

Mice p19$^{Arf1-/-}$ mice, Fah$^{-/-}$Rag2$^{-/-}$ mice and NOD/SCID mice were maintained in specific pathogen-free husbandry. Fah$^{-/-}$Rag2$^{-/-}$ mice were fed with drinking water containing 7.5 mgl$^{-1}$ NTBC. The genetic background for p19$^{Arf-/-}$ and Fah$^{-/-}$Rag2$^{-/-}$ mice was C57B16/J 3 129Sv. Fah$^{-/-}$Rag2$^{-/-}$ mice were used as the recipient to reduce immunological rejection of iHep cells after transplantation.

Molecular Cloning and Lentivirus Production

A multi-cloning site (CGGGATCCCGGCGCGCCGAC-TAGTCGACGCGTCGAGGT AACCTACGGACCGGTTT; SEQ ID NO: 15) was inserted into the PmeI restriction site of lentiviral vector pWPI (ADDGENE). cDNAs of candidate genes were cloned into the modified pWPI plasmid. For p19$^{Arf}$ shRNA expression, DNA oligonucleotides encoding p19$^{Arf}$ shRNA (CCGGGTGAACATGTTGTTGAGGCTAG-GATCCTAGCCTCAACAACAT-GTTCACTITTTG; SEQ ID NO: 16) were inserted into the AgeI and EcoRI restriction sites of the pLKO.1 plasmid. Constructed pWPI or pLKO.1 plasmids were then introduced to 293FT cells together with packaging plasmid psPAX2 (ADDGENE) and envelope plasmid pMD2.G (ADDGENE). After 48 h incubation, the medium containing lentiviruses was collected and passed through a 0.45 mm filter.

Fibroblast Culture and Bile Duct Induction

To isolate tail-tip fibroblasts, tails (each 5 cm in length) were cut from two-month-old mice. The dermis was peeled and the tails minced into 1-cm pieces. Two pieces were placed per 60-mm collagen-1-coated dish in 5 ml DMEM (SIGMA-ALDRICH) containing 10% FBS (SIGMA-ALDRICH). After 5 days incubation, fibroblasts that migrated out of the tails were transferred to new collagen-1-coated dishes. TTFs between passage 7 and 9 were used for iHep cell induction. Embryonic fibroblasts were isolated from E13.5 embryos. Head and visceral tissue were dissected and removed. The remaining tissues were minced and incubated with 0.25% trypsin (GIBCO) at 37° C. for 15 min. Isolated cells were plated onto a 60-mm collagen-1-coated dish in 5 ml DMEM containing 10% FBS. MEFs at passage 3 for were used lentiviral infection.

For bile duct differentiation, $1 \times 10^4$ cells were re-suspended in 1 ml DMEM/F12 medium with 1 ml freshly prepared collagen gel solution and poured into a 35-mm dish. After gel solidification, cells were cultured with 1.5 ml DMEM/F12 supplemented with 10% FBS, 1×ITS, 20 ng ml$^{-1}$ HGF for 3 days.

Primary Hepatocyte Isolation and Culture

Adult mice were subjected to standard two-step collagenase perfusion for isolation of primary hepatocytes. Briefly, the liver was pre-perfused through the portal vein with calcium-free buffer (0.5 mM EGTA, 1×EBSS without Ca$^{2+}$ and Mg$^{2+}$) and then perfused with collagenase (0.2 mgml$^{-1}$ collagenase type IV (SIGMA), 10 mM HEPES, 1×EBSS with Ca$^{2+}$ and Mg$^{2+}$). Parenchymal cells were purified by Percoll buffer (90% Percoll (SIGMA), 1×EBSS) at low-speed centrifugation (1,500 r.p.m., 10 min). Viability of isolated hepatocytes was around 90% as determined by Trypan blue. For microarray analysis, p19$^{Arf-/-}$ primary hepatocytes were cultured in modified Block's medium supplemented with 0.1 mM dexamethasone, 20 μg l$^{-1}$ TGF-α, 10 μg l$^{-1}$ EGF, 4.2 mgl$^{-1}$ insulin, 3.8 mgl$^{-1}$ human transferrin and 5 μg l$^{-1}$ sodiumselenite in collagen-I-coated dishes for 6 days before harvesting for RNA extraction. For other experiments, p19$^{Arf-/-}$ primary hepatocytes were immediately lysed in TRIZOL for total RNA isolation.

PCR

For most experiments, total RNA was isolated from cells by TRIZOL (INVITROGEN). For RNA extraction from formalin-fixed-paraffin-embedded (FFPE) tissues, four serial sections mounted on polyethylene terephthalate (PET) membrane frame slides were deparaffinized and air dried. The first section was stained with anti-Fah antibody to identify the repopulated Fah$^+$ nodules. On the basis of the result of Fah immunostaining in the first section, Fah$^+$ tissues within the nodules were microdissected from the following three sections by a Leica LMD7000 Laser Microdissection Microscope (LEICA MICROSYSTEMS) with laser intensity of 45 and speed of 5. After microdissection, the remaining sections on the slides were further stained with anti-Fah antibody to confirm that only tissues inside Fah$^+$ nodules were separated. Microdissected tissues from the same Fah$^+$ nodule were pooled together for total RNA extraction using RNeasy FFPE Kit (QIAGEN).

A total of 1 μg RNA was reverse transcribed into cDNA with M-MLV Reverse Transcriptase (PROMEGA) according to the manufacturer's instructions. For DNA extraction from formalin-fixed-paraffin-embedded tissues, the QIAamp DNA FFPE Tissue Kit (QIAGEN) was applied according to the manufacturer's instructions. PCR was performed with HiFi Taq polymerase (TRANSGEN). Quantitative real-time PCR was performed with SYBR Premix Ex Taq (TaKaRa) on an ABI 7500 fast real-time PCR system (APPLIED BIOSYSTEMS).

Immunofluorescence

For immunofluorescence staining, the cells were fixed with 4% paraformaldehyde for 15 min at room temperature, and then incubated with PBS containing 0.2% Triton X-100 (SIGMA) for 15 min. Cells were then washed three times with PBS. After being blocked by 3% BSA in PBS for 60 min at room temperature, cells were incubated with primary antibodies at 4° C. overnight, washed three times with PBS, and then incubated with appropriate fluorescence-conjugated secondary antibody for 60 min at room temperature in the dark. Nuclei were stained with DAPI (SIGMA). Primary and secondary antibodies were diluted in PBS containing 3% BSA. Antibodies used for immunofluorescence are as follows: mouse anti-Tjp1 (INVITROGEN, 1:750), rabbit anti-E-cadherin (CELL SIGNALING, 1:500), mouse anti-albumin (R&D, 1:200), goat anti-Hnf4α(SANTA CRUZ, 1:200), Cy5-conjugated goat anti-mouse IgG (1:1,000), Cy3-conjugated goat anti-rabbit IgG (1:1,000), Cy3-conjugated donkey anti-goat IgG (JACKSON LAB-ORATORIES JACKSON LAB, 1:1,000). For Y-chromosome fluorescent in situ hybridization (FISH), liver samples of male Fah$^{-/-}$ Rag2$^{-/-}$ mice transplanted with female iHep cells were embedded in paraffin and hybridized with mouse Y-chromosome probe (ID LABS INC., Canada) according to manufacturer's instruction.

FACS Analyses

For intracellular staining of albumin, $10^6$ cells were harvested and fixed with 4% PFA for 30 min, and then permeabilized in staining buffer (PBS with 10% FBS and 0.5% saponin) for 10 min. Cells were then incubated with primary antibody (anti-albumin, R&D) for 30 min in staining buffer, followed with secondary antibody (Cy$_5$-conjugated goat anti-mouse IgG, Jackson Laboratories) incubation for 30 min. Cells were analyzed by the Calibur flow cytometer (BECTON DICKINSON). Data were analyzed with Windows Multiple Document Interface for Flow Cytometry (WinMDI, version 2.9).

PAS Stain, Dii-Ac-LDL and ICG Uptake Assays, Alb ELISA and CYP Metabolism Assay

Cells were stained by periodic acid-Schiff (PAS, SIGMA) and DiI-ac-LDL (INVITROGEN) following the manufacturer's instructions. For the indocyanine green (ICG, SIGMA) uptake assay, cells were cultured in the medium supplemented with progesterone, pregnenolone-16α-carbonitrile and 8-bromo cAMP for 2 days. Cells had their medium changed with 1 mg ml$^{-1}$ ICG and were incubated at 37° C. for 1 h, followed by washing with PBS three times.

To determine Alb secretion, TTFs transduced with three factors were cultured in the medium without phenol red. Culture supernatant was collected 24 h after medium change. The amount of Alb in the supernatant was determined by the mouse albumin ELISA kit (BETHYL LABORATORY) according to the manufacturer's instructions. For the measurement of CYP enzyme activities, TTFs and iHep cells were cultured in the medium with 50 μM 3-methylcholanthrene for 48 h. Cells were dissociated and incubated with substrate in 200 ml incubation medium at different concentrations for 3 h at 37° C. To stop the reaction, 800 μl cold methanol was added and centrifuged. The supernatants were collected for measurement of indicated productions by LC-MS/MS (AGILENT 1200 HPLC and ABI 4000 mass-spectrometer). Freshly isolated hepatocytes were used as a positive control. Total cell protein amount was used to normalize the data. Substrates and metabolic products for standard were purchased: phenacetin, diclofenac, bufuralol, acetaminophen, 4'-OH diclofenac (SIGMA), testosterone (FLUKA), 6β-OH-testosterone (CERILLIANT) and 1'-OH-bufuralol (TORONTO RESEARCH CHEMICALS).

Microarray Analysis

Total RNA extracted from p19$^{Arf-/-}$ TTFs, p19$^{Arf-/-}$ MEFs, p19$^{Arf-/-}$ hepatocytes cultured for 6 days, 3TF-transduced p19$^{Arf-/-}$ TTFs without enrichment of epithelial cells, and iHep cells from different experiments was hybridized to whole mouse gene expression microarray (AGILENT) under the manufacturer's instruction. Data were normalized by Gene-Spring (AGILENT). Microarray hybridization and analysis were carried out by ShanghaiBio Cooperation. Out of 29,153 annotated genes, 11,797 genes for which expression levels were at least twofold different between p19$^{Arf-/-}$ TTFs and primary p19$^{Arf-/-}$ hepatocytes were selected for analyses. Hierarchical clustering of samples was performed by Cluster 3.0 software. Average linkage with the uncentred correlation similarity metric was used for the clustering of samples. Original data were uploaded to the Gene Expression Omnibus database (accession number GSE23635).

In Vivo Function Analysis

Fah$^{-/-}$Rag2$^{-/-}$ mice were maintained with 7.5 mgl$^{-1}$ NTBC in the drinking water. 8.33×10$^5$ iHep cells and 8.33× 10$^{5-}$ p19$^{Arf-/-}$ TTFs were transplanted into the spleens of Fah$^{-/-}$Rag2$^{-/-}$ mice at the age of 8-12 weeks, respectively. NTBC was withdrawn from the drinking water after cell transplantation. Ten Fah$^{-/-}$Rag2$^{-/-}$ mice without any transplantation also had NTBC withdrawn as a control. A survival curve was generated by SPSS for windows using Kaplan-Meier method. Eight weeks after transplantation, the blood of surviving iHep-cell-transplanted Fah$^{-/-}$Rag2$^{-/-}$ mice was collected from the retro-orbital sinus and centrifuged at 12,000 r.p.m. for 15 min. The serum was frozen at 280° C. until biochemical analyses. Total bilirubin, albumin, ALT, AST, blood urea nitrogen and creatinine were measured by 7600-020 clinical analyser (HITACHI). Amino acids were quantified by liquid chromatography-mass spectrometry ABI 3200 Q TRAP LC-MS/MS system (APPLIED BIOSYSTEM). After blood collection, mice were killed by cervical dislocation and livers were harvested, fixed and stained with Fah polyclonal antibody or haematoxylin and eosin as previously described. Blood and liver samples of control NTBC-off Fah$^{-/-}$Rag2$^{-/-}$ mice were collected after losing 20% body weight.

Tumour Generation Assay

The human hepatoma cell line PLC/PRF/5 was cultured in the same medium as iHep cells. iHep cells were induced and enriched as described above. After 21 days induction, cells were detached by trypsin and suspended in PBS. Seven NOD/SCID mice respectively were injected with 5×10$^6$ iHep cells in the left subcutaneous flank and 5×10$^6$ PLC/PRF/5 cells in the right subcutaneous flank. Tumour numbers were counted 8 weeks after injection Statistics All data are presented as mean±s.d. For most statistical evaluation, an unpaired Student's t-test was applied for calculating statistical probability in this study. For survival analysis, the Mantel-Cox log-rank test was applied. Statistical calculation was performed using STATISTICAL PROGRAM FOR SOCIAL SCIENCES SOFTWARE (SPSS, IBM). For all statistics, data from at least three independent samples or repeated experiments were used.

Example 1

In this example, a group of transcription factors sufficient for inducing hepatocytes from fibroblasts were identified.

Fourteen mouse transcription factors ("14TF," Table 1) important for liver development and function (Kyrmizi et al. Genes Dev. 20, 2293-2305 (2006), Zaret, Nature Rev. Genet. 9, 329-340 (2008), Schrem et al., J. Pharmacol. Rev. 54, 129-158 (2002), and Schrem et al. Pharmacol. Rev. 56, 291-330 (2004)) were transduced into immortalized 3T3 fibroblasts, mouse embryonic fibroblasts (MEFs) and tail-tip fibroblasts (TTFs) via lentiviral infection. The hepatic genes albumin (Alb) and Tdo2 were induced in these cells at day 5 after infection (FIG. 5a), indicating that fibroblasts have the potential to be converted to hepatocytes.

To ensure that the process is independent of spontaneous immortalization and embryonic progenitors, TTFs were used to further study the 14 TFs. Wild-type TTFs showed proliferation arrest and cell death within 7 days after transduction (FIG. 1b), thereby inhibiting continuous hepatic conversion.

Because p19$^{Arf}$ (also called Cdkn2a)-null (p19$^{Arf-/-}$) hepatocytes proliferate in vitro without losing genetic stability (Mikula et al. Hepatology 39, 628-634 (2004), p19$^{Arf-/-}$ TTFs were used to overcome the proliferative limitation according to the design shown in FIG. 1a. Briefly, primary p19$^{Arf-/-}$ TTFs were infected with lentiviruses expressing hepatic transcription factors. The cells were changed to modified Block's medium 2 days after infection and further cultured for 14-21 days.

Remarkably, proliferative cells with epithelial morphology were induced from mesenchymal p$^{Arf-/-}$ TTFs after transduction of 14TF (FIG. 5b). Moreover, these cells expressed Alb, Tdo2 and Ttr (FIG. 5c). Eleven epithelial colonies, picked up at day 21 after lentiviral transduction, expressed hepatic genes and the exogenous 14TF at different levels (FIG. 6).

One epithelial colony, ET26, was further characterized (FIG. 1b). RT-PCR assays were carried out to examine expression of various genes in ET26, while primary hepatocytes and TTFs were used as controls.

The results show that ET26 cells expressed hepatic secretary protein genes, cytokeratin genes, epithelial cell adhesion genes and endogenous hepatic transcription factors (FIG. 1c). By contrast, expression of Col1a1, Pdgfrb, Postn and Fsp1 (also called S100a4), genes typical for fibroblast, was down-regulated in ET26 cells (FIG. 1c).

Functionally, cytoplasmic accumulation of glycogen or low density lipoprotein was determined by periodic acid-Schiff (PAS) staining or DiI-ac-LDL intake. It was found that ET26 cells showed glycogen storage as demonstrated in FIG. 1d and uptake of DiI-labelled acetylated low density lipoprotein (DiI-ac-LDL, FIG. 1 e).

These above results indicated that $p19^{Arf-/-}$ TTFs were converted into cells with significant hepatic gene expression and hepatic functions.

Example 2

In this example, a number of key factors required for hepatic conversion were identified. More specifically, the following combinations were examined: (i) a combination of six factors ("6TF"), including Foxa2, Foxa3, Hnf1α, Hnf4α, Hnf6 and Gata4, and (ii) a combination eight factors ("8TF"), including the just-mentioned 6TF plus Foxa1 and Hlf in the same manner described above.

It was found that either 6TF or 8TF converted TTFs to epithelial colonies with hepatic gene expression at comparable levels (FIGS. 7a and b). Upon withdrawal of Hnf6 from 6TF, it was found that there was significantly increased hepatic gene expression and epithelial colony formation (FIGS. 7a and b). For the remaining five factors ("5TF"), removal of Hnf4α further promoted the formation of epithelial colonies (FIG. 7c).

The remaining four factors were further grouped into two combinations: (1) Gata4, Hnf1α and Foxa3 ("3TF") and (2) Gata4, Hnf1α and Foxa2 ("3TF'"). It was found that 3TF showed a stronger effect than 3TF' on the induction of hepatic gene expression and epithelial colony formation (FIG. 7d). Remarkably, 3TF induced endogenous Foxa2 and Foxa3 expression (FIG. 7d), and removal of Foxa3 and Hnf1α from 3TF failed to form epithelial colonies. On the other hand, combination of Foxa3 and Hnf1α (i.e., removal of Gata4 from 3TF) were still able to induce formation of epithelial colonies, albeit at a lower degree (FIG. 1f), suggesting that GATA 4 is not absolutely required, but notably enhances the efficiency of hepatic conversion.

Intriguingly, it was found that 3TF triggered $p19^{Arf-/-}$ MEFs to express hepatic genes (FIG. 8), indicating the potential to induce hepatic conversion of embryonic fibroblasts. Furthermore, upon RNA-interference-mediated knockdown of $p19^{Arf-/-}$, it was found that 3TF also converted wild-type TTFs to epithelial cells with hepatic gene expression (FIG. 9).

Example 3

In this example, assays were carried out to examine iHep cells induced by over-expression of Gata4, Hnf1α and Foxa3 and the inactivation of $p19^{Arf}$ for their hepatic features.

It was found that, at day 6, the epithelial cells induced by 3TF were positively stained for tight junction protein 1 (Tjp1) and E-cadherin (FIGS. 2a-c). At day 14, 23% of epithelial cells were positive for Alb (FIG. 10a), indicating an efficient hepatic conversion. The increased expression of hepatic genes over time, for example, Alb, Ttr, transferring (Trf) and CK18 (also called Krt18), showed a progressively enhanced reprogramming (FIG. 2d and FIG. 10b, P<0.05).

Interestingly, it was found that iHep cells also expressed Afp and CK19 (also called Krt19) (FIG. 2d). Protein expression of Alb and Hnf4α was confirmed by immunofluorescent staining in iHep cells (FIGS. 10c and d. Notably, expression levels of exogenous 3TF were markedly decreased during hepatic conversion, indicating that continuous expression of exogenous 3TF is not required (FIG. 10e).

Furthermore, individual iHep colonies showed similar expression patterns of hepatic genes and fibrotic genes (FIG. 10f), indicating a homogeneous conversion among individual TTFs. Although iHep cells expressed Afp and CK19 (FIG. 2d), other hepatoblast marker genes, such as Lin28b, Igf2 and Dlk1 (Li. et al., Gastroenterology 139, 2158-2169 (2010)), were undetectable during hepatic conversion (FIG. 11a).

Importantly, cytochrome P450 (CYP) enzymes specific to mature hepatocytes were detectable in iHep cells (FIG. 11b), suggesting that hepatic conversion undertakes a process without reversion to progenitors. Moreover, iHep cells neither expressed bile duct marker genes nor formed branching bile duct tubes in vitro (FIGS. 11 c and d). The marker genes for pancreatic exocrine and endocrine cells and intestinal cells were also undetectable (FIGS. 11e and f). Therefore, the above results indicate that TTFs are not converted to lineages other than hepatocytes.

Microarray assays were carried out to compare the global expression profiles among iHep cells, TTFs, MEFs and hepatocytes cultured for 6 days. Pearson correlation analysis showed that iHep cells were clustered with cultured hepatocytes but separated from TTFs and MEFs (FIG. 2e).

Specifically, microarray data revealed that numerous hepatic functional genes were up-regulated in iHep cells compared to TTFs (FIG. 12 and Tables 2 and 3). When compared with cultured hepatocytes, 877 out of 29,153 annotated genes were found to be up-regulated in iHep cells, including Afp, CK19, Fabp4 and S100a9, whereas 817 genes were down-regulated, such as Cyp4b1, Cyp2c40 and Apob (fold change>2, P<0.01, t-test).

Shown in Table 3 are the results of genome-wide gene expression profile analysis of iHep cells. Global gene expression profiles of $p19Arf^{-/-}$ TTFs, cultured $p19Arf^{-/-}$ hepatocytes, and iHep cells were analyzed using Agilent whole genome oligo chips. Average expression levels of each listed gene in iHep cells were divided by the expression level of that gene in TTFs to calculate the ratio of iHep/TTF. The ratio of hepatocyte/TTF was calculated via dividing the expression level in cultured hepatocytes by the expression level in TTFs. Shown in Table 3 are microarray data of all CYP genes.

Notably, iHep cells established substantial hepatic functions. iHep cells accu-mulated PAS-positive glycogen aggregations and transported Dilac-LDL into the cytoplasm (FIGS. 2f, g). Indocyanine green uptake was found in 20% of iHep cells (FIG. 2h). Furthermore, iHep cells secreted high amounts of Alb into medium (FIG. 2i, P<0.05).

Figure 13:
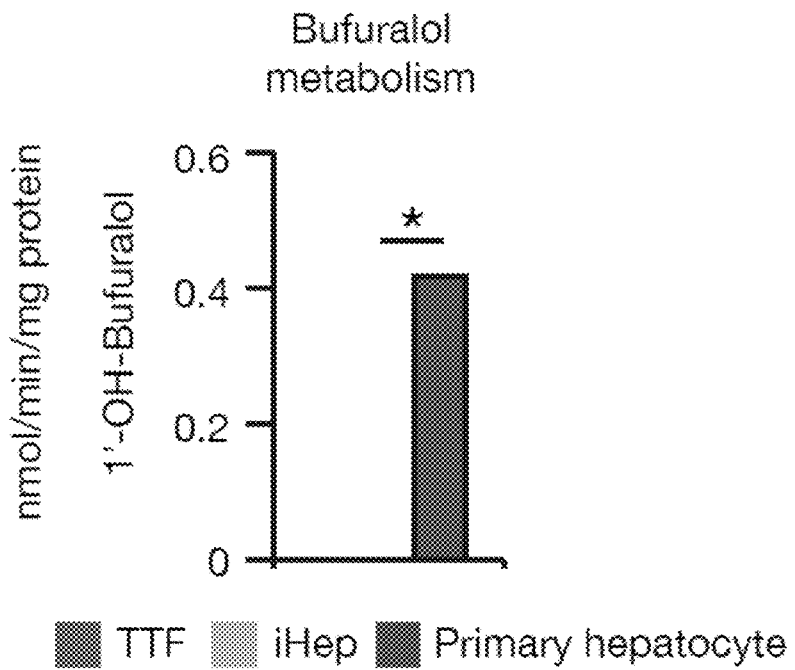
FIG. 13 is a diagram showing Cyp2d22 activities of iHep cells as measured by the production of Bufuralol metabolite, 1'-OH-Bufuralol ($P<0.05$, t-test).

Importantly, iHep cells metabolized phenacetin, testosterone and diclofenac (FIGS. 2j-l and Table 4, P<0.05), whereas metabolic activity for bufuralol was undetected (FIG. 13). More specifically, iHep cells were treated with Phenacetin, Testosterone, or Diclofenac at different concentrations. Metabolites of these chemicals were measured by liquid chromatography-tandem mass spectrometry (LC/MS/MS) according to each standard curve. The results are shown in Table 4.

TABLE 2

| Gene | iHep/TTF | hepatocyte/TTF |
|---|---|---|
| a | | |
| Glucose metabolism | | |
| Acn9 | 4.04 | 2.83 |
| Aldob | 5118.36 | 287.55 |
| Aldoc | 7.33 | 0.78 |
| Gckr | 3.06 | 14.96 |
| Pgd | 1.76 | 1.11 |
| Pgm1 | 2.79 | 1.06 |
| Pklr | 4.82 | 12.46 |
| Ppargc1a | 21.17 | 6.83 |
| Slc25a10 | 2.59 | 1.43 |
| Tktl1 | 1.01 | 1.39 |
| Ugdh | 2.21 | 1.15 |
| b | | |
| Fatty acid, cholesterol, bile acid metabolsim | | |
| Abca2 | 1.54 | 0.90 |
| Abca3 | 12.21 | 3.35 |
| Acox1 | 1.82 | 1.40 |
| Acox2 | 242.61 | 150.38 |
| Acsl1 | 6.40 | 2.06 |
| Acsl3 | 1.51 | 0.37 |
| Acsl4 | 3.76 | 1.76 |
| Acsl5 | 5.33 | 2.59 |
| Acsm1 | 93.77 | 2.04 |
| Acsm2 | 275.45 | 1.81 |
| Acsm3 | 677.82 | 5.08 |
| Acss2 | 3.74 | 1.13 |
| Angptl3 | 1.16 | 6.41 |
| Cd36 | 168.60 | 383.62 |
| Dhcr24 | 3.01 | 0.79 |
| Fabp1 | 4302.63 | 314.27 |
| Fasn | 1.57 | 0.44 |
| Fdft1 | 1.46 | 0.68 |
| Got2 | 1.33 | 1.89 |
| Hmgcr1 | 2.41 | 0.58 |
| Hmgcr2 | 36.34 | 1.78 |
| Ldlr | 1.39 | 0.31 |
| Lss | 2.71 | 0.49 |
| Pmvk | 3.16 | 0.54 |
| Scd3 | 11.37 | 3.08 |
| Ucp2 | 191.69 | 16.65 |
| c | | |
| Secretory protein | | |
| Agt | 494.73 | 42.63 |
| Alb1 | 538.94 | 4389.19 |
| Apoa1 | 724.62 | 257.99 |
| Apob | 117.05 | 1558.67 |
| Apoc1 | 9.57 | 416.70 |
| Apoc2 | 1265.96 | 994.75 |
| Apoc3 | 4.95 | 107.83 |
| Apoe | 90.27 | 64.01 |
| Cp | 1598.44 | 1030.52 |
| Gc | 1261.39 | 1645.27 |
| Hp | 976.86 | 269.88 |
| Hpx | 341.86 | 444.74 |
| Igfbp1 | 12.80 | 17389.89 |
| Rbp4 | 318.98 | 236.13 |
| Serpina7 | 156.59 | 99.23 |
| Ttr | 289.89 | 75.02 |
| d | | |
| Coagulation | | |
| C3 | 246.27 | 80.40 |
| C4bp | 943.97 | 159.00 |
| C9 | 126.39 | 15.85 |
| F11r | 39.19 | 30.41 |
| F2 | 58.10 | 531.86 |
| F2rl1 | 7.60 | 7.35 |
| F5 | 2.09 | 1.87 |
| F8a | 2.24 | 1.28 |
| Fga | 795.41 | 427.24 |
| Fgb | 7561.63 | 5033.01 |
| Plg | 19.49 | 5.36 |
| Proc | 1.58 | 69.33 |
| Proz | 2.04 | 10.96 |
| Serpinf2 | 205.77 | 32.30 |
| e | | |
| Drug metabolism | | |
| Aldh16a1 | 3.84 | 0.54 |
| Aldh3a2 | 8.39 | 1.42 |
| Aldh3b2 | 1.50 | 1.94 |
| Aldh4a1 | 1.84 | 0.95 |
| Fmo2 | 16.43 | 52.87 |
| Gnpnat1 | 1.07 | 0.82 |
| Gpx6 | 3.38 | 1.36 |
| Gsta1 | 41.24 | 62.72 |
| Gsta2 | 37.63 | 59.93 |
| Gsta3 | 387.34 | 332.10 |
| Gsta3 | 6.32 | 0.74 |
| Gstm1 | 8.83 | 1.86 |
| Gstm3 | 7.00 | 1.34 |
| Gstm6 | 8.54 | 19.01 |
| Gstm7 | 3.29 | 1.69 |
| Gstp1 | 2.62 | 2.20 |
| Maob | 55.43 | 7.59 |
| Sult1a1 | 78.74 | 64.64 |
| Sult1b1 | 10.11 | 97.50 |
| Sult1c2 | 32.28 | 17.90 |
| Ugt1a9 | 16.40 | 1.99 |
| Ugt2a1 | 2.50 | 2.97 |
| Ugt2b34 | 3.71 | 15.10 |
| Ugt2b35 | 103.67 | 567.58 |
| Ugt2b36 | 20.61 | 286.48 |
| Ugt2b37 | 1.52 | 17.77 |
| Ugt2b38 | 7.28 | 74.30 |
| Ugt2b5 | 1.84 | 39.78 |
| Ugt3a1 | 1.87 | 1.35 |
| Ugt8a | 4.68 | 1.65 |

TABLE 3

| Gene | iHep/TTF | hepatocyte/TTF |
|---|---|---|
| Cyp11a1 | 2.68 | 1.06 |
| Cyp11b2 | 0.70 | 0.41 |
| Cyp17a1 | 0.99 | 1.63 |
| Cyp19a1 | 0.73 | 1.87 |
| Cyp1a1 | 4.31 | 273.02 |
| Cyp1a2 | 1.03 | 2.60 |
| Cyp1b1 | 9.96 | 32.44 |
| Cyp20a1 | 0.43 | 0.34 |
| Cyp21a1 | 1.54 | 1.89 |
| Cyp24a1 | 1.52 | 1.19 |
| Cyp26a1 | 1.03 | 27.05 |
| Cyp26b1 | 0.08 | 0.31 |
| Cyp27a1 | 20.06 | 6.40 |
| Cyp27b1 | 1.21 | 2.38 |
| Cyp2a12 | 0.90 | 6.99 |
| Cyp2a22 | 0.57 | 1.93 |
| Cyp2a4 | 29.35 | 165.64 |
| Cyp2a5 | 25.53 | 130.53 |
| Cyp2ab1 | 0.96 | 0.42 |
| Cyp2b10 | 100.23 | 7.02 |
| Cyp2b13 | 119.88 | 8.13 |
| Cyp2b19 | 1.38 | 1.20 |
| Cyp2b23 | 1.33 | 1.39 |
| Cyp2b9 | 276.33 | 16.58 |
| Cyp2c29 | 7.89 | 10.75 |
| Cyp2c37 | 1.78 | 1.37 |
| Cyp2c38 | 0.83 | 0.80 |
| Cyp2c39 | 1.16 | 7.30 |
| Cyp2c40 | 29.29 | 58.72 |
| Cyp2c44 | 1.79 | 0.36 |
| Cyp2c54 | 1.06 | 1.81 |
| Cyp2c55 | 0.38 | 0.22 |
| Cyp2c65 | 806.12 | 8.75 |
| Cyp2c66 | 121.84 | 2.92 |
| Cyp2c70 | 5.75 | 15.83 |

TABLE 3-continued

| Gene | iHep/TTF | hepatocyte/TTF |
|---|---|---|
| Cyp2d10 | 57.71 | 12.25 |
| Cyp2d12 | 14.99 | 2.32 |
| Cyp2d13 | 1.09 | 1.51 |
| Cyp2d22 | 6.16 | 1.67 |
| Cyp2d26 | 181.62 | 20.60 |
| Cyp2d34 | 69.87 | 10.66 |
| Cyp2d9 | 17.48 | 3.95 |
| Cyp2e1 | 1.33 | 8.43 |
| Cyp2f2 | 0.08 | 0.19 |
| Cyp2g1 | 1.55 | 1.90 |
| Cyp2j11 | 1.19 | 0.59 |
| Cyp2j13 | 0.98 | 3.73 |
| Cyp2j5 | 0.67 | 7.31 |
| Cyp2j6 | 0.27 | 1.79 |
| Cyp2j9 | 0.07 | 0.32 |
| Cyp2r1 | 0.92 | 2.51 |
| Cyp2s1 | 1132.90 | 14.11 |
| Cyp2u1 | 0.41 | 1.78 |
| Cyp2w1 | 1.41 | 1.06 |
| Cyp39a1 | 11.91 | 1.42 |
| Cyp3a11 | 1.25 | 0.78 |
| Cyp3a13 | 203.22 | 1109.02 |
| Cyp3a16 | 5.66 | 3.15 |
| Cyp3a25 | 3.47 | 4.04 |
| Cyp3a41a | 3.60 | 4.07 |
| Cyp3a44 | 3.66 | 5.41 |
| Cyp46a1 | 1.37 | 1.39 |
| Cyp4a10 | 1.93 | 2.23 |
| Cyp4a12a | 1.36 | 3.49 |
| Cyp4a12b | 3.38 | 3.84 |
| Cyp4a14 | 1.24 | 2.41 |
| Cyp4a29 | 0.82 | 0.39 |
| Cyp4a31 | 1.04 | 1.08 |
| Cyp4b1 | 20.94 | 1166.04 |
| Cyp4f13 | 1.12 | 1.76 |
| Cyp4f14 | 1.18 | 5.09 |
| Cyp4f15 | 0.97 | 1.78 |
| Cyp4f16 | 0.40 | 1.12 |
| Cyp4f18 | 0.88 | 1.99 |
| Cyp4f39 | 2.44 | 1.37 |
| Cyp4v3 | 0.05 | 2.37 |
| Cyp51 | 1.15 | 0.34 |
| Cyp7a1 | 1.36 | 1.90 |
| Cyp7b1 | 0.02 | 0.81 |
| Cyp8b1 | 0.92 | 1.85 |

TABLE 4 a

| | acetaminophen (pmol/min/mg protein) | | |
|---|---|---|---|
| Phenacetin (μM) | TTF | iHep | Primary hepatocyte |
| 50 | 0.0 | 227.7 ± 10.8 | 1670.8 ± 151.1 |
| 100 | 0.0 | 350.5 ± 31.9 | 1799.0 ± 414.5 |
| 200 | 0.0 | 665.4 ± 76.3 | 2610.3 ± 691.7 |
| 500 | 29.1 ± 25.3 | 1120.5 ± 215.6 | 4082.1 ± 738.5 |
| 1000 | 61.8 ± 2.9 | 1646.2 ± 194.1 | 6220.5 ± 774.8 | b

| | 6β-OH-Testosterone (pmol/min/mg protein) | | |
|---|---|---|---|
| Testosterone (μM) | TTF | iHep | Primary hepatocyte |
| 25 | 16.5 ± 9.7 | 193.3 ± 25.1 | 850.1 ± 41.8 |
| 50 | 72.7 ± 8.8 | 442.3 ± 52.9 | 1307.5 ± 28.0 |
| 100 | 162.3 ± 19.4 | 864.1 ± 27.0 | 2564.1 ± 921.7 |
| 200 | 407.5 ± 25.1 | 1574.4 ± 203.0 | 3693.7 ± 235.3 |
| 400 | 507.5 ± 25.9 | 1759.0 ± 142.7 | 4192.7 ± 716.4 | c

TABLE 4-continued

| | 4'-OH-Diclotenac (pmol/min/mg protein) | | |
|---|---|---|---|
| Diclofenac (μM) | TTF | iHep | Primary hepatocyte |
| 12.5 | 0.0 | 0.0 | 190.8 ± 22.8 |
| 25 | 2.8 ± 2.4 | 17.0 ± 8.0 | 283.1 ± 23.3 |
| 50 | 32.5 ± 13.6 | 195.4 ± 16.0 | 452.8 ± 47.6 |
| 100 | 119.8 ± 11.0 | 483.3 ± 60.1 | 785.6 ± 77.9 |
| 200 | 131.7 ± 28.5 | 756.7 ± 63.6 | 1484.6 ± 8.0 |

Example 4

In this example, the iHep cells prepared according to the method described above were transplanted into $Fah^{-/-}$ mice to examine whether the cells could proliferate in vivo and rescue the mice from death.

It was known that $Fah^{-/-}$ mice defective in tyrosine metabolism require 2-(2-nitro-4-trifluoro-methylbenzyol)-1,3-cyclohexanedione (NTBC) supply for survival (Grompe et al. Genes Dev. 7 (12A), 2298-2307 (1993), Wang et al. Proc. Natl. Acad. Sci. USA 100 (Suppl. 1), 11881-11888 (2003), Grompe et al. Nature Genet. 10, 453-460 (1995), and Overturf et al. Nature Genet. 12, 266-273 (1996)). After NTBC withdrawal ("NTBC-off"), $Fah^{-/-}$ mice undergo liver failure and death. They can be rescued by transplantation of wild-type primary hepatocytes, representing a useful model to characterize in vivo repopulation and functions of iHep cells. Immunodeficient $Fah^{-/-}Rag2^{-/-}$ mice were used for transplantation to reduce the likelihood of immunological rejection in the manner described above. The results are shown in FIGS. 3a and b and FIG. 14a.

It was found that ten $Fah^{-/-}Rag2^{-/-}$ mice without transplantation were all dead within 6.5 weeks after NTBC-off and showed continuous loss of body weight (FIG. 3b and FIG. 14b). Six $Fah^{-/-}Rag2^{-/-}$ mice transplanted with $p19^{Arf-/-}$ TTFs were also dead after NTBC-off (FIG. 3b). In contrast, 5 out of 12 $Fah^{-/-}Rag2^{-/-}$ mice transplanted with iHep cells ("iHep-$Fah^{-/-}Rag2^{-/-}$") were alive 8 weeks after NTBC-off and showed increased body weight (FIG. 3b and FIG. 14b, P<0.05).

Fah-positive ($Fah^+$) iHep cells engrafting into liver sinusoid comprised 5% to 80% of total hepatocytes in iHep-$Fah^{-/-}Rag2^{-/-}$ livers (FIG. 3c and FIG. 14c). Moreover, Fah-wild-type and $p19^{Arf}$-null alleles were detected in iHep-$Fah^{-/-}Rag2^{-/-}$ livers by genomic PCR (FIG. 14d). To exclude the possibility of cell fusion between iHep and host cells, the Y chromosome in male livers transplanted with female iHep cells was stained. Twenty-five $Fah^+$ nodules in four male recipients were characterized and all of them were found to be negative for Y-chromosome staining, confirming that iHep cells do not fuse with host cells (FIG. 3d and FIG. 14e). These results indicate that transplanted iHep cells can repopulate and rescue $Fah^{-/-}Rag2^{-/-}$ recipients and that, without fusion with recipient liver cells, the iHep cell repopulation restored the normal liver architecture by replacing $Fah^{-/-}$ hepatocytes in death.

Macroscopically, iHep-$Fah^{-/-}Rag2^{-/-}$ livers were found to be normal and healthy, whereas livers from NTBC-off $Fah^{-/-}Rag2^{-/-}$ control mice were swelled with many necrotic lesions (FIG. 4a). The hexagonal hepatic lobule was destructed due to massive cell death in NTBC-off $Fah^{-/-}Rag2^{-/-}$ livers (FIG. 15a). In contrast, iHep cell repopulation restored liver architecture without apparent cell death (FIGS. 15a and b).

Remarkably, both repopulated iHep cells and repopulated primary hepatocytes expressed Alb and other hepatic genes at comparable levels in Fah$^{-/-}$Rag2$^{-/-}$ mice (FIGS. 12c and d). As shown in FIG. 15d, Fah$^+$ nodules were isolated by laser-captured microdissection from four serial liver sections. The first section was immunostained with anti-Fah antibody to locate the repopulated Fah$^+$ nodules in the recipient livers (Fah$^+$ nodules were brown stained and indicated by yellow dash lines). Fah$^+$ tissues with the nodules were microdissected from the other 3 sections. After microdissection, those leftover sections on the slides were further stained with anti-Fah antibody to confirm that only the Fah$^+$ nodules were microdissected. Tissues from the same Fah$^+$ nodule were pooled for RNA extraction. In total, 3 iHep cell-repopulated nodules and 3 primary hepatocyte-repopulated nodules were analyzed. mRNA levels of indicated genes were measured in repopulated iHep cells and repopulated primary hepatoctyes in F/R recipient livers.

Moreover, serum levels of tyrosine, phenylalanine, ornithine, alanine and glycine were markedly reduced in iHep-Fah$^{-/-}$Rag2$^{-/-}$ mice compared to NTBC-off Fah$^{-/-}$Rag2$^{-/-}$ mice (FIGS. 4b and c, FIGS. 15e-g, and Table 5, P<0.05). iHep-Fah$^{-/-}$Rag2$^{-/-}$ mice also showed decreased levels of total bilirubin, alanine aminotransferase (ALT) and aspartate aminotransferase (AST) (FIGS. 4d-f and Table 6, P<0.05). These demonstrate that iHep cell transplantation substantially improves liver functions of NTBC-off Fah$^{-/-}$Rag2$^{-/-}$ mice.

Thus, in contrast with other cell-type conversion via lineage-specific transcription factors (Vierbuchen et al. Nature 463, 1035-1041 (2010); Ieda et al. Cell 142, 375-386 (2010); Szabo et al. Nature 468, 521-526 (2010)), the in vivo function of iHep cells has been rigorously proven.

Assays were also carried out to examine whether the above-described iHep cells are tumorigeneic. As shown in FIG. 16a, tumours were not found in iHep-Fah$^{-/-}$Rag2$^{-/-}$ livers 2 months after transplantation. Indeed, Ki67 staining revealed that iHep cells ceased proliferation 8 weeks after transplantation. Moreover, it was found that iHep cells did not form tumours 8 weeks after subcutaneous xenograft in NOD/SCID mice (FIG. 4g). A total of 20 out of 25 analyzed iHep cells displayed 40 chromosomes after 17 passages, which was comparable with results from wild-type cells. These results indicate that iHep cells are genetic stable and not tumor prone.

TABLE 5

| Amino Acid (μM) | WT | iHep-F/R | F/R |
|---|---|---|---|
| PSer | 0.52 ± 0.68 | 0.49 ± 0.05 | 0.36 ± 0.26 |
| PEtN | 12.04 ± 5.02 | 9.97 ± 4.48 | 8.35 ± 5.04 |
| Tau | 1399.34 ± 806.18 | 956.00 ± 276.36 | 1105.14 ± 224.65 |
| Asn | 77.47 ± 10.71 | 273.16 ± 96.83 | 450.1 ± 201.11 |
| Ser | 141.92 ± 34.58 | 543.45 ± 201.03* | 906.89 ± 300.94 |
| Hyp | 15.89 ± 5.30 | 44.72 ± 7.18 | 29.31 ± 6.91 |
| Gly | 302.60 ± 83.06 | 494.43 ± 64.26* | 822.22 ± 195.86 |
| Gln | 802.32 ± 283.57 | 2906.60 ± 759.27 | 13905.16 ± 10676.60 |
| Asp | 20.28 ± 8.66 | 31.36 ± 17.12 | 31.22 ± 5.63 |
| EtN | 24.45 ± 2.80 | 24.07 ± 1.87 | 27.52 ± 6.81 |
| His | 73.75 ± 8.60 | 487.09 ± 112.59 | 297.05 ± 97.62 |
| Thr | 170.47 ± 47.40 | 400.16 ± 74.42 | 710.75 ± 360.02 |
| Cit | 72.22 ± 16.14 | 83.31 ± 9.67* | 138.85 ± 45.06 |
| Sar | 2.25 ± 0.67 | 3.38 ± 0.57 | 4.07 ± 1.61 |
| bAla | 26.55 ± 14.12 | 5.58 ± 0.49 | 9.34 ± 8.04 |
| Ala | 366.18 ± 90.75 | 1084.20 ± 230.49* | 2440.45 ± 758.91 |
| Glu | 82.30 ± 9.48 | 227.73 ± 25.23 | 252.59 ± 45.78 |
| 1MHis | 5.12 ± 2.41 | 2.25 ± 4.40 | 6.81 ± 4.94 |
| 3MHis | 4.59 ± 2.15 | 0.79 ± 0.24 | 2.70 ± 3.99 |

TABLE 5-continued

| Amino Acid (μM) | WT | iHep-F/R | F/R |
|---|---|---|---|
| Asa | 351.54 ± 62.00 | 789.32 ± 106.77 | 709.38 ± 150.57 |
| Car | 1.99 ± 1.30 | 1.33 ± 0.63 | 1.83 ± 0.87 |
| Ans | 2.62 ± 2.13 | 1.23 ± 0.50 | 6.05 ± 5.75 |
| Hcit | 1.16 ± 0.50 | 0.44 ± 0.17 | 1.45 ± 1.37 |
| Arg | 137.66 ± 17.58 | 191.43 ± 92.04 | 258.05 ± 79.75 |
| Aad | 5.55 ± 3.00 | 12.29 ± 3.71 | 18.86 ± 12.62 |
| GABA | 6.79 ± 2.39 | 2.40 ± 1.52* | 5.77 ± 0.77 |
| bAib | 0.23 ± 0.44 | 0.63 ± 0.15 | 3.04 ± 4.27 |
| Abu | 3.98 ± 0.33 | 19.75 ± 4.88* | 29.90 ± 5.95 |
| Hyl | 1.64 ± 1.51 | 1.99 ± 0.39 | 2.92 ± 1.63 |
| Pro | 101.68 ± 44.63 | 254.53 ± 43.45* | 319.99 ± 49.87 |
| Orn | 85.33 ± 35.44 | 338.42 ± 118.75* | 700.91 ± 185.31 |
| Cth | 3.40 ± 1.62 | 3.15 ± 0.43 | 3.39 ± 1.49 |
| Cys | 7.51 ± 4.16 | 19.41 ± 11.92 | 31.33 ± 22.63 |
| Lys | 357.45 ± 52.18 | 754.45 ± 115.25 | 711.19 ± 167.79 |
| Met | 165.22 ± 171.12 | 141.78 ± 34.35 | 122.94 ± 64.57 |
| Val | 259.79 ± 75.90 | 377.65 ± 54.89 | 327.93 ± 58.18 |
| Tyr | 191.45 ± 132.69 | 536.39 ± 56.95* | 905.52 ± 265.61 |
| Hcy | 4.54 ± 0.79 | 0.99 ± 0.50 | 2.27 ± 1.75 |
| Ile | 95.63 ± 26.17 | 158.17 ± 18.15 | 121.09 ± 17.70 |
| Leu | 153.10 ± 56.61 | 246.50 ± 34.02 | 204.57 ± 21.14 |
| Phe | 88.08 ± 21.42 | 93.83 ± 13.86* | 220.80 ± 94.97 |
| Trp | 97.71 ± 19.59 | 121.03 ± 15.53* | 109.86 ± 27.12 |

Note:
Serum levels of amino acids were measured in wildtype mice (WT), F/R mice 8 weeks after iHep cell transplantation (iHep-F/R), and F/R mice with 20% body weight losing after NTBC removal (F/R).
Data are presented as mean ± s.d.
Asterisks indicate the values are significantly reduced compared with those in F/R mice (P < 0.05, t-test).

TABLE 6

| | Unit | WT | iHep-F/R | F/R |
|---|---|---|---|---|
| TBIL | μM | 0.45 ± 0.38 | 2.08 ± 1.34* | 45.68 ± 30.70 |
| ALB | g/L | 38.30 ± 1.89 | 25.46 ± 2.78 | 26.24 ± 5.47 |
| ALT | U/L | 24.05 ± 7.65 | 86.28 ± 36.47* | 153.92 ± 45.92 |
| AST | U/L | 138.68 ± 88.79 | 170.30 ± 40.27* | 308.82 ± 87.75 |
| BUN | mM | 10.0 ± 2.4 | 4.7 ± 0.5* | 9.4 ± 4.9 |
| Cr | μM | 11.7 ± 4.4 | 9.2 ± 1.3* | 13.4 ± 3.0 |

Note:
Serum levels of total bilirubin (TBIL), albumin (ALB), alanine transaminase (ALT), aspartate aminotransferase (AST), blood urea nitrogen (BUN), and Creatinine (Cr) were measured in wildtype mice (WT), F/R mice 8 weeks after iHep cell transplantation (iHep-F/R), and F/R mice with 20% body weight losing after NTBC removal (F/R).
Data are presented as mean ± s.d..
Asterisks indicate the values are significantly changed in iHep-F/R mice compared with those in F/R mice (P < 0.05, t-test).

Example 5

In this example, the above-described strategy for obtaining hepatocyte-like cells through direct lineage conversion was used to covert cells of human origin to human hepatocyte-like cells.

Briefly, human 293FT cells were forced to express human Foxa3 and Hnf1α, as well as human Gata4, by infecting the cells with Lentiviruses expressing the transcription factors in the same manner described above. Expressions of hepatic genes, such as Albumin, Afp, Transferrin, Ttr and Tat were analyze by RT-PCR using mRNAs isolated from 293FT cells 6 days after Lentiviral infection in the same manner described above. As shown in FIG. 17, the expressions of these hepatic genes were induced and up-regulated.

The same assays were conducted using (i) Lentiviruses expressing human Foxa2, Hnf1α, and human Gata4, or (ii) Lentiviruses expressing mouse Hnf1α, Foxa3, and Gata4 in human 293FT cells. As shown in FIG. 17, similar results were obtained.

The human 293FT cells expressing the heterologous mouse or human transcription factors were examined under a microspore. It was found that, six days after Lentiviral infection, the 293FT cells showed a morphological similar to primary cultured hepatocytes. See FIGS. 18A-D. The similar morphology was also observed in primary p19$^{Arf}$-null mouse TTFs that were infected with Lentiviruses expressing human FOXA3, HNF1A and GATA4. See FIG. 18E.

Furthermore, primary human fetal skin fibroblasts were infected with Lentiviruses expressing human FOXA3, HNF1A, and GATA4 in the same manner described above. As shown in FIG. 19, overexpression of human FOXA3, HNF1A, and GATA4 induced the formation of epithelial human iHep cells from fetal skin fibroblasts.

The above results demonstrate that human, non-liver cells can also be converted to hepatocyte-like cells via over-expressing as few as two (e.g., Hnf and Foxa) or three (Hnf, Foxa, and GATA) heterologous transcription factors. The 293FT cell line is a fast-growing, highly transfectable clonal isolate derived from human embryonic kidney cells transformed with the SV40 large T antigen. The above results also suggest that presence of the SV40 large T antigen, like the p19$^{Arf}$ knocking down, allowed the cells to by-pass proliferation arrest and associated cell death.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

---

What is claimed is:

1. A method of generating hepatocyte-like cells, the method comprising:
transducing a p19$^{Arf}$ null fibroblast with a retroviral vector encoding (i) Hnf1α, and (ii) Foxa2, Foxa3, or a combination thereof, thereby producing a transduced cell; and culturing the transduced cell in a medium for a period of time to obtain one or more progeny cells thereof, thereby generating hepatocyte-like cells.

2. The method of claim 1, further comprising expressing a GATA4 polypeptide in the p19$^{Arf}$ null fibroblast.

3. The method of claim 2, wherein the Hnf1α comprises the sequence of SEQ ID NO: 1; the Foxa3 comprises the sequence of SEQ ID NO: 2; and the GATA4 polypeptide comprises the sequence of SEQ ID NO: 3.

4. The method of claim 1, wherein the period of time is 2-30 days.

5. A hepatocyte-like cell produced by a method, the method comprising: transducing a p19$^{Arf}$ null fibroblast using with a retroviral vector encoding (i) Hnf1α; and (ii) Foxa2, Foxa3, or a combination thereof, thereby producing a transduced cell; and culturing the transduced cell in a medium for a period of time to obtain one or more progeny cells thereof, thereby producing the hepatocyte-like cell.

6. The hepatocyte-like cell of claim 5, the method further comprising expressing a GATA4 polypeptide in the p19$^{Arf}$ null fibroblast.

7. The hepatocyte-like cell of claim 5, wherein the hepatocyte-like cell is capable of metabolizing one or more compounds selected from the group consisting of phenacetin, testosterone, and diclofenac.

8. A pharmaceutical composition comprising:
a hepatocyte-like cell produced by a method comprising: transducing a p19$^{Arf}$ null fibroblast with a retroviral vector encoding (i) Hnf1α, and (ii) Foxa2, Foxa3, or a combination thereof, thereby producing a transduced cell; and culturing the transduced cell in a medium for a period of time to obtain one or more progeny cells thereof, thereby producing the hepatocyte-like cell; and
a pharmaceutically acceptable carrier.

9. The method of claim 4, wherein the period of time is 5-25 days.

10. The method of claim 9, wherein the period of time is 14-21 days.

11. The method of claim 1, wherein the Foxa2 comprises the sequence of SEQ ID NO: 5.

* * * * *